(12) United States Patent
Boelker et al.

(10) Patent No.: US 10,829,791 B2
(45) Date of Patent: Nov. 10, 2020

(54) MEANS AND METHODS FOR ITACONIC ACID PRODUCTION

(71) Applicants: Rheinisch-Westfaelische Technische Hochschule (RWTH) Aachen, Aachen (DE); Philipps-Universitaet Marburg, Marburg (DE)

(72) Inventors: Michael Boelker, Marburg (DE); Wolfgang Buckel, Marburg (DE); Sandra Hartmann, Gummersbach (DE); Lars M. Blank, Dortmund (DE); Nick Wierckx, Maastricht (NL); Elena Geiser, Aachen (DE)

(73) Assignee: RHEINISCH-WESTFAELISCHE TECHNISCHE HOCHSCHULE (RWTH) AACHEN, Aachen (DE)

( * ) Notice: Subject to any disclaimer, the term of this patent is extended or adjusted under 35 U.S.C. 154(b) by 32 days.

(21) Appl. No.: 15/127,894

(22) PCT Filed: Mar. 20, 2015

(86) PCT No.: PCT/EP2015/055976
§ 371 (c)(1),
(2) Date: Sep. 21, 2016

(87) PCT Pub. No.: WO2015/140314
PCT Pub. Date: Sep. 24, 2015

(65) Prior Publication Data
US 2017/0096690 A1    Apr. 6, 2017

(30) Foreign Application Priority Data
Mar. 21, 2014   (LU) .......................................... 92409

(51) Int. Cl.
| | | |
|---|---|---|
| C12P 7/46 | (2006.01) | |
| C12N 1/15 | (2006.01) | |
| C12N 1/19 | (2006.01) | |
| C12N 9/88 | (2006.01) | |
| C12N 9/90 | (2006.01) | |
| C07K 14/37 | (2006.01) | |
| C12N 15/52 | (2006.01) | |
| C12P 7/44 | (2006.01) | |
| C12N 9/02 | (2006.01) | |

(52) U.S. Cl.
CPC ............... *C12P 7/46* (2013.01); *C07K 14/37* (2013.01); *C12N 9/0071* (2013.01); *C12N 9/88* (2013.01); *C12N 9/90* (2013.01); *C12N 15/52* (2013.01); *C12P 7/44* (2013.01); *C12Y 401/01006* (2013.01); *C12Y 503/03007* (2013.01)

(58) Field of Classification Search
None
See application file for complete search history.

(56) References Cited

U.S. PATENT DOCUMENTS

| 2009/0172834 A1* | 7/2009 | Schauwecker ....... C07K 14/245 800/278 |
| 2013/0065279 A1* | 3/2013 | Burk ...................... C12P 19/32 435/88 |

FOREIGN PATENT DOCUMENTS

| WO | 2009104958 A1 | 8/2009 |
| WO | 2009110796 A1 | 9/2009 |

OTHER PUBLICATIONS

Genbank, Accession No. CP002657.1, 2011, www.ncbi.nlm.nih.gov.*
Guo et al., Protein tolerance to random amino acid change, Proc. Natl. Acad. Sci. USA, 2004, 10, 9205-10.*
Vargas et al., *Saccharomyces cerevisiae* Multidrug Transporter Qdr2p (Yil121wp), Antimicrobial Agents Chemotherapy, 2004, 48, 2531-37.*
Guo et al., Protein tolerance to random amino acid change, Proc. Natl. Acad. Sci. USA, 2004, 101, 9205-10.*
Uniprot, Accession No. R9P355, 2013, www.uniprot.org.*
Uniprot, Accession No. R9P313, 2013, www.uniprot.org.*
Uniprot, Accession No. M9LLU1, 2013, www.uniprot.org.*
Uniprot, Accession No. R9PC88, 2013, www.uniprot.org.*
Uniprot, Accession No. R9P2W9, 2013, www.uniprot.org.*
Uniprot, Accession No. G21V40, 2013, www.uniprot.org.*
Uniprot, Accession No. 00K907, 2013, www.uniprot.org.*
Uniprot, Accession No. R9P5M2, 2013, www.uniprot.org.*
Uniprot, Accession No. A0A0U2X0E4, 2016, www.uniport.org.*
Kamper et al., Insights from the genome of the biotrophic fungal plant pathogen Ustilago maydis, Nature, 2006, 444, 97-101.*
Panakova ("Itaconate production by Ustilago maydis; the influence of genes and cultivation conditions," Dissertation, RWTH Aachen University (Germany), 2014).*
Michelucci et al., Immune-responsive gene 1 protein links metabolism to immunity by catalyzing itaconic acid production, Proc. Natl. Acad. Sci. USA , 2013,110, 7820-25.*
Kaemper et al., "Insights from the genome of the biotrophic fungal plant pathogen Ustilago maydis", Nature, 444(7115); pp. 97-101, 2006.

(Continued)

*Primary Examiner* — Robert B Mondesi
*Assistant Examiner* — Todd M Epstein
(74) *Attorney, Agent, or Firm* — Riverside Law LLP

(57) ABSTRACT

The present invention relates to a method of producing itaconic acid. Further the present invention relates to nucleic acids encoding an aconitate-delta-isomerase (ADI) and trans-aconitate decarboxylase (TAD) and uses of such nucleic acids. Provided is additionally a recombinant host cell engineered to overexpress nucleic acids of the present invention. Furthermore an expression cassette and a vector are provided which include the respective nucleic acid.

26 Claims, 27 Drawing Sheets

Specification includes a Sequence Listing.

(56) References Cited

OTHER PUBLICATIONS

UniProt/EBI Accession No. Q4P485, dated Jul. 19, 2005; http://www.uniprot.org/uniprot/Q4P485.fasta?version=1.
UniProt/EBI Accession No. Q4P486, dated Jul. 19, 2005; http://www.uniprot.org/uniprot/Q4P486.fasta?version=1.
UniProt/EBI Accession No. Q4P484, dated Jul. 19, 2005; http://www.uniprot.org/uniprot/Q4P484.fasta?version=1.
UniProt/EBI Accession No. Q4P487, dated Jul. 19, 2005; http://www.uniprot.org/uniprot/Q4P487.fasta?version=1.
UniProt/EBI Accession No. Q4P483, dated Jul. 19, 2005; http://www.uniprot.org/uniprot/Q4P483.fasta?version=1.
UniProt/EBI Accession No. Q4P489, dated Jul. 19, 2005; http://www.uniprot.org/uniprot/Q4P489.fasta?version=1.
Garvey et al., "The three-dimensional crystal structure of the PrpF protein of Shewanella oneidensis complexed with trans-aconitate: Insights into its biological function", Protein Science, 16(7); pp. 1274-1284, 2007.
Klement et al., "Itaconic acid—A biotechnological process in change", Bioresource Technology, 135; pp. 422-431, 2013.
Maassen et al., "Influence of carbon and nitrogen concentration on itaconic acid production by the smut fungus Ustilago maydis", Engineering in Life Sciences,14(2); pp. 129-134, 2014.
Panakova et al., "High-level formation of itaconic acid by the fungus *Ustilago maydis*", New Biotechnology, 25S; p. S270, 2009.
Lee et al., "Microbial production of building block chemicals and polymers", Current Opinion in Biotechnology, 22(6); pp. 758-767, 2011.

\* cited by examiner

Itaconic acid production in deletion mutants and overexpression strains

| Gene | Deletion | Overexpression |
|---|---|---|
| Um05074 | 0 | - |
| Um12299 | 0 | 0 |
| Um05076 | -- | 0 |
| Um11777 | - | 0 |
| Um11778 | -- | 0 |
| Um05079 | - | ++ |
| Um05080 | -- | ++ |

Figure 4A

SEQ ID NO: 1 - Nucleic acid sequence adi1 UM11778 (ADI)

ATGTTGCATCCGATCGATACCACCATCTATCGTGCCGGCACCAGCCGCGGGCTCTACTTT
CTCGCCAGCGATCTGCCCGCTGAACCAAGCGAGCGAGATGCGGCGCTCATCTCGATCATG
GGCTCTGGTCATCCATTGCAGATCGATGGCATGGGCGGTGGCAATTCGTTGACCTCCAAG
GTGGCCATCGTCTCTGCTAGCACACAGCGCAGCGAGTTTGACGTCGACTATCTCTTCTGT
CAGGTCGGCATCACTGAGCGCTTTGTCGATACCGCCCCAACTGCGGCAATCTCATGTCG
GGCGTCGCTGCATTTGCCATTGAACGAGGTCTGGTGCAACCGCATCCGTCGGACACGACT
TGTCTGGTTCGCATCTTTAACCTCAACTCCAGACAGGCTTCCGAGCTCGTCATCCCGGTC
TACAACGGTCGCGTTCACTACGATGACATTGATGATATGCACATGCAGCGTCCTTCGGCG
CGCGTCGGGCTGCGCTTTCTCGACACGGTGGGCTCGTGCACTGGGAAGCTTCTGCCCACC
GGAAATGCGAGCGACTGGATCGACGGCCTCAAAGTGTCCATCATCGACTCGGCAGTCCCC
GTGGTGTTCATTCGTCAGCACGATGTTGGTATCACCGGTAGCGAGGCGCCCGCCACGCTC
AACGCCAACACTGCTCTCCTTGATCGGCTCGAGCGCGTTCGGCTCGAGGCGGGCCGACGC
ATGGGTCTCGGCGACGTCTCTGGTAGCGTAGTCCCCAAGCTTTCGCTCATCGGTCCCGGT
ACAGAGACGACCACGTTTACCGCACGCTgtaagtcgagtatttgttcgagatcgcatagc
gttgatacctagtggctgacgaatacgattcgtgttggagatggtcgacagATTTTACGC
CAAAGGCTTGTCACAACGCACATGCGGTGACGGGTGCCATCTGTACGGCCGGGGCGGCGT
ATATCGACGGAAGCGTGGTGTGCGAGATTCTTTCGTCGCGTGCTTCGGCGTGTAGCGCGT
CTCAGCGTCGCATTTCGATCGAGCATCCGAGCGGCGTGCTCGAGGTGGGTCTCGTACCGC
CTGAAAATGCGGCGCAGTCGCTCGTGGATGTGGCAGTGGTAGAGCGGTCCGTCGCGCTGA
TCGCGCATGCTCGCGTCTACTACACCACCCCAGATAGGCGGCGCTCGTACGACTCACCGC
TCACTTCGCCCTCCACGCCCGCCGACACGCACAACCTGTTCGATGCAGCGTACCGTCCCG
TGATACAGCCTAGTGACACTGACGTAGAGGCTCCACACATGCTTGCGCTCGAAAACAAGG
AGCAATGCGTGTCTCGGTGCGATACCGCGCTCCACCACATCGTAGCCAGCTACGGCGCTA
GCGATGCACACGCATCCGACCGCAGCCTCTCTTAG (variant, source MB215, sequenced, introns indicated by lowercase letters)

Figure 4B:

SEQ ID NO: 2 - Polypeptide sequence UM11778 (ADI)

MLHPIDTTIYRAGTSRGLYFLASDLPAEPSERDAALISIMGSGHPLQIDGMGGGNSLTSK
VAIVSASTQRSEFDVDYLFCQVGITERFVDTAPNCGNLMSGVAAFAIERGLVQPHPSDTT
CLVRIFNLNSRQASELVIPVYNGRVHYDDIDDMHMQRPSARVGLRFLDTVGSCTGKLLPT
GNASDWIDGLKVSIIDSAVPVVFIRQHDVGITGSEAPATLNANTALLDRLERVRLEAGRR
MGLGDVSGSVVPKLSLIGPGTETTTFTARYFTPKACHNAHAVTGAICTAGAAYIDGSVVC
EILSSRASACSASQRRISIEHPSGVLEVGLVPPENAAQSLVDVAVVERSVALIAHARVYY
TTPDRRRSYDSPLTSPSTPADTHNLFDAAYRPVIQPSDTDVEAPHMLALE̲NKEQCVSRCD
TALHHIVASYGASDAHASDRSLS*

(variant, derived from MB215 sequence, deviation at position 350 underlined)

Figure 4C

SEQ ID NO: 3 - Nucleic acid sequence UM11777

ATGGACCAAGCCGATCATTCCGGCGTCCCAGACGACGCTGCGCTCGAGGAGGCGCCCAAT
ACAGTACCGATTCAAGAAAAGAGCGCACAGCCTCACGACACGCAGCCGTACTGTGCATTC
ACGAAGCGGTCCAAGCTGTTTATCGTCCTCACCGTCTCTCTTGCCGGCTTTTTTTCGCCG
TTTGCCATCAACATTTACATCCCTGCCCTGCCCCAGATCGCCGGTATGCTGCATACCTCT
GAAGgtgagtgaaacctatcggctgaggcgcgaaacgtgcagagcaaccgattcgggagc
Cgtcaacttgttttctcattcacctctgtcctcctttccgcttcttctctttcccccctt
acaccttgccagCCGCTACCAACGTCACGGTGACCGTCTACATGATTGCACAGGGACTTT
CACCGGTTATCTGGGCTCCTCTCTCGGATgtgagtagccaaaattgcgctcggttggctt
Tagcttggcgtgtctctctctgaccacatatgcaagcgtttcttgcgttttttgggcttg
atcttgtctcgatcttgttgatgcatcacagGTGTTTGGGCGCCGACCGATCTACATCTT
GACGTTTTTCATCTTTTTCATTGCCAACCTCGGGCTGTCGTTCACCAACGTCTACTGGCT
CTTGGTGGTGCTGCGTATGGTGCAGGCTGCAGGCGCGTGCAGTGCGATTGCGATTGGCGC
TGGTACGATTGGCGACGTTACTGAGCGCAAGGAACGAGGAAGTTACATGGGCTACTATGC
GCTTGCGCAATACACGGGCCCCGCCATCGGACCGGTTGTCGGTGGCGCGCTTTCGCAGAG
ATGGGACTACCATGCTACGTTTTCTTCTTGACGGCGATCTCGGGTCCGTTTTGTTGTT
CATGCTTCTCTTTCTCGTTGAAACGCTTCGAGTCATTGTTGGCAACGGCAGTGCAAAAAC
GTCGGGCATCTATCGCCCCTTGGTGGAGCCCAAGCTGCAACGCTCGATCGCCAATGCGCC
TCGGCCTGGCATCAAGAACCCACTGCATGGCACGCTCGATTTCGGCTTCCACCGTCCGTT
TTTGGTGTTTGCGCGCCCCGAGACCAGCCTAGCCATCCTGGCTTTTTCGATGGTATATGC
GAGCTACTACTTGTCATCTGGTTCGCTGCCGTATCTGTTCAAGCAGGTGTACGGTCTGGA
CGAGCTCCTGATCGGCGTATGCTTTGTTCCGAGCGGTGTGGGGTGTGCGGTGGGCACAGT
GCTCGCCGGCAAGATCCTCGACTGGGACTATCGTCGTGCGTTGGACAAGAGCAAGCTTGG
TGTCAAGGTGACGCGCGCAAGGTTGCAGTCGGCGTGGATCTACCTGCCGTGCTACTGCGC
TTCGCTTCTGGCGTACGGATGGTGTGTTCGTGCGCATACGCATATCGCCGCTCCGATCGT
GTTTCAGTTTACACgtaggttgcagacccactcgctcggctagatactgtactgcgattg
ctgaccatgcttgtgtgctgttcgcatttggtgatttctacagTGGGCATGTTTTCGACC
ATGTACTTTACCAATGTCAATACGCTCATTGTCGACCTGTATCCTGGCAAAGCGGCCAGC
GCAACCGCAGCGGTCAACGTCGGACGGTGCTTGCTCGGCGCAGTAGCAGTCGCCGTGGTC
CAGCCCATGATCGACGCAATGGGCGCCGGCTGGACTTTTACGCTCGGCGCACTACTCACA
CTGATCGTCGGTCTCATCTGCCAAGTTCTCATCTACCTCTACGGCGAAATGTGGGCAGCT
CGCAAACACTCGTGA (U.maydis 521 data base entry Um11777, introns indicated by
lowercase letters)

Figure 4D

SEQ ID NO: 4 - Nucleic acid sequence UM05079 (CTP1)

ATGCCGCCGTCTGGCCGTAAAGTGTCGCCTAGCGTCTCAGTAGTAGCAGGAGCCACAGCC
GGCGCTGTTGAAGGAGgtgagtttacttggcgccaacacgaaatgacgaatcaccacgat
ctgaccaagagccggaaccgaatgcttgtgttgtcgcttggcttgttggtggatcagTCG
CTACGTTTCCGATCGAGTATCTCAAGACAGTTTCGCAGTTTGCACCGCGCGATGTGCACG
GGAACCAGCAGCGGCTATCTCCGATCGAGGTGGTCCGATCGACGCTCCAGAAGGAAGGTC
CCAAGGGGCTCTTTCGAGGCTGTACCGCTATGGTTGTAGGCAATGCCGGTAAGGCTGGTG
TACGATTTTTCGCTTTTGAAAACTTCCGCAGTATGCTCAAGAACAAGTCTACAgtaagtc
Ggcgcatctttctgctctacagtgcgagctagagcgtgttttgccattccacgacgctga
cgtttgccccgtttttggcggttgacctttagGGAAAATTGTCCAACTCGAGCAACTAC
CTTGCCGGTATGGGCGCCGGGACGTTAGAGGCCATCTTTGCCGTCACTCCGAGCGAGACG
ATCAgtgagtggcttcagcggtagatcaaaccacgcaattgcgcgcacccgaacgccaac
Tgaccggctggtgcggatgtttgtcttgttttgtttgatcattttcttcttatggctat
tgtgcggtacgcaacagAGACCAAGCTGATCGATGATAGCAAGCGAGCCAAGCCACGCTA
CGAGCAAGGGCTTGTGCGTGGTACGGCGTCGATTGTACGACAGGAAGGGTTGGCAGGCAT
CTACCAGGGGGTTGTACCGGTAGTGATGCGGCAGGGGTCTGCATCTGCGATTCGGCTGGG
GACGTACTCTGCGCTGCGAGATTGGCTTCCGAAAGCGCACGGTAGTGGATCGTCATTGAT
CAACTGGCTGGCTACGTTTTCGATCGGCGCGGCATCTGGCGTAGTCGCGGTGTATGGAAC
GATGCCATTCGACGTGCTGAAAACGCGCATGCAGGCCATAGACGCTGCACGCTACCGCTC
CACCTGGCACTGTCTCACCAACACCCTGAAAACAGAAGGCGCAGCTGCCCTGTGGCGTGG
CTCGGTATCACGCAGTATGCGTCTCATCGTCAGCGGAGGCGTCATCTTCTCGGTCTACGA
ACAGGTCGTCTGGCTCCTAGCAGGTCCCGAGTCGTAG
(U.maydis 521 data base entry Um05079, introns indicated by
lowercase letters)

Figure 4E

SEQ ID NO: 5 - Nucleic acid sequence UM12299

ATGTTGCGTTCTAGCCAGGCCAGAAGCGTGGTACGCTCCAGTCAGTGGGCCACCACCGCG
CGAGTTCACCAACTGGAGCTGCCAAGCGGGTGGAAGCCGAGCGCACTCGGAGTAGCACCA
TGGCAGCAGCGCCAGCAGCGCCAGCAGCGCCAGCTGTCGGTCAGGTCGCTCGATCACTTG
GTGATCACCTGCCACGATATGGACAAGACCATTGACTTTTACACGCGCCTCGGCATGGGC
GTGGTGCAGTTCGGACAAGGGCGCAAAGCGCTCGAGTTTGGCTCCCAGAAGATCAACCTG
CACCAGAAAGGCAAAGAGTTgtaagtacagtgtggtgtgtggtcagcaagcagctcaaca
aggacccaggccactgacaccgactttgtttgtctgcttggtctcggctcagCGAACCGA
gtaagttgcaaggcggcgcatgtggtgcggcgaatgtaggtggttgcgtggctgcgaatg
catgtactgacggttggctgtgtcttcagAGGCGTTGGTCCCGCAACCGGGATCCCAGGA
CTTGTGTTTCGTCATTCACGACAGCATCGCCGACGCCCAGgtaagaagcgtgtactagct
gcacccgtgcatccgtgcaaggcgcccttaagctgacgcctgagctctcgacagAAACAC
CTGCAAGAGCACGGCATCCAAGTTGTCGAGGGCCCCGTCAAGCGCACCGGTGCTGTCGGA
CCGATCCTCAGCATCTACGTGCGCGATCCCGACAATAACCTGATCGAGgtgagtgccaag
ccccgcgatttctcagtgcaatacaaacaagcctcgctaacacacacgtctgctctccagC
TCTCGTCGTACCAAGACGCAAAGTGA
(U.maydis 521 data base entry Um012299, introns indicated by
lowercase letters, manually corrected for wrong intron
prediction)

Figure 4F

SEQ ID NO: 6 - Nucleic acid sequence UM05076 (TAD)

ATGGCACCTGCACTCAACGCAAACCCTACCACGAAACGCGACGAGCTGAGCGCTCCGTCG
GCATCGCACAAGCTCGGCATGTCGAGCATGGCGAGCAGGGCGGCAGGCGGCGGTCTCAAG
CTCACTGGTCTGCCCGATCTCTCGGACTCGGCAGGAACGCTGAGCGACATTTTCGGTACG
CCGCAGATGCGCGAGATCTGGTCGGACCAGAACCGTGTGGCGTGCTATCTCGAGATCGAA
GCGGCGCTCGCGATTGTGCAGGCGGATCTCGGGATCATCCCCAAGAATGCGGCACACGAG
ATCGTCGAACACTGCCGCGTTCAAGAGATCGACTGGGCTCTGTACAAGCAAAAGACCGAG
CTGATCGGCTACCCCGTGCTGGGCATCGTGCAGCAGCTCGTCGCCAACTGCAAAGATGGT
CTCGGCGAGTACTGTCACTGGGGCGCCACAACGCAGGATATCACTGACACCGCCACCGTC
ATGCAGATCCGCCAGTCGCTCACGCTCGTCAAGCAGAGACTCGACAGCATCGTCTCGAGC
CTCGAGCATCTCGCCGAGCAGCATCGCAACGTGCCCATGGCGGCTCGTTCCAACCTCAAG
CAGGCGGTACCGATCACGTTTGGCTTCAAGATGGCGCGCTTCCTCGCCACGTTCCGCCGA
CACCAGCAGCGTCTCGTCGAGCTCGAAAAGCGCGTCTACACGCTCGAGTTTGGCGGTGCA
GCGGGCAACTTGTCGTCGCTGGGTGACCAGGGCATTGCGACGCACGATGCGCTTGCCAAG
ATGCTCGACCTGGCGCCCGCCGAGATTGCGTGGCACACGGAACACGACCGCTTCGCCGAG
GTAGGTACCTTCCTCGGCCTGCTCACTGGAACGCTTGCCAAACTCGCCACCGACATCAAG
CTCATGTCGCAGACCGAGGTGGGCGAGGTGGGCGAGCCGTTTATCTCGAACCGCGGCTCG
TCGTCGACGATGCCACAGAAGAACAATCCGATCTCGTGTGTCTACATTCACGCGTGTGCG
GCGAATGTGCGTCAGGGCGCTGCAGCGCTACTCGATGCCATGCAGTCTGATCACGAACGT
GGCACGGGTCCCTGGGAGATCATCTGGGTCCAGCTGCCACTCATGATGAACTGGACCTCG
GCCGCTCTCAACAACGCCGACTTTGTCCTGCGCGGCCTCCAGGTGTTCCCAGACGCAATG
CAACACAACCTGGACCTCTCGAAAGGGCTCATCGTCTCGGAAGCCGTCATGATGGGTCTC
GGTAACACGCTCGGCCGTCAGTACGCACACGACGCCGTCTACGAATGCTGTCGAACCGCG
TTCGTCCAAGACAGACCGCTCCTCGACGTCCTCCTCGAAAATCACGAGATCGCCTCCAAA
CTAGACCGCACCGAGCTTGAAAAACTCTGTGATCCCGCCAACTACCTCGGCCAGTGTTCG
CAGTGGATCGATCGCGTGCTGTCTCGCCCATCGTCGGCCTGA
(U.maydis 521 data base entry Um005076, no intron)

Figure 4G

SEQ ID NO: 7 - Nucleic acid sequence UM11778 (ADI)

ATGTTGCATCCGATCGATACCACCATCTATCGTGCCGGCACCAGCCGCGGGCTCTACTTT
CTCGCCAGCGATCTGCCCGCTGAACCAAGCGAGCGAGATGCGGCGCTCATCTCGATCATG
GGCTCTGGTCATCCATTGCAGATCGATGGCATGGGCGGTGGCAATTCGTTGACCTCCAAG
GTGGCCATCGTCTCTGCTAGCACACAGCGCAGCGAGTTTGACGTCGACTATCTCTTCTGT
CAGGTCGGCATCACTGAGCGCTTTGTCGATACCGCCCCAACTGCGGCAATCTCATGTCG
GGCGTCGCTGCATTTGCCATTGAACGAGGTCTGGTGCAACCGCATCCGTCGGACACGACT
TGTCTGGTTCGCATCTTTAACCTCAACTCCAGACAGGCTTCCGAGCTCGTCATCCCGGTC
TACAACGGTCGCGTTCACTACGATGACATTGATGATATGCACATGCAGCGTCCTTCGGCG
CGCGTCGGGCTGCGCTTTCTCGACACGGTGGGCTCGTGCACTGGGAAGCTTCTGCCCACC
GGAAATGCGAGCGACTGGATCGACGGCCTCAAAGTGTCCATCATCGACTCGGCAGTCCCC
GTGGTGTTCATTCGTCAGCACGATGTTGGTATCACCGGTAGCGAGGCGCCCGCCACGCTC
AACGCCAACACTGCTCTCCTTGATCGGCTCGAGCGCGTTCGGCTCGAGGCGGGCCGACGC
ATGGGTCTCGGCGACGTCTCTGGTAGCGTAGTCCCCAAGCTTTCGCTCATCGGTCCCGGT
ACAGAGACGACCACGTTTACCGCACGCTgtaagtcgagtatttgttcgagatcgcatagc
gttgatacctagtggctgacgaatacgattcgtgttggagatggtcgacagATTTTACGC
CAAAGGCTTGTCACAACGCACATGCGGTGACGGGTGCCATCTGTACGGCCGGGGCGGCGT
ATATCGACGGAAGCGTGGTGTGCGAGATTCTTTCGTCGCGTGCTTCGGCGTGTAGCGCGT
CTCAGCGTCGCATTTCGATCGAGCATCCGAGCGGCGTGCTCGAGGTGGGTCTCGTACCGC
CTGAAAATGCGGCGCAGTCGCTCGTGGATGTGGCAGTGGTAGAGCGGTCCATCGCGCTGA
TCGCGCATGCTCGCGTCTACTACACCACCCAGATAGGCGGCGCTCGTACGACTCACCGC
TCACTTCGCCCTCCACGCCCGCCGACACGCACAACCTGTTCGATGCAGCGTACCGTCCCG
TGATACAGCCTAGTGACACTGACGTAGAGGCTCCACACATGCTTGCGCTCGAAAACAAGG
AGCAATGCGTGTCTCGGTGCGATACCGCGCTCCACCACATCGTAGCCAGCTACGGCGCTA
GCGATGCACACGCATCCGACCGCAGCCTCTCTTAG
(U.maydis 521 data base entry Um11778, introns indicated by
lowercase letters)

Figure 4H

SEQ ID NO: 8 - Nucleic acid sequence UM05080 (Txf)

ATGCGCTTTGCAGGGATGAGTTGCGACGACGAGCGTCCTGCCAACATGTTTGATCTGATGGC
GCCACAGTTGGCCTCGACATCGTGCAACGAGCACTACTTTTCCACTGCGGACTTGGGAGCTT
CGACGTTGTACGCCACGACGACGGATGCACCAGCCACGATAGCTGGCATACTTACGCCACAG
CCAGCGACGTTGGCTCCGATGTACAGCACGTGTCCGGTGCGTTTTGACGACCAGCGCTCTGC
ACCGGCATCCACATCCGTGTCGGGCAAACGCAAACACTCGGACGTGGAAAAGGACCGTCGAA
GAAGCATTTCAAATGGGTTTGCGgtaagtaggctacttggcctcgttggatcacgcgccagc
cgaagctcaagctgaccgaatgcgttgaatggtgcatgaacctgtgcgtcgacttgatcagG
TGCTGCAGAATGTGCTTCACAACGAGTCCAACGCTAAACCGATCTCCAAGTCGATTCTGCTC
CAGCAGGCGTGCGACGAGATCCGCGAACTTCGCAAGAAACTCGACGCTAGTACTACCATCAT
CTCGCGGTTTGGTCTGGAAAACCTGTTCGTACCCACACCCTCATCCACGCATGCGTCGCCGC
CGAATGCGTCTAGTCGAATCTACTCGCCCATCAACCAGGCTTCCGATGTACTGGCTGATACA
CGTCGTGCTTCCATATCGACGAGTGCTACGCCGATCCTGTATAGCGAAGAGAAGCGCAAGGC
GAATGCGAAACGCAGACACTCGTACGATGGGTCGTGGCAAGCATCGGATCGTGGCTCGATCG
ACGACGAAGCCAGTGCCAGTGCCAGTGCCAGTAGCAGCGCTAGCTGTAGCAGTAGTAGCCAC
ACGCATTCCGACGATACCGACTGCGACGACACCGACACCGACATCCC
AGCCGAATCCGCACTCAAGGAGAGAACCAAACGCCACAAGGCCAGATCCAAGAAAGAACGAG
ATCGCACCAAACCGCGTTACAGACCGAAACCATCAACCAACCGTTCACCAACTCCGTCCTCC
TGCGCTTCCAGTACGCCCAACTCGCCGCCCACATCATCCAACCGCAACCGCGACCTCCAACA
GGCCATCCTCTCTCTCCTTCTCGAACTCCCCTCGCATCTCGAAGACGTCAAAAACAAAAGAC
GTGCTTCGCAACCAACCGAACTCGCCGATCCTTCCAGCGTAAAGTCCAGGTCCAAGAAACGT
CACCGATAA
(U.maydis 521 data base entry Um05080, introns indicated by
lowercase letters)

Figure 4I

SEQ ID NO: 9 - Nucleic acid sequence UM05074 (P450)

ATGAACACGACCAAACTACTCGGTACCGGGGCGCTCAGCCCGTCATTTGTGTTTGACCAC
GATTCTGGCAACGCCATCTTTGGACTTTCGAGCTCGACGCTGGTTGTTCTTGTAGCCATG
ATCGCGGTCTCGACGCTCACGCTCAAGAGCGTACTGCCCGGAGATCGCAGCATCAATCTT
CCGGGACCTCGAGGCTGGCCGATCGTCGGCTCTTGGTTCGATCTCGGCAACAACTGGGCC
GAGTACTTCCGTCAAGCTGCCAAAGAATACGGTGATgtgcgtctctcgtggtttccgcag
Tgcatccatgtctcgtgtggttggcatgggtcgagctgacgtgctgacgtgctgacgttc
tgacgttctgacgtgtatcttgcctctgtatgtacgccagGTATTCAAAGTACACATCGG
GAATCGCACCGTGGTGGTCGTCAACTCACCCAAGGCGGCGCACATTCTGTTCAACGAACA
CGGCTCGTCGCTCATCTCACGACCATGGTTCTATACGTTCCACGGCGTGCTGTCCAAGTC
GTCTGCCTTCACTATCGGTACGTCGGCCTGGAGCGATAGCACAAAGAACAAGCGCAAGGC
AGCTGCCACTGCGCTCAATCGTCCGGCGGTCCAGTCGTACATGCCCATCATTGTCGAAGA
GTCGTTGGACGCCGTTCGTCGGATCCTCAACGACGGCAACGCGGGCAAGAACGGCATTGT
TCCGTACAGCTACTTTCAGCGTCTTGCGCTCAACACGAGCTTTCAGGTCAACTACGGCTT
CCGCATGGGCGAGCGCGACGACGGTCTGTTTGATGAAATCTCCGAGGTGATTGCTAAAGT
GGCCTCgtacgtatcagtcgactcgactcttgcacctacctgcttgacttgcattcgcga
tttgctaacttggcgctctgcttctcgtacagTGTTCGCGCTGTGACCGGTTCGTTGCAG
GACTACGTTCCGCTCATGCGCTACCTGCCGGCTAATGCAAAGAGCAAGGCGGCTGCTTCG
TACGGTCTGCGTCGTAAAAAGTTCATGTCGAAACTGTACGAAGAACTCGAGCAACGCGTC
AACCAAGGCAAGGATGAGAGTTGCATCAgtacgttgatcacatccaaccaagcgtgccag
Tcgtgccagtcgtgccaatcgtaccagacaggctgctcaccacactcaccactcttgttg

Figure 4I (cont.)

```
cttttcttgttcgcagCCGGCAACATCCTTAAAGACACTGAATCGCGCAAGAAGCTGTCT
CGCTTGGAGATCGACTCGATCTGTCTCTCGATGGTCTCGGCAGGTCTGGATACTTTTGCC
AACAgtgagttgctcaactcagagatacaacacaagtgcaccgatcccgtgtctgaccag
ttcttttctgtgtattggcgtgttggcagCAATGATCTGGACGATCGGTTTCCTGGCCAA
GCATCCAGAGATCCAGCGCAAGGCACAGGCCGAACTGTTGGCTCACTATCCGAACCGGGA
GCTTCCGCATGTTGACTCGGAGGACTTGGTGTATATCCATGCCATGGCCAAGGAGGCATC
ACGACTGTTCAACGTGTTCCGCATCTGTCTGCCGCGTACAAACGTGAGCGACGTCACCTA
CAACAACGCCGTGATTCCAGCGGGGACGACGTTTTTCCTCAACTCATGGGCGTGCAACGT
GGACGCTGAAAAGTTCGCCGACCCGTTCGAGTTCAAGCCGGAGCGCTTCATGGACAAGAG
CGCCAGTAATGCACACGTCGAGAACAAGATGGGCGGCGTCGAGACGTACGCTTTCGGCAT
GGGAAGACGCATGTGTCCCGGCGTGTTCTTGGCGCTTCGCGAAATCTACACGACGCTCGT
CTTCCTCACCCACTTTTTCGATATTGCTCCCGACGGAGAGTATGACATCGACCCTCTCAC
AGCCGTAGAGGACGGTCGCGCGTTCAGCGTACGTCCGAAACCGTTCAAGGTGCGCTGCAC
GCCTCGACCCGGCGTCGACCTTTCCCCCGTGCTCGACAAACAATAG
```
(U.maydis 521 data base entry Um05074, introns indicated by lowercase letters)

Figure 4J

SEQ ID NO: 10 - Polypeptide sequence UM11778 (ADI)

```
MLHPIDTTIYRAGTSRGLYFLASDLPAEPSERDAALISIMGSGHPLQIDGMGGGNSLTSK
VAIVSASTQRSEFDVDYLFCQVGITERFVDTAPNCGNLMSGVAAFAIERGLVQPHPSDTT
CLVRIFNLNSRQASELVIPVYNGRVHYDDIDDMHMQRPSARVGLRFLDTVGSCTGKLLPT
GNASDWIDGLKVSIIDSAVPVVFIRQHDVGITGSEAPATLNANTALLDRLERVRLEAGRR
MGLGDVSGSVVPKLSLIGPGTETTTFTARYFTPKACHNAHAVTGAICTAGAAYIDGSVVC
EILSSRASACSASQRRISIEHPSGVLEVGLVPPENAAQSLVDVAVVERSIALIAHARVYY
TTPDRRRSYDSPLTSPSTPADTHNLFDAAYRPVIQPSDTDVEAPHMLALENKEQCVSRCD
TALHHIVASYGASDAHASDRSLS*
```
(U.maydis 521 data base entry Um11778)

Figure 4K

SEQ ID NO: 11 - Polypeptide sequence UM05074 (P450)

MNTTKLLGTGALSPSFVFDHDSGNAIFGLSSSTLVVLVAMIAVSTLTLKSVLPGDRSINL
PGPRGWPIVGSWFDLGNNWAEYFRQAAKEYGDVFKVHIGNRTVVVVNSPKAAHILFNEHG
SSLISRPWFYTFHGVLSKSSAFTIGTSAWSDSTKNKRKAAATALNRPAVQSYMPIIVEES
LDAVRRILNDGNAGKNGIVPYSYFQRLALNTSFQVNYGFRMGERDDGLFDEISEVIAKVA
SVRAVTGSLQDYVPLMRYLPANAKSKAAASYGLRRKKFMSKLYEELEQRVNQGKDESCIT
GNILKDTESRKKLSRLEIDSICLSMVSAGLDTFANTMIWTIGFLAKHPEIQRKAQAELLA
HYPNRELPHVDSEDLVYIHAMAKEASRLFNVFRICLPRTNVSDVTYNNAVIPAGTTFFLN
SWACNVDAEKFADPFEFKPERFMDKSASNAHVENKMGGVETYAFGMGRRMCPGVFLALRE
IYTTLVFLTHFFDIAPDGEYDIDPLTAVEDGRAFSVRPKPFKVRCTPRPGVDLSPVLDKQ
(U.maydis 521 data base entry Um05074)

Figure 4L

SEQ ID NO: 12 - Polypeptide sequence UM12299 (Dioxygenase)

MLRSSQARSVVRSSQWATTARVHQLELPSGWKPSALGVAPWQQRQQRQQRQLSVRSLDHL
VITCHDMDKTIDFYTRLGMGVVQFGQGRKALEFGSQKINLHQKGKEFEPKALVPQPGSQD
LCFVIHDSIADAQKHLQEHGIQVVEGPVKRTGAVGPILSIYVRDPDNNLIELSSYQDAK
(U.maydis 521 data base entry Um12299, manually corrected for
wrong intron prediction)

Figure 4M

SEQ ID NO: 13 - Polypeptide sequence UM05076 (TAD)

MAPALNANPTTKRDELSAPSASHKLGMSSMASRAAGGGLKLTGLPDLSDSAGTLSDIFGT
PQMREIWSDQNRVACYLEIEAALAIVQADLGIIPKNAAHEIVEHCRVQEIDWALYKQKTE
LIGYPVLGIVQQLVANCKDGLGEYCHWGATTQDITDTATVMQIRQSLTLVKQRLDSIVSS
LEHLAEQHRNVPMAARSNLKQAVPITFGFKMARFLATFRRHQQRLVELEKRVYTLEFGGA
AGNLSSLGDQGIATHDALAKMLDLAPAEIAWHTEHDRFAEVGTFLGLLTGTLAKLATDIK
LMSQTEVGEVGEPFISNRGSSSTMPQKNNPISCVYIHACAANVRQGAAALLDAMQSDHER
GTGPWEIIWVQLPLMMNWTSAALNNADFVLRGLQVFPDAMQHNLDLSKGLIVSEAVMMGL
GNTLGRQYAHDAVYECCRTAFVQDRPLLDVLLENHEIASKLDRTELEKLCDPANYLGQCS
QWIDRVLSRPSSA*
(U.maydis 521 data base entry Um05076)

Figure 4N

SEQ ID NO: 14 - Polypeptide sequence UM11777

MDQADHSGVPDDAALEEAPNTVPIQEKSAQPHDTQPYCAFTKRSKLFIVLTVSLAGFFSP
FAINIYIPALPQIAGMLHTSEAATNVTVTVYMIAQGLSPVIWAPLSDVFGRRPIYILTFF
IFFIANLGLSFTNVYWLLVVLRMVQAAGACSAIAIGAGTIGDVTERKERGSYMGYYALAQ
YTGPAIGPVVGGALSQRWDYHATFFFLTAISGPFLLFMLLFLVETLRVIVGNGSAKTSGI
YRPLVEPKLQRSIANAPRPGIKNPLHGTLDFGFHRPFLVFARPETSLAILAFSMVYASYY
LSSGSLPYLFKQVYGLDELLIGVCFVPSGVGCAVGTVLAGKILDWDYRRALDKSKLGVKV
TRARLQSAWIYLPCYCASLLAYGWCVRAHTHIAAPIVFQFTLGMFSTMYFTNVNTLIVDL
YPGKAASATAAVNGRCLLGAVAVAVVQPMIDAMGAGWTFTLGALLTLIVGLICQVLIYL
YGEMWAARKHS
(U.maydis 521 data base entry Um11777)

Figure 4O

SEQ ID NO: 15 - Polypeptide sequence UM05079 (CTP1)

MPPSGRKVSPSVSVVAGATAGAVEGVATFPIEYLKTVSQFAPRDVHGNQQRLSPIEVVRS
TLQKEGPKGLFRGCTAMVVGNAGKAGVRFFAFENFRSMLKNKSTGKLSNSSNYLAGMGAG
TLEAIFAVTPSETIKTKLIDDSKRAKPRYEQGLVRGTASIVRQEGLAGIYQGVVPVVMRQ
GSASAIRLGTYSALRDWLPKAHGSGSSLINWLATFSIGAASGVVAVYGTMPFDVLKTRMQ
AIDAARYRSTWHCLTNTLKTEGAAALWRGSVSRSMRLIVSGGVIFSVYEQVVWLLAGPES
(U.maydis 521 data base entry Um05079)

Figure 4P

SEQ ID NO: 16 - Polypeptide sequence UM05080 (Txf)

MRFAGMSCDDERPANMFDLMAPQLASTSCNEHYFSTADLGASTLYATTTDAPATIAGILT
PQPATLAPMYSTCPVRFDDQRSAPASTSVSGKRKHSDVEKDRRRSISNGFAVLQNVLHNE
SNAKPISKSILLQQACDEIRELRKKLDASTTIISRFGLENLFVPTPSSTHASPPNASSRI
YSPINQASDVLADTRRASISTSATPILYSEEKRKANAKRRHSYDGSWQASDRGSIDDEAS
ASASASASSSASCSSSSHTHSDDTDCDDTDTDIPAESALKERTKRHKARSKKERDRTKPRYR
PKPSTNRSPTPSSCASSTPNSPPTSSNRNRDLQQAILSLLLELPSHLEDVKNKRRASQPT
ELADPSSVKSRSKKRHR
(U.maydis 521 data base entry Um05080)

Figure 4Q

SEQ ID NO: 17 - Nucleic acid sequence UM02807 (ADI2)

ATGTTGCTCCAGCCTACCTCGAGCCGTCACTTTGAAGACTTTCGCTATGTCGAGCCCAAG
ATCTTGACCAAAAGCGCTCTGCCCATCGCTCCGGGCGCGACTACGGCAGGTGCGTCTTCT
AGCAAGTCGCCATCGTTTGAACGTCGCTCCCTTCGCACGGTAATCATGCGAGCAGGAACC
TCAAAGGGACTTTTCATCAAGGCTTCCGATCTGCCCAGCTCTCGAGCCGAATGGCAAAAC
ATCTTGCCTTCGATCATGGGCAGTCCTGATCCGTTTGGCCGTCAGCTCAATGGATTGGGT
GGTGGCACTTCGACAACTTCCAAGATTGCTGTTGTCTCGCAGAGCTCTGCTCCTCACATC
GCCGACGTCGATTACCTGTTCATCCAGTGCCCCATCGAAGGCGACAAGCTCGACTTTACC
GGCAACTGCGGCAACATTCTTAGTGGTGTTGGCCCTTTTGCATTTGAAGAGGGTCTCATC
CCGGCGTCAGTCCTGGCACCACTTGCTGCATTCGCCAAGACCAACGGCAAAGGCCGACAA
GACAAGGTCGCACTCACTCTTCGCTGTCTCAACAACAACCAGCTCATCCGATCTACATTC
CTTGTTCGCAATGGAAAGCCGGTCGAATTTGGCGACGTGGTCATCGACGGTGTTGCAGGT
ACAGGCTCGCCGATCCAGTTGGATTTCCTTGACCCAGCGGGCAGCATGTGTACCTCGCTC
TGCCCCACTGGCAAACCTTTGGATTTGCTGCACATACACGGCGAAGACTTGCCGATCGAA
GTATCATGCGTCGATGCAGCCAATCCGTTCGTCTTTGTTCGGCTCTCCGACATTGATGAG
ACCCTGCGCGGAAACGAGCCAGCTTCCGTACTGGAACGCCACTCGGCTCGCGTAGAGCTG
ATCCGTCAAGCAGCCGCCGTCGTAATGGGTCTTGCACCCGACACGGCCACTGCAGCAAAG
ACCAAAGGCACACCCAAGATCTGTCTGGTTTCCGACGCGCTCCCCGGCTCCGACGCACAC
GTTCTCTCGCGAAGCTTCAGCATGGGTCGACCACATCCTGCATTACAGCTCTCCGGTGGT
GTCTGCCTCGCTGCTGCCTGCAGCATTCCAGGGTCGATCCCGAACCAGATTCTGCTCAAG
CAAACCAAGATGATGCCGGAAAGGCTCAAGTTCGCACACGCATGCGGTGCCATTGAAGCT
ACCGCGGATGTCGAGATGGATAGCAAGAGCCCGGTTGGCGTCACTGTGAGGAGCACGAGT
CTTTTCAGGACTGCAAGGAGACTGGCTTCTGCTGAAGCGTATTACCTCTCGCCTAGCCAG
TAG
(U.maydis 521 data base entry Um02807)

Figure 4R

SEQ ID NO: 18 - Polypeptide sequence UM02807 (ADI2)

MLLQPTSSRHFEDFRYVEPKILTKSALPIAPGATTAGASSSKSPSFERRSLRTVIMRAGT
SKGLFIKASDLPSSRAEWQNILPSIMGSPDPFGRQLNGLGGGTSTTSKIAVVSQSSAPHI
ADVDYLFIQCPIEGDKLDFTGNCGNILSGVGPFAFEEGLIPASVLAPLAAFAKTNGKGRQ
DKVALTLRCLNNNQLIRSTFLVRNGKPVEFGDVVIDGVAGTGSPIQLDFLDPAGSMCTSL
CPTGKPLDLLHIGEDLPIEVSCVDAANPFVFVRLSDIDETLRGNEPASVLERHSARVEL
IRQAAAVVMGLAPDTATAAKTKGTPKICLVSDALPGSDAHVLSRSFSMGRPHPALQLSGG
VCLAAACSIPGSIPNQILLKQTKMMPERLKFAHACGAIEATADVEMDSKSPVGVTVRSTS
LFRTARRLASAEAYYLSPSQ
(U.maydis 521 data base entry Um02807)

Figure 4S

SEQ ID NO: 19 - Nucleic acid sequence UM02806 (CFP1)

ATGTCGACAACAGAGAAACGAATCTCGCCTTCGCCCATGCACTCGCTGCTCGCCGGAACC
ATCGCCGGTGCGGTCGAAGGGTTTCTTACTTACCCGACCGAGTTTGTCAAGACGCAGGCT
CAGCTTGCCTCGAATGCAGCCGCAAGTGCCAGCAAGACATGTTCGGTCCCCAAGAGTGTT
CCGGGGGCGGTTCGACACATCTCGTATGGTGCATTGCCAGCGCACAAGCTCAACATCGCC
GCCGCCGCCGCCGCCACATCAGCACCATCAACCACTGTACCGATGCCAAAAGCAGGCGCC
TCGGCGATGCAGATTGTCCGGGATACTTGGAAGACTCGCGGGATCACTGGCTTCTTCAGC
GGCGCAGGTGCCATGGTTACGGGCAACTCTGCTAAAGCGGGTGTTCGCTTCCTCACGTAC
GATACGATTCAAAACCTTCTGCGACCAAAGTCGATCGATGCAAACCAGAAGCTCGGAATG
GGCAGATCGATCCTTGCCGGCTTCCTGGCTGGATCGGCCGAGGCGATGCTCGCGGTCACG
CCTTCCGAGGCGATCAAGACACGGATGATCCAGGATTCGCTGCAGCCTGCTCACATGCGC
AAGTACAAAGGCGCCATCGATGCGGTTCAAAAGATTGTGGGCGCTGAGGGCTTGGCTGGT
CTGTACAGAGGGTTGGGTGCCACGGTGCTGCGACAGGGAGCAAACTCATCGGTGAGGTTG
ACATCCTACTCCATCTTGAAATCCGTACAAACGCAAGCAGGCTATGCCAAGTCCACAGCA
GCGACATTCGCATCGGGAGCAGGCGCTGGCTTGATCACCGTCTACCTCACAATGCCGTTT
GACGTGGTCAAGACGCGAATGCAACAGTCACCCTCGACCACAGGAGCTACACAGAGCAAG
CCGAGCATCGTCTCGTGCGGTCTCGACATTGTCAAGAGGGAAGGAGTAAAGAGCCTCTGG
AAGGGTACCACCCCACGATTGACCAGGTTGATTTTCAGCGGTGGCATCGCGTTTACTGCT
TACGAGACGGTTATTGGCTGGCTCAACCCGACCACAGTTGCTTGA
(U.maydis 521 data base entry Um02806)

Figure 4T

SEQ ID NO: 20 - Polypeptide sequence UM02806 (CFP1)

MSTTEKRISPSPMHSLLAGTIAGAVEGFLTYPTEFVKTQAQLASNAAASASKTCSVPKSV
PGAVRHISYGALPAHKLNIAAAAATSAPSTTVPMPKAGASAMQIVRDTWKTRGITGFFS
GAGAMVTGNSAKAGVRFLTYDTIQNLLRPKSIDANQKLGMGRSILAGFLAGSAEAMLAVT
PSEAIKTRMIQDSLQPAHMRKYKGAIDAVQKIVGAEGLAGLYRGLGATVLRQGANSSVRL
TSYSILKSVQTQAGYAKSTAATFASGAGAGLITVYLTMPFDVVKTRMQQSPSTTGATQSK
PSIVSCGLDIVKREGVKSLWKGTTPRLTRLIFSGGIAFTAYETVIGWLNPTTVA
(U.maydis 521 data base entry Um02806)

Figure 4U

SEQ ID NO: 21 - Nucleic acid sequence UM02808 (regulator)

ATGAGGTGGAAACAAGTACACGCTGTACCTGGCAGTAACACCTCGGACACCTCGCGTCCG
TCGCAAGGCTCATCGGCTTTCTCTACCGCTTGCGATTTTTGCCGTCACCGAAAGATTCGT
TGCAATCGAGAACAGCCATGCGACAAGTGCCAGAAGCACGGTAGGGCCAACACGTGTCAC
TTTGAAGATGGTCGAACCAAAAAGCGCCAACGCCCAAACAATGCGGCTTGTGCGGCAGTA
CATCAAGACGAAAGCCGCGTTGGTCAGCTCGGGGACGAGCTCGAGCTCGAGCTCGAGATC
GCCCGTGTTGGTCAGCTTTCCGCGACGCCAGGTCGACACGGTAATGTACGCTTCAACCGC
GCTTCATCAGAGGCTGCTGGTCAAGTCAGCGTGGATGAAGCAAGTCGTGTTGAAGCGCAC
AATACGTCGGGCCAGGCTAAGGACGGCTCACACGCGTTTGCCAATCCACGGCTCAACGAG
ACTGCGTTCAGACATACCGCAGAGACGCACCATGCTGCTCCAGTAGCCCACACGGACGTG
CGTGCATCGTCTGTATCATGCTCGTCGCTGAATGCTGCAGTGCGGCCTCACAGCTCGTCA
CCTCTGCCGACTTCGCCAACTTCGTCGGCGGTCGCTAGCATCATTGCGGATCTGGGCGAT
CCGAGGCATTCAATCGGACATGCTGAACGGACGCGCGCCTCTGCGTCACCCAGCCAGCAA
GCTACACGTGGAGTCATGTCAAATCTGCGCGTCAACAATCGAGGCGAATCGCGATACCAC
GGTCCGACGAGTGCTTCGTTCAACGCGCCTGAAGCATTGAGCGAGGATTCTCGAGCTGGA
ATTGCGTCTGCGCAGGGCCGTCTCAGTGTGGATGGTGGCGGTGGCGCCAATCCAGCAGGT
GGTAGTCAAGAGCAGCGTGTCTCGCTGGATGCAGCCGTGCTCACCGACAGATTGACATCG
CTGGCTGCTCGCGAAAGACAGGAAGAGGTGATGAACGTTGTCGCTGGCAGACTCGACTTT
GACGGTGTAGAGCCTGAGCTGGCGATCCACCTGCTCAACTTGCACTGGAATCGGCAGCAT
CACGCCTACCTGGTCACGTACCGACCGCTGTTCATGCGGGATATGGCGGCTCCTCCAGGC
AAAGCAAAGTACTTTTCCAAGCTACTCTTCCACGCTATCCTGTTCGGTGCCGCCAAGTTT
TCAGACCGCATCAATCAGGTCAGGTCAGACGTCAATGATCCCTCGACGGCTGGCCAACAG
TTTCTCGAACGCGTCCAGCAACTGTTACCAGAAGCGTTGATCAAGAGCCGCATCACGACG
GTGCAAGCGTTGCTGTTACTCGCATGCACGCACTATGCCCGTGGTAGCGAGAGTGCAGCT
TGGCTACATTCCGGATTGGCTTTCCGCATGGCGATCGATCTGGGGATGAACGAAGATAGT
ATCGAGCTGGTTGCATCGGGCAACATGGCACTCGAGGAGCTCGAGCTTCGTCGACGTGTA
GTATGGGCCGCGTTTGTGATTGACAAGATCCACTCGCTCTACCAAGGTCGGCAGGCTTCG
ATTGAACGGCGCAACCTGTATGTGCCCATCGAGTTCCACGACCATTTCGAAGAGACCGAG
TTCTGGACGCCTGTTGCGTTTCACCGACCTCTGAGCGAGGCAGAGGCGCAAAGCAAAGCT
ACAGCCAGAGGCACCAACGCCGCCACTCCAGTGGCTACACGGGACCGATCTACAGTGTT
TCTACGTTTGCCGAGCTGTGCAGGCTGACGGTGATTATGGAAAGATCATCCAGATCTTC
TATTCGATCGATAGCGGTGCGCGATCCGAAAGAGCACAAACGGAACACTTGATTGAAATG
CGCTCCGAGCTCGCCGCTTGGCGCACGTCGTTGCCTGCACATCTGCGTATCGACTCGAGC
TCGCCAGCAGGTAGAAGTGGCGGCCAACGCTCTCGCACTTGCCCGCCCAATCTGATCTCG
TTGCACGCACTCTATCATGCGTTGACGATCCTGCTGAATCGACCATTCCTACCACATGGA
CATCTTCGCAGCGACGATGCAGCTTGCGGCAGATCGTCATGGAAAGCATGCGTGGATGCA
GCGTCGAGCATCTCGAGCCTCATGAATCTGTATCGTCAGACGGTGAGCATGAAGGGAGCG
CCGCAGCTCATCTCATACATCAACTTTGTGCTGCAGGAATTCACGTTCGTGTAGCAGCA
CAGCTGCAACAGTCCAACACGTCGAGCGAAGGTGCTAATCTGGCAGCCGCATCCAGTCGC
AGATACGAGCTGAAAGCGCTCCGACAATGCCTGCAGGATTTCGAGGAGAATCAAGATCCC
AACCCGGGCGTCGCTAAAGCCAAGAGTGTGATCCGCAACATGGCCGAGAGAGCTGGCATT
CTCAACCTGCTTCAAGACGACTCGGGAGAAGGTGGATTGTCGCCGATCAACCAAGATGAC
AGTCCACCGCTGATGAATCTCGTCGGCCACAGTGGTAGCCAAGCGAATCGAGGGGGTGCT
GCAAATCGCGTCGAGCTTGTTGGAGCAAGCGCACTTGCACGCCATGCGAGCGCGCTGTCC
ATGACAACACCGTCGTCCTCGACTTCGATCGCCGCAGCAGGAGGAGCAACAGCCGCATCA
GCAGCGTTGAATCGAGTAGACGCAGCGCAGAACTCAACTTCTGCACTCACACCGCCCTAC
GAGATCGACTTTGAAAGCATTCTCGCCTCGTTTGATCACTTTGAGTCCGCAGCCGGTCCT

Figure 4U (cont.)

```
GGTCGAGACGGCCTATTCGCAACAGGCACAGCGGATCCCAACACCAACTCGGACATTCTC
TTTGGCTTTCTTCGTGACTATGATGCACCCTCTGCCCTCTCGCTATGA
```
(U.maydis 521 data base entry Um02808)

Figure 4V

SEQ ID NO: 22 - Polypeptide sequence UM02808 (regulator)

```
MRWKQVHAVPGSNTSDTSRPSQGSSAFSTACDFCRHRKIRCNREQPCDKCQKHGRANTCH
FEDGRTKKRQRPNNAACAAVHQDESRVGQLGDELELELEIARVGQLSATPGRHGNVRFNR
ASSEAAGQVSVDEASRVEAHNTSGQAKDGSHAFANPRLNETAFRHTAETHHAAPVAHTDV
RASSVSCSSLNAAVRPHSSSPLPTSPTSSAVASIIADLGDPRHSIGHAERTRASASPSQQ
ATRGVMSNLRVNNRGESRYHGPTSASFNAPEALSEDSRAGIASAQGRLSVDGGGGANPAG
GSQEQRVSLDAAVLTDRLTSLAARERQEEVMNVVAGRLDFDGVEPELAIHLLNLHWNRQH
HAYLVTYRPLFMRDMAAPPGKAKYFSKLLFHAILFGAAKFSDRINQVRSDVNDPSTAGQQ
FLERVQQLLPEALIKSRITTVQALLLLACTHYARGSESAAWLHSGLAFRMAIDLGMNEDS
IELVASGNMALEELELRRRVVWAAFVIDKIHSLYQGRQASIERRNLYVPIEFHDHFEETE
FWTPVAFHRPLSEAEAQSKATARGTNAATPSGYTGPIYSVSTFAELCRLTVIMEKIIQIF
YSIDSGARSERAQTEHLIEMRSELAAWRTSLPAHLRIDSSSPAGRSGGQRSRTCPPNLIS
LHALYHALTILLNRPFLPHGHLRSDDAACGRSSWKACVDAASSISSLMNLYRQTVSMKGA
PQLISYINFCAAGIHVRVAAQLQQSNTSSEGANLAAASSRRYELKALRQCLQDFEENQDP
NPGVAKAKSVIRNMAERAGILNLLQDDSGEGGLSPINQDDSPPLMNLVGHSGSQANRGGA
ANRVELVGASALARHASALSMTTPSSSTSIAAAGGATAASAALNRVDAAQNSTSALTPPY
EIDFESILASFDHFESAAGPGRDGLFATGTADPNTNSDILFGFLRDYDAPSALSL
```
(U.maydis 521 data base entry Um02808)

Figure 13A
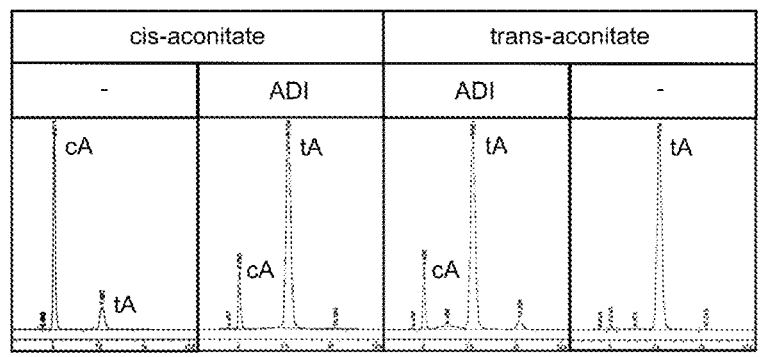
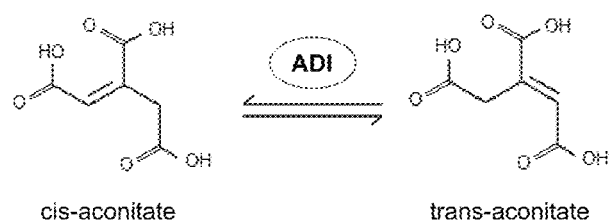
Figure 13B
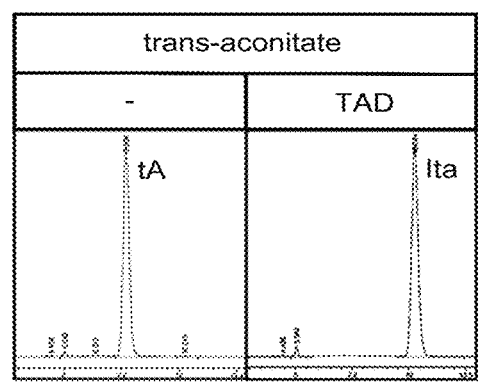
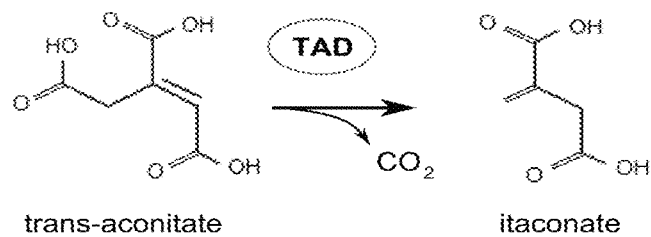

Figure 14
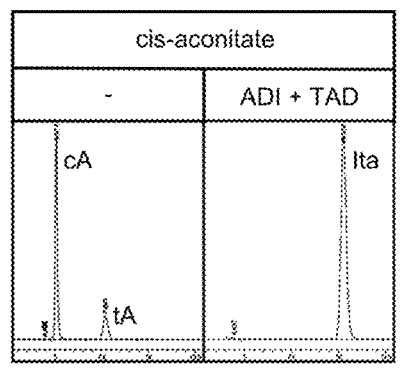
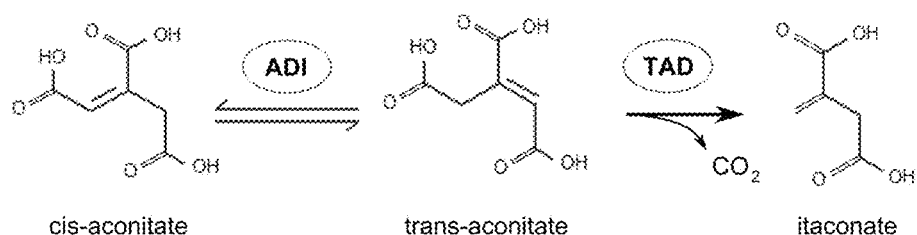
Figure 15
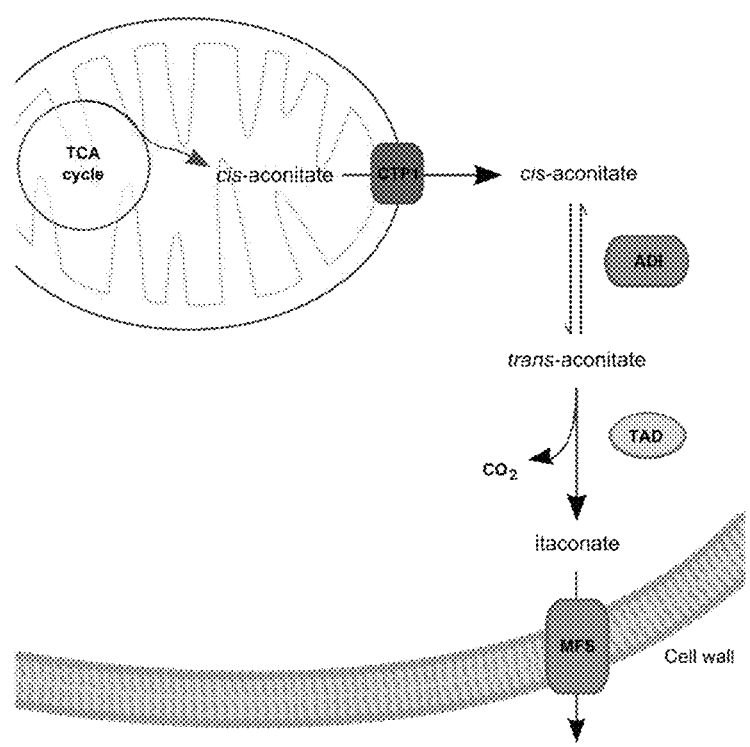

Figure 16
Figure 16 A
A
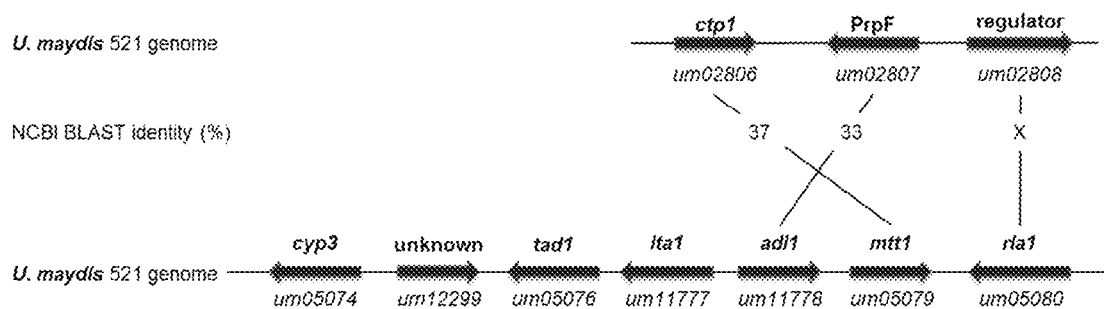
Figure 16B
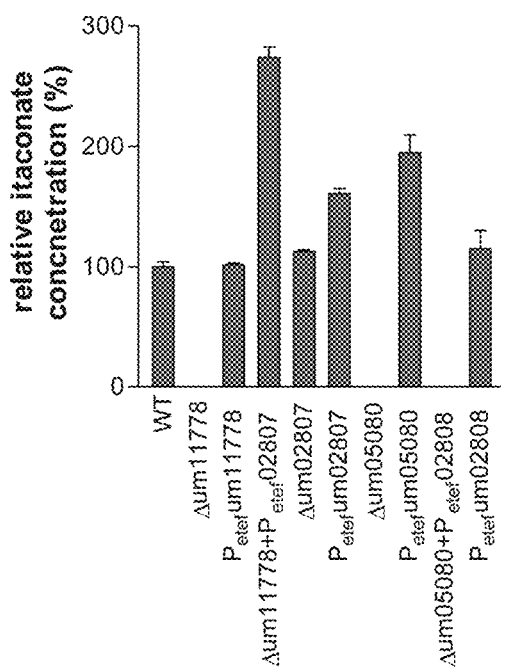

Figure 17

Pairwise sequence alignment between the polynucleotide sequences of UM11778 (SEQ ID NO: 1) and UM02807 (SEQ ID NO: 17).

```
um028075  1   LRTVIMRAGTSKGLFIKASDLPSSRAEWQNILPSIMGSPDPFGRQLNGLGGGTSTTSKIA  110
              + T I RAGTS+GL+  ASDLP+  +E   L SIMGS  P   Q++G+GGG S TSK+A
um11778   5   IDTTIYRAGTSRGLYFLASDLPAEPSERDAALISIMGSGHPL--QIDGMGGGNSLTSKVA  62 um02807  111  VVSQSSAPHIADVDYLFIQCPIEGDKLDFTGNCGNILSGVGPFAFEEGLI---PASVLAP  167
              +VS S+      DVDYLF Q I    +D   NCGN++SGV  FA E GL+    P+
um11778   63  IVSASTQRSEFDVDYLFCQVGITERFVDTAPNCGNLMSGVAAFAIERGLVQPHPSDTTCL  122 um02807  168  LAAFAKTNGKGRQDKVALTLRCLNNNQLIRSTFLVRNGKPVEFGDVVIDGVAGTGSPIQL  227
              +  F                 LN+ Q      V NG+ V + D+    +    + + L
um11778  123  VRIFN-----------------LNSRQASELVIPVYNGR-VHYDDIDDMHMQRPSARVGL  164 um02807  228  DFLDPAGSMCTSLCPTGKPLDLLHIHGEDLPIEVSCVDAANPFVFVRLSDIDETLRGNEP  287
                 FLD  GS    L PTG   D +         ++VS +D+A P VF+R  D+  T  G+E
um11778  165  RFLDTVGSCTGKLLPTGNASDWID------GLKVSIIDSAVPVVFIRQHDVGIT--GSEA  216 um02807  288  ASVLERHSA---RVELIRQAAAVVMGLAPDTATAAKTKGTPKICLVSDALPGSDAHVLS-  343
              + L  ++A    R+E +R  A   MGL   + +        PK+ L+    PG++    +
um11778  217  PATLNANTALLDRLERVRLEAGRRMGLGDVSGSV-----VPKLSLIG---PGTETTTFTA  268 um02807  344  RSFSMGRPHPALQLSGGVCLAAACSIPGSIPNQIL---LKQTKMMPERLKFAHACGAIE-  399
              R F+    H A  ++G +C A A  I GS+   +IL          R+   H  G  +E
um11778  269  RYFTPKACHNAHAVTGAICTAGAAYIDGSVVCEILSSRASACSASQRRISIEHPSGVLEV  328 um02807  400  ATADVEMDSKSPVGVTVRSTSLFRTARRLASAEAYYLSPSQ    440
                        E ++S V V  V    + R+    +A A  YY  +P +
um11778  329  GLVPPENAAQSLVDVAV----VERSIALIAHARVYYTTPDR    365
```

| Select for downloading or viewing reports | Description | Max score | Total score | Query cover | E value | Ident | Accession |
|---|---|---|---|---|---|---|---|
| Select seq | um11778 | 155 | 155 | 88% | 3e-46 | 33% | Query_29917 |

Sequences producing significant alignments:

Select: All None Selected:0

| Alignments | | | | | | |
|---|---|---|---|---|---|---|
| Description | Max score | Total score | Query cover | E value | Ident | Accession |
| um11778 | 155 | 155 | 88% | 3e-46 | 33% | Query_29917 |

SEQUENCE LISTING

```
<160> NUMBER OF SEQ ID NOS: 31

<210> SEQ ID NO 1
<211> LENGTH: 1415
<212> TYPE: DNA
<213> ORGANISM: Ustilago maydis

<400> SEQUENCE: 1
atgttgcatc cgatcgatac caccatctat cgtgccggca ccagccgcgg gctctacttt      60
ctcgccagcg atctgcccgc tgaaccaagc gagcgagatg cggcgctcat ctcgatcatg     120
ggctctggtc atccattgca gatcgatggc atgggcggtg gcaattcgtt gacctccaag     180
gtggccatcg tctctgctag cacacagcgc agcgagtttg acgtcgacta tctcttctgt     240
caggtcggca tcactgagcg ctttgtcgat accgccccca actgcggcaa tctcatgtcg     300
ggcgtcgctg catttgccat tgaacgaggt ctggtgcaac cgcatccgtc ggacacgact     360
tgtctggttc gcatctttaa cctcaactcc agacaggctt ccgagctcgt catcccggtc     420
tacaacggtc gcgttcacta cgatgacatt gatgatatgc acatgcagcg tccttcggcg     480
cgcgtcgggc tgcgctttct cgacacggtg ggctcgtgca ctgggaagct tctgcccacc     540
ggaaatgcga gcgactggat cgacggcctc aaagtgtcca tcatcgactc ggcagtcccc     600
gtggtgttca ttcgtcagca cgatgttggt atcaccggta gcgaggcgcc cgccacgctc     660
aacgccaaca ctgctctcct tgatcggctc gagcgcgttc ggctcgaggc gggccgacgc     720
atgggtctcg gcgacgtctc tggtagcgta gtccccaagc tttcgctcat cggtcccggt     780
acagagacga ccacgtttac cgcacgctgt aagtcgagta tttgttcgag atcgcatagc     840
gttgatacct agtggctgac gaatacgatt cgtgttggag atggtcgaca gattttacgc     900
caaaggcttg tcaacgcca catgcggtga cgggtgccat ctgtacggcc ggggcggcgt     960
atatcgacgg aagcgtggtg tgcgagattc tttcgtcgcg tgcttcggcg tgtagcgcgt    1020
ctcagcgtcg catttcgatc gagcatccga gcggcgtgct cgaggtgggt ctcgtaccgc    1080
ctgaaaatgc ggcgcagtcg ctcgtggatg tggcagtggt agagcggtcc gtcgcgctga    1140
tcgcgcatgc tcgcgtctac tacaccaccc cagataggcg gcgctcgtac gactcaccgc    1200
tcacttcgcc ctccacgccc gccgacacgc acaacctgtt cgatgcagcg taccgtcccg    1260
tgatacagcc tagtgacact gacgtagagg ctccacacat gcttgcgctc gaaaacaagg    1320
agcaatgcgt gtctcggtgc gataccgcgc tccaccacat cgtagccagc tacggcgcta    1380
gcgatgcaca cgcatccgac cgcagcctct cttag                              1415
```

<210> SEQ ID NO 2
<211> LENGTH: 443
<212> TYPE: PRT
<213> ORGANISM: Ustilago maydis

<400> SEQUENCE: 2

```
Met Leu His Pro Ile Asp Thr Thr Ile Tyr Arg Ala Gly Thr Ser Arg
1               5                   10                  15

Gly Leu Tyr Phe Leu Ala Ser Asp Leu Pro Ala Glu Pro Ser Glu Arg
            20                  25                  30

Asp Ala Ala Leu Ile Ser Ile Met Gly Ser Gly His Pro Leu Gln Ile
        35                  40                  45

Asp Gly Met Gly Gly Gly Asn Ser Leu Thr Ser Lys Val Ala Ile Val
    50                  55                  60

Ser Ala Ser Thr Gln Arg Ser Glu Phe Asp Val Asp Tyr Leu Phe Cys
65                  70                  75                  80

Gln Val Gly Ile Thr Glu Arg Phe Val Asp Thr Ala Pro Asn Cys Gly
                85                  90                  95

Asn Leu Met Ser Gly Val Ala Ala Phe Ala Ile Glu Arg Gly Leu Val
            100                 105                 110

Gln Pro His Pro Ser Asp Thr Thr Cys Leu Val Arg Ile Phe Asn Leu
        115                 120                 125

Asn Ser Arg Gln Ala Ser Glu Leu Val Ile Pro Val Tyr Asn Gly Arg
    130                 135                 140

Val His Tyr Asp Asp Ile Asp Asp Met His Met Gln Arg Pro Ser Ala
145                 150                 155                 160

Arg Val Gly Leu Arg Phe Leu Asp Thr Val Gly Ser Cys Thr Gly Lys
                165                 170                 175

Leu Leu Pro Thr Gly Asn Ala Ser Asp Trp Ile Asp Gly Leu Lys Val
            180                 185                 190

Ser Ile Ile Asp Ser Ala Val Pro Val Val Phe Ile Arg Gln His Asp
        195                 200                 205

Val Gly Ile Thr Gly Ser Glu Ala Pro Ala Thr Leu Asn Ala Asn Thr
    210                 215                 220

Ala Leu Leu Asp Arg Leu Glu Arg Val Arg Leu Glu Ala Gly Arg Arg
225                 230                 235                 240

Met Gly Leu Gly Asp Val Ser Gly Ser Val Val Pro Lys Leu Ser Leu
                245                 250                 255

Ile Gly Pro Gly Thr Glu Thr Thr Thr Phe Thr Ala Arg Tyr Phe Thr
            260                 265                 270

Pro Lys Ala Cys His Asn Ala His Ala Val Thr Gly Ala Ile Cys Thr
        275                 280                 285

Ala Gly Ala Ala Tyr Ile Asp Gly Ser Val Val Cys Glu Ile Leu Ser
    290                 295                 300

Ser Arg Ala Ser Ala Cys Ser Ala Ser Gln Arg Arg Ile Ser Ile Glu
305                 310                 315                 320

His Pro Ser Gly Val Leu Glu Val Gly Leu Val Pro Pro Glu Asn Ala
                325                 330                 335

Ala Gln Ser Leu Val Asp Val Ala Val Val Glu Arg Ser Val Ala Leu
            340                 345                 350

Ile Ala His Ala Arg Val Tyr Tyr Thr Thr Pro Asp Arg Arg Arg Ser
        355                 360                 365

Tyr Asp Ser Pro Leu Thr Ser Pro Ser Thr Pro Ala Asp Thr His Asn
    370                 375                 380
```

```
Leu Phe Asp Ala Ala Tyr Arg Pro Val Ile Gln Pro Ser Asp Thr Asp
385                 390                 395                 400

Val Glu Ala Pro His Met Leu Ala Leu Glu Asn Lys Glu Gln Cys Val
                405                 410                 415

Ser Arg Cys Asp Thr Ala Leu His His Ile Val Ala Ser Tyr Gly Ala
            420                 425                 430

Ser Asp Ala His Ala Ser Asp Arg Ser Leu Ser
            435                 440

<210> SEQ ID NO 3
<211> LENGTH: 1815
<212> TYPE: DNA
<213> ORGANISM: Ustilago maydis

<400> SEQUENCE: 3
```

| | | | | | |
|---|---|---|---|---|---|
| atggaccaag | ccgatcattc | cggcgtccca | gacgacgctg | cgctcgagga | ggcgcccaat | 60 |
| acagtaccga | ttcaagaaaa | gagcgcacag | cctcacgaca | cgcagccgta | ctgtgcattc | 120 |
| acgaagcggt | ccaagctgtt | tatcgtcctc | accgtctctc | ttgccggctt | tttttcgccg | 180 |
| tttgccatca | acatttacat | ccctgccctg | ccccagatcg | ccggtatgct | gcatacctct | 240 |
| gaaggtgagt | gaaacctatc | ggctgaggcg | cgaaacgtgc | agagcaaccg | attcgggagc | 300 |
| cgtcaacttg | ttttctcatt | cacctctgtc | ctcctttccg | cttcttctct | ttccccccctt | 360 |
| acaccttgcc | agccgctacc | aacgtcacgg | tgaccgtcta | catgattgca | cagggacttt | 420 |
| caccggttat | ctgggctcct | ctctcggatg | tgagtagcca | aaattgcgct | cggttggctt | 480 |
| tagcttggcg | tgtctctctc | tgaccacata | tgcaagcgtt | tcttgcgttt | tttgggcttg | 540 |
| atcttgtctc | gatcttgttg | atgcatcaca | ggtgtttggg | cgccgaccga | tctacatctt | 600 |
| gacgttttc | atctttttca | ttgccaacct | cgggctgtcg | ttcaccaacg | tctactggct | 660 |
| cttggtggtg | ctgcgtatgg | tgcaggctgc | aggcgcgtgc | agtgcgattg | cgattggcgc | 720 |
| tggtacgatt | ggcgacgtta | ctgagcgcaa | ggaacgagga | agttacatgg | gctactatgc | 780 |
| gcttgcgcaa | tacacgggcc | ccgccatcgg | accggttgtc | ggtggcgcgc | tttcgcagag | 840 |
| atgggactac | catgctacgt | ttttcttctt | gacggcgatc | tcgggtccgt | ttttgttgtt | 900 |
| catgcttctc | tttctcgttg | aaacgcttcg | agtcattgtt | ggcaacggca | gtgcaaaaac | 960 |
| gtcgggcatc | tatcgcccct | tggtggagcc | caagctgcaa | cgctcgatcg | ccaatgcgcc | 1020 |
| tcggcctggc | atcaagaacc | cactgcatgg | cacgctcgat | tcggcttcc | accgtccgtt | 1080 |
| tttggtgttt | gcgcgccccg | agaccagcct | agccatcctg | gcttttttcga | tggtatatgc | 1140 |
| gagctactac | ttgtcatctg | gttcgctgcc | gtatctgttc | aagcaggtgt | acggtctgga | 1200 |
| cgagctcctg | atcggcgtat | gctttgttcc | gagcggtgtg | gggtgtgcgg | tgggcacagt | 1260 |
| gctcgccggc | aagatcctcg | actgggacta | tcgtcgtgcg | ttggacaaga | gcaagcttgg | 1320 |
| tgtcaaggtg | acgcgcgcaa | ggttgcagtc | ggcgtggatc | tacctgccgt | gctactgcgc | 1380 |
| ttcgcttctg | gcgtacggat | ggtgtgttcg | tgcgcatacg | catatcgccg | ctccgatcgt | 1440 |
| gtttcagttt | acacgtaggt | tgcagaccca | ctcgctcggc | tagatactgt | actgcgattg | 1500 |
| ctgaccatgc | ttgtgtgctg | ttcgcatttg | gtgatttcta | cagtgggcat | gttttcgacc | 1560 |
| atgtacttta | ccaatgtcaa | tacgctcatt | gtcgacctgt | atcctggcaa | agcggccagc | 1620 |
| gcaaccgcag | cggtcaacgt | cggacggtgc | ttgctcggcg | cagtagcagt | cgccgtggtc | 1680 |
| cagcccatga | tcgacgcaat | gggcgccggc | tggactttta | cgctcggcgc | actactcaca | 1740 |

| | |
|---|---|
| ctgatcgtcg gtctcatctg ccaagttctc atctacctct acggcgaaat gtgggcagct | 1800 |
| cgcaaacact cgtga | 1815 |

<210> SEQ ID NO 4
<211> LENGTH: 1237
<212> TYPE: DNA
<213> ORGANISM: Ustilago maydis

<400> SEQUENCE: 4

| | |
|---|---|
| atgccgccgt ctggccgtaa agtgtcgcct agcgtctcag tagtagcagg agccacagcc | 60 |
| ggcgctgttg aaggaggtga gtttacttgg cgccaacacg aaatgacgaa tcaccacgat | 120 |
| ctgaccaaga gccggaaccg aatgcttgtg ttgtcgcttg gcttgttggt ggatcagtcg | 180 |
| ctacgtttcc gatcgagtat ctcaagacag tttcgcagtt tgcaccgcgc gatgtgcacg | 240 |
| ggaaccagca gcggctatct ccgatcgagg tggtccgatc gacgctccag aaggaaggtc | 300 |
| ccaaggggct ctttcgaggc tgtaccgcta tggttgtagg caatgccggt aaggctggtg | 360 |
| tacgattttt cgcttttgaa aacttccgca gtatgctcaa gaacaagtct acagtaagtc | 420 |
| ggcgcatctt tctgctctac agtgcgagct agagcgtgtt ttgccattcc acgacgctga | 480 |
| cgtttgcccc gttttttggc ggttgacctt tagggaaaat tgtccaactc gagcaactac | 540 |
| cttgccggta tgggcgccgg gacgttagag gccatctttg ccgtcactcc gagcgagacg | 600 |
| atcagtgagt ggcttcagcg gtagatcaaa ccacgcaatt gcgcgcaccc gaacgccaac | 660 |
| tgaccggctg gtgcggatgt ttgtcttgtt ttgtttgatc attttctctc ttatggctat | 720 |
| tgtgcggtac gcaacagaga ccaagctgat cgatgatagc aagcgagcca agccacgcta | 780 |
| cgagcaaggg cttgtgcgtg gtacggcgtc gattgtacga caggaagggt tgcaggcat | 840 |
| ctaccagggg gttgtaccgg tagtgatgcg gcagggtct gcatctgcga ttcggctggg | 900 |
| gacgtactct gcgctgcgag attggcttcc gaaagcgcac ggtagtggat cgtcattgat | 960 |
| caactggctg gctacgtttt cgatcggcgc ggcatctggc gtagtcgcgg tgtatggaac | 1020 |
| gatgccattc gacgtgctga aaacgcgcat gcaggccata gacgctgcac gctaccgctc | 1080 |
| cacctggcac tgtctcacca acaccctgaa aacagaaggc gcagctgccc tgtggcgtgg | 1140 |
| ctcggtatca cgcagtatgc gtctcatcgt cagcggaggc gtcatcttct cggtctacga | 1200 |
| acaggtcgtc tggctcctag caggtcccga gtcgtag | 1237 |

<210> SEQ ID NO 5
<211> LENGTH: 866
<212> TYPE: DNA
<213> ORGANISM: Ustilago maydis

<400> SEQUENCE: 5

| | |
|---|---|
| atgttgcgtt ctagccaggc cagaagcgtg gtacgctcca gtcagtgggc caccaccgcg | 60 |
| cgagttcacc aactggagct gccaagcggg tggaagccga gcgcactcgg agtagcacca | 120 |
| tggcagcagc gccagcagcg ccagcagcgc cagctgtcgg tcaggtcgct cgatcacttg | 180 |
| gtgatcacct gccacgatat ggacaagacc attgactttt acacgcgcct cggcatgggc | 240 |
| gtggtgcagt tcgacaaggg gcgcaaagcg ctcgagtttg ctcccagaa gatcaacctg | 300 |
| caccagaaag gcaaagagtt gtaagtacag tgtggtgtgt ggtcagcaag cagctcaaca | 360 |
| aggacccagg ccactgacac cgactttgtt tgtctgcttg gtctcggctc agcgaaccga | 420 |
| gtaagttgca aggcggcgca tgtggtgcgg cgaatgtagg tggttgcgtg gctgcgaatg | 480 |
| catgtactga cggttggctg tgtcttcaga ggcgttggtc ccgcaaccgg gatcccagga | 540 |

```
cttgtgtttc gtcattcacg acagcatcgc cgacgcccag gtaagaagcg tgtactagct    600
gcacccgtgc atccgtgcaa ggcgccctta agctgacgcc tgagctctcg acagaaacac    660
ctgcaagagc acggcatcca agttgtcgag ggccccgtca agcgcaccgg tgctgtcgga    720
ccgatcctca gcatctacgt gcgcgatccc gacaataacc tgatcgaggt gagtgccaag    780
ccccgcgatt ttcagtgcaa tacaaacaag cctcgctaac acacgtct gctctccagc    840 tctcgtcgta ccaagacgca aagtga                                         866
```

<210> SEQ ID NO 6
<211> LENGTH: 1482
<212> TYPE: DNA
<213> ORGANISM: Ustilago maydis

<400> SEQUENCE: 6

```
atggcacctg cactcaacgc aaaccctacc acgaaacgcg acgagctgag cgctccgtcg    60
gcatcgcaca agctcggcat gtcgagcatg gcgagcaggg cggcaggcgg cggtctcaag    120
ctcactggtc tgcccgatct ctcggactcg gcaggaacgc tgagcgacat tttcggtacg    180
ccgcagatgc gcgagatctg gtcggaccag aaccgtgtgg cgtgctatct cgagatcgaa    240
gcggcgctcg cgattgtgca ggcggatctc gggatcatcc caagaatgc ggcacacgag    300 atcgtcgaac actgccgcgt tcaagagatc gactgggctc tgtacaagca aaagaccgag    360
ctgatcggct accccgtgct gggcatcgtg cagcagctcg tcgccaactg caaagatggt    420
ctcggcgagt actgtcactg gggcgccaca acgcaggata tcactgacac cgccaccgtc    480
atgcagatcc gccagtcgct cacgctcgtc aagcagagac tcgacagcat cgtctcgagc    540
ctcgagcatc tcgccgagca gcatcgcaac gtgcccatgg cggctcgttc caacctcaag    600
caggcggtac cgatcacgtt tggcttcaag atggcgcgct tcctcgccac gttccgccga    660
caccagcagc gtctcgtcga gctcgaaaag cgcgtctaca cgctcgagtt tggcggtgca    720
gcgggcaact tgtcgtcgct gggtgaccag ggcattgcga cgcacgatgc gcttgccaag    780
atgctcgacc tggcgcccgc cgagattgcg tggcacacgg aacacgaccg cttcgccgag    840
gtaggtacct tcctcggcct gctcactgga acgcttgcca aactcgccac cgacatcaag    900
ctcatgtcgc agaccgaggt gggcgaggtg ggcgagccgt ttatctcgaa ccgcggctcg    960
tcgtcgacga tgccacagaa gaacaatccg atctcgtgtg tctacattca cgcgtgtgcg    1020
gcgaatgtgc gtcagggcgc tgcagcgcta ctcgatgcca tgcagtctga tcacgaacgt    1080
ggcacgggtc cctgggagat catctgggtc cagctgccac tcatgatgaa ctggacctcg    1140
gccgctctca caacgccga ctttgtcctg cgcggcctcc aggtgttccc agacgcaatg    1200
caacacaacc tggacctctc gaaagggctc atcgtctcgg aagccgtcat gatgggtctc    1260
ggtaacacgc tcggccgtca gtacgcacac gacgccgtct acgaatgctg tcgaaccgcg    1320
ttcgtccaag acagaccgct cctcgacgtc tcctcgaaaa atcacgagat cgcctccaaa    1380
ctagaccgca ccgagcttga aaaactctgt gatcccgcca actacctcgg ccagtgttcg    1440
cagtggatcg atcgcgtgct gtctcgccca tcgtcggcct ga                       1482
```

<210> SEQ ID NO 7
<211> LENGTH: 1415
<212> TYPE: DNA
<213> ORGANISM: Ustilago maydis

<400> SEQUENCE: 7

| | |
|---|---|
| atgttgcatc cgatcgatac caccatctat cgtgccggca ccagccgcgg gctctacttt | 60 |
| ctcgccagcg atctgcccgc tgaaccaagc gagcgagatg cggcgctcat ctcgatcatg | 120 |
| ggctctggtc atccattgca gatcgatggc atgggcggtg gcaattcgtt gacctccaag | 180 |
| gtggccatcg tctctgctag cacacagcgc agcgagtttg acgtcgacta tctcttctgt | 240 |
| caggtcggca tcactgagcg cttttgtcgat accgccccca actgcggcaa tctcatgtcg | 300 |
| ggcgtcgctg catttgccat tgaacgaggt ctggtgcaac cgcatccgtc ggacacgact | 360 |
| tgtctggttc gcatctttaa cctcaactcc agacaggctt ccgagctcgt catcccggtc | 420 |
| tacaacggtc gcgttcacta cgatgacatt gatgatatgc acatgcagcg tccttcggcg | 480 |
| cgcgtcgggc tgcgctttct cgacacggtg ggctcgtgca ctgggaagct tctgcccacc | 540 |
| ggaaatgcga cgactggat cgacggcctc aaagtgtcca tcatcgactc ggcagtcccc | 600 |
| gtggtgttca ttcgtcagca cgatgttggt atcaccggta gcgaggcgcc cgccacgctc | 660 |
| aacgccaaca ctgctctcct tgatcggctc gagcgcgttc ggctcgaggc gggccgacgc | 720 |
| atgggtctcg gcgacgtctc tggtagcgta gtccccaagc tttcgctcat cggtcccggt | 780 |
| acagagacga ccacgtttac cgcacgctgt aagtcgagta tttgttcgag atcgcatagc | 840 |
| gttgatacct agtggctgac gaatacgatt cgtgttggag atggtcgaca gattttacgc | 900 |
| caaaggcttg tcacaacgca catgcggtga cgggtgccat ctgtacggcc ggggcggcgt | 960 |
| atatcgacg aagcgtggtg tgcgagattc tttcgtcgcg tgcttcggcg tgtagcgcgt | 1020 |
| ctcagcgtcg catttcgatc gagcatccga gcggcgtgct cgaggtgggt ctcgtaccgc | 1080 |
| ctgaaaatgc ggcgcagtcg ctcgtggatg tggcagtggt agagcggtcc atcgcgctga | 1140 |
| tcgcgcatgc tcgcgtctac tacaccaccc cagataggcg gcgctcgtac gactcaccgc | 1200 |
| tcacttcgcc ctccacgccc gccgacacgc acaacctgtt cgatgcagcg taccgtcccg | 1260 |
| tgatacagcc tagtgacact gacgtagagg ctccacacat gcttgcgctc gaaaacaagg | 1320 |
| agcaatgcgt gtctcggtgc gataccgcgc tccaccacat cgtagccagc tacggcgcta | 1380 |
| gcgatgcaca cgcatccgac cgcagcctct cttag | 1415 |

<210> SEQ ID NO 8
<211> LENGTH: 1234
<212> TYPE: DNA
<213> ORGANISM: Ustilago maydis

<400> SEQUENCE: 8

| | |
|---|---|
| atgcgctttg cagggatgag ttgcgacgac gagcgtcctg ccaacatgtt tgatctgatg | 60 |
| gcgccacagt tggcctcgac atcgtgcaac gagcactact tttccactgc ggacttggga | 120 |
| gcttcgacgt tgtacgccac gacgacggat gcaccagcca cgatagctgg catacttacg | 180 |
| ccacagccag cgacgttggc tccgatgtac agcacgtgtc cggtgcgttt tgacgaccag | 240 |
| cgctctgcac cggcatccac atccgtgtcg ggcaaacgca aacactcgga cgtggaaaag | 300 |
| gaccgtcgaa gaagcatttc aaatgggttt gcggtaagta ggctacttgg cctcgttgga | 360 |
| tcacgcgcca gccgaagctc aagctgaccg aatgcgttga atggtgcatg aacctgtgcg | 420 |
| tcgacttgat caggtgctgc agaatgtgct tcacaacgag tccaacgcta aaccgatctc | 480 |
| caagtcgatt ctgctccagc aggcgtgcga cgagatccgc gaacttcgca agaaactcga | 540 |
| cgctagtact accatcatct cgcggttttgg tctggaaaac ctgttcgtac ccacaccctc | 600 |
| atccacgcat gcgtcgccgc cgaatgcgtc tagtcgaatc tactcgccca tcaaccaggc | 660 |
| ttccgatgta ctggctgata cacgtcgtgc ttccatatcg acgagtgcta cgccgatcct | 720 |

```
gtatagcgaa gagaagcgca aggcgaatgc gaaacgcaga cactcgtacg atgggtcgtg      780
gcaagcatcg gatcgtggct cgatcgacga cgaagccagt gccagtgcca gtgccagtag      840
cagcgctagc tgtagcagta gtagccacac gcattccgac gataccgact gcgacgacac      900
cgacaccgac atcccagccg aatccgcact caaggagaga accaaacgcc acaaggccag      960
atccaagaaa gaacgagatc gcaccaaacc gcgttacaga ccgaaaccat caaccaaccg     1020
ttcaccaact ccgtcctcct cgcgcttccag tacgcccaac tcgccgccca catcatccaa     1080
ccgcaaccgc gacctccaac aggccatcct ctctctcctt ctcgaactcc cctcgcatct     1140
cgaagacgtc aaaaacaaaa gacgtgcttc gcaaccaacc gaactcgccg atccttccag     1200
cgtaaagtcc aggtccaaga aacgtcaccg ataa                                 1234

<210> SEQ ID NO 9
<211> LENGTH: 2026
<212> TYPE: DNA
<213> ORGANISM: Ustilago maydis

<400> SEQUENCE: 9
atgaacacga ccaaactact cggtaccggg gcgctcagcc cgtcatttgt gtttgaccac       60
gattctggca acgccatctt tggactttcg agctcgacgc tggttgttct tgtagccatg      120
atcgcggtct cgacgctcac gctcaagagc gtactgcccg gagatcgcag catcaatctt      180
ccgggacctc gaggctggcc gatcgtcggc tcttggttcg atctcggcaa caactgggcc      240
gagtacttcc gtcaagctgc caaagaatac ggtgatgtgc gtctctcgtg gtttccgcag      300
tgcatccatg tctcgtgtgg ttggcatggg tcgagctgac gtgctgacgt gctgacgttc      360
tgacgttctg acgtgtatct tgcctctgta tgtacgccag gtattcaaag tacacatcgg      420
gaatcgcacc gtggtggtcg tcaactcacc caaggcggcg cacattctgt tcaacgaaca      480
cggctcgtcg ctcatctcac gaccatggtt ctatacgttc cacggcgtgc tgtccaagtc      540
gtctgccttc actatcggta cgtcggcctg gagcgatagc acaaagaaca gcgcaaggc      600 agctgccact cgcgctcaat cgtccggcggt ccagtcgtac atgcccatca ttgtcgaaga      660
gtcgttggac gccgttcgtc ggatcctcaa cgacggcaac gcgggcaaga acggcattgt      720
tccgtacagc tactttcagc gtcttgcgct caacacgagc tttcaggtca actacggctt      780
ccgcatgggc gagcgcgacg acggtctgtt tgatgaaatc tccgaggtga ttgctaaagt      840
ggcctcgtac gtatcagtcg actcgactct tgcacctacc tgcttgactt gcattcgcga      900
tttgctaact tggcgctctg cttctcgtac agtgttcgcg ctgtgaccgg ttcgttgcag      960
gactacgttc cgctcatgcg ctacctgccg gctaatgcaa agagcaaggc ggctgcttcg     1020
tacggtctgc gtcgtaaaaa gttcatgtcg aaactgtacg aagaactcga gcaacgcgtc     1080
aaccaaggca aggatgagag ttgcatcagt acgttgatca catccaacca agcgtgccag     1140
tcgtgccagt cgtgccaatc gtaccagaca ggctgctcac cacactcacc actcttgttg     1200
cttttcttgt tcgcagccgg caacatcctt aaagacactg aatcgcgcaa gaagctgtct     1260
cgcttggaga tcgactcgat ctgtctctcg atggtctcgg caggtctgga tacttttgcc     1320
aacagtgagt tgctcaactc agagatacaa cacaagtgca ccgatcccgt gtctgaccag     1380
ttcttttctg tgtattggcg tgttggcagc aatgatctgg acgatcggtt tcctggccaa     1440
gcatccagag atccagcgca aggcacaggc cgaactgttg gctcactatc cgaaccggga     1500
gcttccgcat gttgactcgg aggacttggt gtatatccat gccatggcca aggaggcatc     1560
```

```
acgactgttc aacgtgttcc gcatctgtct gccgcgtaca acgtgagcg acgtcaccta    1620 caacaacgcc gtgattccag cggggacgac gttttccctc aactcatggg cgtgcaacgt    1680
ggacgctgaa aagttcgccg acccgttcga gttcaagccg agcgcttca tggacaagag    1740 cgccagtaat gcacacgtcg agaacaagat gggcggcgtc gagacgtacg ctttcggcat    1800
gggaagacgc atgtgtcccg cgtgttctt ggcgcttcgc gaaatctaca cgacgctcgt    1860
cttcctcacc cacttttcg atattgctcc cgacggagag tatgacatcg accctctcac    1920
agccgtagag gacggtcgcg cgttcagcgt acgtccgaaa ccgttcaagg tgcgctgcac    1980
gcctcgaccc ggcgtcgacc tttcccccgt gctcgacaaa caatag                  2026
```

<210> SEQ ID NO 10
<211> LENGTH: 443
<212> TYPE: PRT
<213> ORGANISM: Ustilago maydis

<400> SEQUENCE: 10

```
Met Leu His Pro Ile Asp Thr Thr Ile Tyr Arg Ala Gly Thr Ser Arg
1               5                   10                  15

Gly Leu Tyr Phe Leu Ala Ser Asp Leu Pro Ala Glu Pro Ser Glu Arg
            20                  25                  30

Asp Ala Ala Leu Ile Ser Ile Met Gly Ser Gly His Pro Leu Gln Ile
        35                  40                  45

Asp Gly Met Gly Gly Gly Asn Ser Leu Thr Ser Lys Val Ala Ile Val
    50                  55                  60

Ser Ala Ser Thr Gln Arg Ser Glu Phe Asp Val Asp Tyr Leu Phe Cys
65                  70                  75                  80

Gln Val Gly Ile Thr Glu Arg Phe Val Asp Thr Ala Pro Asn Cys Gly
                85                  90                  95

Asn Leu Met Ser Gly Val Ala Ala Phe Ala Ile Glu Arg Gly Leu Val
            100                 105                 110

Gln Pro His Pro Ser Asp Thr Thr Cys Leu Val Arg Ile Phe Asn Leu
        115                 120                 125

Asn Ser Arg Gln Ala Ser Glu Leu Val Ile Pro Val Tyr Asn Gly Arg
    130                 135                 140

Val His Tyr Asp Asp Ile Asp Asp Met His Met Gln Arg Pro Ser Ala
145                 150                 155                 160

Arg Val Gly Leu Arg Phe Leu Asp Thr Val Gly Ser Cys Thr Gly Lys
                165                 170                 175

Leu Leu Pro Thr Gly Asn Ala Ser Asp Trp Ile Asp Gly Leu Lys Val
            180                 185                 190

Ser Ile Ile Asp Ser Ala Val Pro Val Val Phe Ile Arg Gln His Asp
        195                 200                 205

Val Gly Ile Thr Gly Ser Glu Ala Pro Ala Thr Leu Asn Ala Asn Thr
    210                 215                 220

Ala Leu Leu Asp Arg Leu Glu Arg Val Arg Leu Glu Ala Gly Arg Arg
225                 230                 235                 240

Met Gly Leu Gly Asp Val Ser Gly Ser Val Val Pro Lys Leu Ser Leu
                245                 250                 255

Ile Gly Pro Gly Thr Glu Thr Thr Thr Phe Thr Ala Arg Tyr Phe Thr
            260                 265                 270

Pro Lys Ala Cys His Asn Ala His Ala Val Thr Gly Ala Ile Cys Thr
        275                 280                 285

Ala Gly Ala Ala Tyr Ile Asp Gly Ser Val Val Cys Glu Ile Leu Ser
```

```
                290             295             300
Ser Arg Ala Ser Ala Cys Ser Ala Ser Gln Arg Arg Ile Ser Ile Glu
305             310             315             320

His Pro Ser Gly Val Leu Glu Val Gly Leu Val Pro Pro Glu Asn Ala
            325             330             335

Ala Gln Ser Leu Val Asp Val Ala Val Val Glu Arg Ser Ile Ala Leu
            340             345             350

Ile Ala His Ala Arg Val Tyr Tyr Thr Thr Pro Asp Arg Arg Ser
            355             360             365

Tyr Asp Ser Pro Leu Thr Ser Pro Ser Thr Pro Ala Asp Thr His Asn
            370             375             380

Leu Phe Asp Ala Ala Tyr Arg Pro Val Ile Gln Pro Ser Asp Thr Asp
385             390             395             400

Val Glu Ala Pro His Met Leu Ala Leu Glu Asn Lys Glu Gln Cys Val
            405             410             415

Ser Arg Cys Asp Thr Ala Leu His His Ile Val Ala Ser Tyr Gly Ala
            420             425             430

Ser Asp Ala His Ala Ser Asp Arg Ser Leu Ser
            435             440
```

<210> SEQ ID NO 11
<211> LENGTH: 540
<212> TYPE: PRT
<213> ORGANISM: Ustilago maydis

<400> SEQUENCE: 11

```
Met Asn Thr Thr Lys Leu Leu Gly Thr Gly Ala Leu Ser Pro Ser Phe
1               5               10              15

Val Phe Asp His Asp Ser Gly Asn Ala Ile Phe Gly Leu Ser Ser Ser
            20              25              30

Thr Leu Val Val Leu Val Ala Met Ile Ala Val Ser Thr Leu Thr Leu
            35              40              45

Lys Ser Val Leu Pro Gly Asp Arg Ser Ile Asn Leu Pro Gly Pro Arg
50              55              60

Gly Trp Pro Ile Val Gly Ser Trp Phe Asp Leu Gly Asn Asn Trp Ala
65              70              75              80

Glu Tyr Phe Arg Gln Ala Ala Lys Glu Tyr Gly Asp Val Phe Lys Val
            85              90              95

His Ile Gly Asn Arg Thr Val Val Val Asn Ser Pro Lys Ala Ala
            100             105             110

His Ile Leu Phe Asn Glu His Gly Ser Ser Leu Ile Ser Arg Pro Trp
            115             120             125

Phe Tyr Thr Phe His Gly Val Leu Ser Lys Ser Ala Phe Thr Ile
            130             135             140

Gly Thr Ser Ala Trp Ser Asp Ser Thr Lys Asn Lys Arg Lys Ala Ala
145             150             155             160

Ala Thr Ala Leu Asn Arg Pro Ala Val Gln Ser Tyr Met Pro Ile Ile
            165             170             175

Val Glu Glu Ser Leu Asp Ala Val Arg Arg Ile Leu Asn Asp Gly Asn
            180             185             190

Ala Gly Lys Asn Gly Ile Val Pro Tyr Ser Tyr Phe Gln Arg Leu Ala
            195             200             205

Leu Asn Thr Ser Phe Gln Val Asn Tyr Gly Phe Arg Met Gly Glu Arg
            210             215             220
```

Asp Asp Gly Leu Phe Asp Glu Ile Ser Glu Val Ile Ala Lys Val Ala
225                 230                 235                 240

Ser Val Arg Ala Val Thr Gly Ser Leu Gln Asp Tyr Val Pro Leu Met
            245                 250                 255

Arg Tyr Leu Pro Ala Asn Ala Lys Ser Lys Ala Ala Ser Tyr Gly
        260                 265                 270

Leu Arg Arg Lys Lys Phe Met Ser Lys Leu Tyr Glu Glu Leu Glu Gln
            275                 280                 285

Arg Val Asn Gln Gly Lys Asp Glu Ser Cys Ile Thr Gly Asn Ile Leu
        290                 295                 300

Lys Asp Thr Glu Ser Arg Lys Lys Leu Ser Arg Leu Glu Ile Asp Ser
305                 310                 315                 320

Ile Cys Leu Ser Met Val Ser Ala Gly Leu Asp Thr Phe Ala Asn Thr
            325                 330                 335

Met Ile Trp Thr Ile Gly Phe Leu Ala Lys His Pro Glu Ile Gln Arg
            340                 345                 350

Lys Ala Gln Ala Glu Leu Leu Ala His Tyr Pro Asn Arg Glu Leu Pro
            355                 360                 365

His Val Asp Ser Glu Asp Leu Val Tyr Ile His Ala Met Ala Lys Glu
370                 375                 380

Ala Ser Arg Leu Phe Asn Val Phe Arg Ile Cys Leu Pro Arg Thr Asn
385                 390                 395                 400

Val Ser Asp Val Thr Tyr Asn Asn Ala Val Ile Pro Ala Gly Thr Thr
            405                 410                 415

Phe Phe Leu Asn Ser Trp Ala Cys Asn Val Asp Ala Gly Lys Phe Ala
            420                 425                 430

Asp Pro Phe Glu Phe Lys Pro Glu Arg Phe Met Asp Lys Ser Ala Ser
            435                 440                 445

Asn Ala His Val Glu Asn Lys Met Gly Gly Val Glu Thr Tyr Ala Phe
450                 455                 460

Gly Met Gly Arg Arg Met Cys Pro Gly Val Phe Leu Ala Leu Arg Glu
465                 470                 475                 480

Ile Tyr Thr Thr Leu Val Phe Leu Thr His Phe Phe Asp Ile Ala Pro
            485                 490                 495

Asp Gly Glu Tyr Asp Ile Asp Pro Leu Thr Ala Val Glu Asp Gly Arg
            500                 505                 510

Ala Phe Ser Val Arg Pro Lys Pro Phe Lys Val Arg Cys Thr Pro Arg
            515                 520                 525

Pro Gly Val Asp Leu Ser Pro Val Leu Asp Lys Gln
530                 535                 540

<210> SEQ ID NO 12
<211> LENGTH: 179
<212> TYPE: PRT
<213> ORGANISM: Ustilago maydis

<400> SEQUENCE: 12

Met Leu Arg Ser Ser Gln Ala Arg Ser Val Val Arg Ser Ser Gln Trp
1               5                   10                  15

Ala Thr Thr Ala Arg Val His Gln Leu Glu Leu Pro Ser Gly Trp Lys
            20                  25                  30

Pro Ser Ala Leu Gly Val Ala Pro Trp Gln Gln Arg Gln Gln Arg Gln
        35                  40                  45

Gln Arg Gln Leu Ser Val Arg Ser Leu Asp His Leu Val Ile Thr Cys
    50                  55                  60

```
His Asp Met Asp Lys Thr Ile Asp Phe Tyr Thr Arg Leu Gly Met Gly
 65                  70                  75                  80

Val Val Gln Phe Gly Gln Gly Arg Lys Ala Leu Glu Phe Gly Ser Gln
                 85                  90                  95

Lys Ile Asn Leu His Gln Lys Gly Lys Glu Phe Glu Pro Lys Ala Leu
            100                 105                 110

Val Pro Gln Pro Gly Ser Gln Asp Leu Cys Phe Val Ile His Asp Ser
            115                 120                 125

Ile Ala Asp Ala Gln Lys His Leu Gln Glu His Gly Ile Gln Val Val
130                 135                 140

Glu Gly Pro Val Lys Arg Thr Gly Ala Val Gly Pro Ile Leu Ser Ile
145                 150                 155                 160

Tyr Val Arg Asp Pro Asp Asn Asn Leu Ile Glu Leu Ser Ser Tyr Gln
                165                 170                 175

Asp Ala Lys

<210> SEQ ID NO 13
<211> LENGTH: 493
<212> TYPE: PRT
<213> ORGANISM: Ustilago maydis

<400> SEQUENCE: 13

Met Ala Pro Ala Leu Asn Ala Asn Pro Thr Thr Lys Arg Asp Glu Leu
1               5                   10                  15

Ser Ala Pro Ser Ala Ser His Lys Leu Gly Met Ser Ser Met Ala Ser
            20                  25                  30

Arg Ala Ala Gly Gly Gly Leu Lys Leu Thr Gly Leu Pro Asp Leu Ser
        35                  40                  45

Asp Ser Ala Gly Thr Leu Ser Asp Ile Phe Gly Thr Pro Gln Met Arg
50                  55                  60

Glu Ile Trp Ser Asp Gln Asn Arg Val Ala Cys Tyr Leu Glu Ile Glu
65                  70                  75                  80

Ala Ala Leu Ala Ile Val Gln Ala Asp Leu Gly Ile Ile Pro Lys Asn
                85                  90                  95

Ala Ala His Glu Ile Val Glu His Cys Arg Val Gln Glu Ile Asp Trp
            100                 105                 110

Ala Leu Tyr Lys Gln Lys Thr Glu Leu Ile Gly Tyr Pro Val Leu Gly
        115                 120                 125

Ile Val Gln Gln Leu Val Ala Asn Cys Lys Asp Gly Leu Gly Glu Tyr
130                 135                 140

Cys His Trp Gly Ala Thr Thr Gln Asp Ile Thr Asp Thr Ala Thr Val
145                 150                 155                 160

Met Gln Ile Arg Gln Ser Leu Thr Leu Val Lys Gln Arg Leu Asp Ser
                165                 170                 175

Ile Val Ser Ser Leu Glu His Leu Ala Glu Gln His Arg Asn Val Pro
            180                 185                 190

Met Ala Ala Arg Ser Asn Leu Lys Gln Ala Val Pro Ile Thr Phe Gly
        195                 200                 205

Phe Lys Met Ala Arg Phe Leu Ala Thr Phe Arg Arg His Gln Gln Arg
210                 215                 220

Leu Val Glu Leu Glu Lys Arg Val Tyr Thr Leu Glu Phe Gly Gly Ala
225                 230                 235                 240

Ala Gly Asn Leu Ser Ser Leu Gly Asp Gln Gly Ile Ala Thr His Asp
                245                 250                 255
```

```
Ala Leu Ala Lys Met Leu Asp Leu Ala Pro Ala Glu Ile Ala Trp His
            260             265             270

Thr Glu His Asp Arg Phe Ala Glu Val Gly Thr Phe Leu Gly Leu Leu
            275             280             285

Thr Gly Thr Leu Ala Lys Leu Ala Thr Asp Ile Lys Leu Met Ser Gln
            290             295             300

Thr Glu Val Gly Glu Val Gly Glu Pro Phe Ile Ser Asn Arg Gly Ser
305             310             315             320

Ser Ser Thr Met Pro Gln Lys Asn Asn Pro Ile Ser Cys Val Tyr Ile
            325             330             335

His Ala Cys Ala Ala Asn Val Arg Gln Gly Ala Ala Leu Leu Asp
            340             345             350

Ala Met Gln Ser Asp His Glu Arg Gly Thr Gly Pro Trp Glu Ile Ile
            355             360             365

Trp Val Gln Leu Pro Leu Met Met Asn Trp Thr Ser Ala Ala Leu Asn
            370             375             380

Asn Ala Asp Phe Val Leu Arg Gly Leu Gln Val Phe Pro Asp Ala Met
385             390             395             400

Gln His Asn Leu Asp Leu Ser Lys Gly Leu Ile Val Ser Glu Ala Val
            405             410             415

Met Met Gly Leu Gly Asn Thr Leu Gly Arg Gln Tyr Ala His Asp Ala
            420             425             430

Val Tyr Glu Cys Cys Arg Thr Ala Phe Val Gln Asp Arg Pro Leu Leu
            435             440             445

Asp Val Leu Leu Glu Asn His Glu Ile Ala Ser Lys Leu Asp Arg Thr
            450             455             460

Glu Leu Glu Lys Leu Cys Asp Pro Ala Asn Tyr Leu Gly Gln Cys Ser
465             470             475             480

Gln Trp Ile Asp Arg Val Leu Ser Arg Pro Ser Ser Ala
            485             490

<210> SEQ ID NO 14
<211> LENGTH: 491
<212> TYPE: PRT
<213> ORGANISM: Ustilago maydis

<400> SEQUENCE: 14

Met Asp Gln Ala Asp His Ser Gly Val Pro Asp Ala Ala Leu Glu
1               5               10              15

Glu Ala Pro Asn Thr Val Pro Ile Gln Glu Lys Ser Ala Gln Pro His
            20              25              30

Asp Thr Gln Pro Tyr Cys Ala Phe Thr Lys Arg Ser Lys Leu Phe Ile
            35              40              45

Val Leu Thr Val Ser Leu Ala Gly Phe Phe Ser Pro Phe Ala Ile Asn
    50              55              60

Ile Tyr Ile Pro Ala Leu Pro Gln Ile Ala Gly Met Leu His Thr Ser
65              70              75              80

Glu Ala Ala Thr Asn Val Thr Val Thr Val Tyr Met Ile Ala Gln Gly
            85              90              95

Leu Ser Pro Val Ile Trp Ala Pro Leu Ser Asp Val Phe Gly Arg Arg
            100             105             110

Pro Ile Tyr Ile Leu Thr Phe Phe Ile Phe Phe Ile Ala Asn Leu Gly
            115             120             125

Leu Ser Phe Thr Asn Val Tyr Trp Leu Leu Val Val Leu Arg Met Val
```

130                 135                 140
Gln Ala Gly Ala Cys Ser Ala Ile Ala Ile Gly Ala Gly Thr Ile
145                 150                 155                 160

Gly Asp Val Thr Glu Arg Lys Glu Arg Gly Ser Tyr Met Gly Tyr Tyr
                165                 170                 175

Ala Leu Ala Gln Tyr Thr Gly Pro Ala Ile Gly Pro Val Val Gly Gly
                180                 185                 190

Ala Leu Ser Gln Arg Trp Asp Tyr His Ala Thr Phe Phe Phe Leu Thr
                195                 200                 205

Ala Ile Ser Gly Pro Phe Leu Leu Phe Met Leu Leu Phe Leu Val Glu
            210                 215                 220

Thr Leu Arg Val Ile Val Gly Asn Gly Ser Ala Lys Thr Ser Gly Ile
225                 230                 235                 240

Tyr Arg Pro Leu Val Glu Pro Lys Leu Gln Arg Ser Ile Ala Asn Ala
                245                 250                 255

Pro Arg Pro Gly Ile Lys Asn Pro Leu His Gly Thr Leu Asp Phe Gly
                260                 265                 270

Phe His Arg Pro Phe Leu Val Phe Ala Arg Pro Glu Thr Ser Leu Ala
            275                 280                 285

Ile Leu Ala Phe Ser Met Val Tyr Ala Ser Tyr Tyr Leu Ser Ser Gly
            290                 295                 300

Ser Leu Pro Tyr Leu Phe Lys Gln Val Tyr Gly Leu Asp Glu Leu Leu
305                 310                 315                 320

Ile Gly Val Cys Phe Val Pro Ser Gly Val Gly Cys Ala Val Gly Thr
                325                 330                 335

Val Leu Ala Gly Lys Ile Leu Asp Trp Asp Tyr Arg Arg Ala Leu Asp
                340                 345                 350

Lys Ser Lys Leu Gly Val Lys Val Thr Arg Ala Arg Leu Gln Ser Ala
                355                 360                 365

Trp Ile Tyr Leu Pro Cys Tyr Cys Ala Ser Leu Leu Ala Tyr Gly Trp
            370                 375                 380

Cys Val Arg Ala His Thr His Ile Ala Ala Pro Ile Val Phe Gln Phe
385                 390                 395                 400

Thr Leu Gly Met Phe Ser Thr Met Tyr Phe Thr Asn Val Asn Thr Leu
                405                 410                 415

Ile Val Asp Leu Tyr Pro Gly Lys Ala Ala Ser Ala Thr Ala Ala Val
                420                 425                 430

Asn Val Gly Arg Cys Leu Leu Gly Ala Val Ala Val Val Gln
            435                 440                 445

Pro Met Ile Asp Ala Met Gly Ala Gly Trp Thr Phe Thr Leu Gly Ala
450                 455                 460

Leu Leu Thr Leu Ile Val Gly Leu Ile Cys Gln Val Leu Ile Tyr Leu
465                 470                 475                 480

Tyr Gly Glu Met Trp Ala Ala Arg Lys His Ser
                485                 490

<210> SEQ ID NO 15
<211> LENGTH: 300
<212> TYPE: PRT
<213> ORGANISM: Ustilago maydis

<400> SEQUENCE: 15

Met Pro Pro Ser Gly Arg Lys Val Ser Pro Ser Val Ser Val Val Ala
1               5                   10                  15

Gly Ala Thr Ala Gly Ala Val Glu Gly Val Ala Thr Phe Pro Ile Glu
                20                  25                  30

Tyr Leu Lys Thr Val Ser Gln Phe Ala Pro Arg Asp Val His Gly Asn
            35                  40                  45

Gln Gln Arg Leu Ser Pro Ile Glu Val Val Arg Ser Thr Leu Gln Lys
50                      55                  60

Glu Gly Pro Lys Gly Leu Phe Arg Gly Cys Thr Ala Met Val Val Gly
65                  70                  75                  80

Asn Ala Gly Lys Ala Gly Val Arg Phe Phe Ala Phe Glu Asn Phe Arg
                85                  90                  95

Ser Met Leu Lys Asn Lys Ser Thr Gly Lys Leu Ser Asn Ser Ser Asn
            100                 105                 110

Tyr Leu Ala Gly Met Gly Ala Gly Thr Leu Glu Ala Ile Phe Ala Val
        115                 120                 125

Thr Pro Ser Glu Thr Ile Lys Thr Lys Leu Ile Asp Asp Ser Lys Arg
130                 135                 140

Ala Lys Pro Arg Tyr Glu Gln Gly Leu Val Arg Gly Thr Ala Ser Ile
145                 150                 155                 160

Val Arg Gln Glu Gly Leu Ala Gly Ile Tyr Gln Gly Val Val Pro Val
                165                 170                 175

Val Met Arg Gln Gly Ser Ala Ser Ala Ile Arg Leu Gly Thr Tyr Ser
            180                 185                 190

Ala Leu Arg Asp Trp Leu Pro Lys Ala His Gly Ser Gly Ser Ser Leu
        195                 200                 205

Ile Asn Trp Leu Ala Thr Phe Ser Ile Gly Ala Ala Ser Gly Val Val
210                 215                 220

Ala Val Tyr Gly Thr Met Pro Phe Asp Val Leu Lys Thr Arg Met Gln
225                 230                 235                 240

Ala Ile Asp Ala Ala Arg Tyr Arg Ser Thr His Cys Leu Thr Asn
                245                 250                 255

Thr Leu Lys Thr Glu Gly Ala Ala Leu Trp Arg Gly Ser Val Ser
            260                 265                 270

Arg Ser Met Arg Leu Ile Val Ser Gly Val Ile Phe Ser Val Tyr
        275                 280                 285

Glu Gln Val Val Trp Leu Leu Ala Gly Pro Glu Ser
290                 295                 300

<210> SEQ ID NO 16
<211> LENGTH: 377
<212> TYPE: PRT
<213> ORGANISM: Ustilago maydis

<400> SEQUENCE: 16

Met Arg Phe Ala Gly Met Ser Cys Asp Asp Glu Arg Pro Ala Asn Met
1               5                   10                  15

Phe Asp Leu Met Ala Pro Gln Leu Ala Ser Thr Ser Cys Asn Glu His
            20                  25                  30

Tyr Phe Ser Thr Ala Asp Leu Gly Ala Ser Thr Leu Tyr Ala Thr Thr
        35                  40                  45

Thr Asp Ala Pro Ala Thr Ile Ala Gly Ile Leu Thr Pro Gln Pro Ala
    50                  55                  60

Thr Leu Ala Pro Met Tyr Ser Thr Cys Pro Val Arg Phe Asp Asp Gln
65                  70                  75                  80

Arg Ser Ala Pro Ala Ser Thr Ser Val Ser Gly Lys Arg Lys His Ser
                85                  90                  95

```
Asp Val Glu Lys Asp Arg Arg Ser Ile Ser Asn Gly Phe Ala Val
            100                 105                 110
Leu Gln Asn Val Leu His Asn Glu Ser Asn Ala Lys Pro Ile Ser Lys
        115                 120                 125
Ser Ile Leu Leu Gln Gln Ala Cys Asp Glu Ile Arg Glu Leu Arg Lys
    130                 135                 140
Lys Leu Asp Ala Ser Thr Thr Ile Ile Ser Arg Phe Gly Leu Glu Asn
145                 150                 155                 160
Leu Phe Val Pro Thr Pro Ser Ser Thr His Ala Ser Pro Pro Asn Ala
                165                 170                 175
Ser Ser Arg Ile Tyr Ser Pro Ile Asn Gln Ala Ser Asp Val Leu Ala
            180                 185                 190
Asp Thr Arg Arg Ala Ser Ile Ser Thr Ser Ala Thr Pro Ile Leu Tyr
        195                 200                 205
Ser Glu Glu Lys Arg Lys Ala Asn Ala Lys Arg Arg His Ser Tyr Asp
    210                 215                 220
Gly Ser Trp Gln Ala Ser Asp Arg Gly Ser Ile Asp Asp Glu Ala Ser
225                 230                 235                 240
Ala Ser Ala Ser Ala Ser Ser Ala Ser Cys Ser Ser Ser Ser His
                245                 250                 255
Thr His Ser Asp Asp Thr Asp Cys Asp Asp Thr Asp Thr Asp Ile Pro
            260                 265                 270
Ala Glu Ser Ala Leu Lys Glu Arg Thr Lys Arg His Lys Ala Arg Ser
        275                 280                 285
Lys Lys Glu Arg Asp Arg Thr Lys Pro Arg Tyr Arg Pro Lys Pro Ser
    290                 295                 300
Thr Asn Arg Ser Pro Thr Pro Ser Ser Cys Ala Ser Ser Thr Pro Asn
305                 310                 315                 320
Ser Pro Pro Thr Ser Ser Asn Arg Asn Arg Asp Leu Gln Gln Ala Ile
                325                 330                 335
Leu Ser Leu Leu Leu Glu Leu Pro Ser His Leu Glu Asp Val Lys Asn
            340                 345                 350
Lys Arg Arg Ala Ser Gln Pro Thr Glu Leu Ala Asp Pro Ser Ser Val
        355                 360                 365
Lys Ser Arg Ser Lys Lys Arg His Arg
    370                 375

<210> SEQ ID NO 17
<211> LENGTH: 1323
<212> TYPE: DNA
<213> ORGANISM: Ustilago maydis

<400> SEQUENCE: 17
atgttgctcc agcctaccte gagccgtcac tttgaagact tcgctatgt cgagcccaag      60 atcttgacca aaagcgctct gcccatcgct ccgggcgcga ctacggcagg tgcgtcttct    120
agcaagtcgc catcgtttga acgtcgctcc cttcgcacgg taatcatgcg agcaggaacc    180
tcaaagggac tttcatcaa ggcttccgat ctgcccagct ctcgagccga atggcaaaac    240
atcttgcctt cgatcatggg cagtcctgat ccgtttggcc gtcagctcaa tggattgggt    300
ggtggcactt cgacaacttc caagattgct gttgtctcgc agagctctgc tcctcacatc    360
gccgacgtcg attacctgtt catccagtgc cccatcgaag cgacaagct cgactttacc    420 ggcaactgcg gcaacattct tagtggtgtt ggcccttttg catttgaaga gggtctcatc    480
```

```
ccggcgtcag tcctggcacc acttgctgca ttcgccaaga ccaacggcaa aggccgacaa      540
gacaaggtcg cactcactct tcgctgtctc aacaacaacc agctcatccg atctacattc      600
cttgttcgca atggaaagcc ggtcgaattt ggcgacgtgg tcatcgacgg tgttgcaggt      660
acaggctcgc cgatccagtt ggatttcctt gacccagcgg gcagcatgtg tacctcgctc      720
tgccccactg gcaaaccttt ggatttgctg cacatacacg gcgaagactt gccgatcgaa      780
gtatcatgcg tcgatgcagc caatccgttc gtctttgttc ggctctccga cattgatgag      840
accctgcgcg aaacgagcc agcttccgta ctggaacgcc actcggctcg cgtagagctg      900
atccgtcaag cagccgccgt cgtaatgggt cttgcacccg acacggccac tgcagcaaag      960
accaaaggca cacccaagat ctgtctggtt tccgacgcgc tccccggctc cgacgcacac     1020
gttctctcgc gaagcttcag catgggtcga ccacatcctg cattacagct ctccggtggt     1080
gtctgcctcg ctgctgcctg cagcattcca gggtcgatcc cgaaccagat tctgctcaag     1140
caaaccaaga tgatgccgga aaggctcaag ttcgcacacg catgcggtgc cattgaagct     1200
accgcggatg tcgagatgga tagcaagagc ccggttggcg tcactgtgag gagcacgagt     1260
cttttcagga ctgcaaggag actggcttct gctgaagcgt attcctctc gcctagccag     1320 tag                                                                   1323

<210> SEQ ID NO 18
<211> LENGTH: 440
<212> TYPE: PRT
<213> ORGANISM: Ustilago maydis

<400> SEQUENCE: 18

Met Leu Leu Gln Pro Thr Ser Ser Arg His Phe Glu Asp Phe Arg Tyr
1               5                   10                  15

Val Glu Pro Lys Ile Leu Thr Lys Ser Ala Leu Pro Ile Ala Pro Gly
            20                  25                  30

Ala Thr Thr Ala Gly Ala Ser Ser Lys Ser Pro Ser Phe Glu Arg
        35                  40                  45

Arg Ser Leu Arg Thr Val Ile Met Arg Ala Gly Thr Ser Lys Gly Leu
    50                  55                  60

Phe Ile Lys Ala Ser Asp Leu Pro Ser Arg Ala Glu Trp Gln Asn
65                  70                  75                  80

Ile Leu Pro Ser Ile Met Gly Ser Pro Asp Pro Phe Gly Arg Gln Leu
                85                  90                  95

Asn Gly Leu Gly Gly Gly Thr Ser Thr Thr Ser Lys Ile Ala Val Val
            100                 105                 110

Ser Gln Ser Ser Ala Pro His Ile Ala Asp Val Asp Tyr Leu Phe Ile
        115                 120                 125

Gln Cys Pro Ile Glu Gly Asp Lys Leu Asp Phe Thr Gly Asn Cys Gly
    130                 135                 140

Asn Ile Leu Ser Gly Val Gly Pro Phe Ala Phe Glu Glu Gly Leu Ile
145                 150                 155                 160

Pro Ala Ser Val Leu Ala Pro Leu Ala Ala Phe Ala Lys Thr Asn Gly
                165                 170                 175

Lys Gly Arg Gln Asp Lys Val Ala Leu Thr Leu Arg Cys Leu Asn Asn
            180                 185                 190

Asn Gln Leu Ile Arg Ser Thr Phe Leu Val Arg Asn Gly Lys Pro Val
        195                 200                 205

Glu Phe Gly Asp Val Val Ile Asp Gly Val Ala Gly Thr Gly Ser Pro
    210                 215                 220
```

```
Ile Gln Leu Asp Phe Leu Asp Pro Ala Gly Ser Met Cys Thr Ser Leu
225                 230                 235                 240

Cys Pro Thr Gly Lys Pro Leu Asp Leu Leu His Ile His Gly Glu Asp
            245                 250                 255

Leu Pro Ile Glu Val Ser Cys Val Asp Ala Ala Asn Pro Phe Val Phe
                260                 265                 270

Val Arg Leu Ser Asp Ile Asp Glu Thr Leu Arg Gly Asn Glu Pro Ala
            275                 280                 285

Ser Val Leu Glu Arg His Ser Arg Val Glu Leu Ile Arg Gln Ala
        290                 295                 300

Ala Ala Val Val Met Gly Leu Ala Pro Asp Thr Ala Thr Ala Ala Lys
305                 310                 315                 320

Thr Lys Gly Thr Pro Lys Ile Cys Leu Val Ser Asp Ala Leu Pro Gly
                325                 330                 335

Ser Asp Ala His Val Leu Ser Arg Ser Phe Ser Met Gly Arg Pro His
                340                 345                 350

Pro Ala Leu Gln Leu Ser Gly Gly Val Cys Leu Ala Ala Ala Cys Ser
            355                 360                 365

Ile Pro Gly Ser Ile Pro Asn Gln Ile Leu Leu Lys Gln Thr Lys Met
370                 375                 380

Met Pro Glu Arg Leu Lys Phe Ala His Ala Cys Gly Ala Ile Glu Ala
385                 390                 395                 400

Thr Ala Asp Val Glu Met Asp Ser Lys Ser Pro Val Gly Val Thr Val
                405                 410                 415

Arg Ser Thr Ser Leu Phe Arg Thr Ala Arg Arg Leu Ala Ser Ala Glu
            420                 425                 430

Ala Tyr Tyr Leu Ser Pro Ser Gln
        435                 440

<210> SEQ ID NO 19
<211> LENGTH: 1065
<212> TYPE: DNA
<213> ORGANISM: Ustilago maydis

<400> SEQUENCE: 19
atgtcgacaa cagagaaacg aatctcgcct tcgcccatgc actcgctgct cgccggaacc    60
atcgccggtg cggtcgaagg gtttcttact tacccgaccg agtttgtcaa gacgcaggct   120
cagcttgcct cgaatgcagc cgcaagtgcc agcaagacat gttcggtccc caagagtgtt   180
ccgggggcgg ttcgacacat ctcgtatggt gcattgccag cgcacaagct caacatcgcc   240
gccgccgccg ccgccacatc agcaccatca accactgtac cgatgccaaa gcaggcgcc   300 tcggcgatgc agattgtccg ggatacttgg aagactcgcg ggatcactgg cttcttcagc   360
ggcgcaggtg ccatggttac gggcaactct gctaaagcgg gtgttcgctt cctcacgtac   420
gatacgattc aaaaccttct gcgaccaaag tcgatcgatg caaaccagaa gctcggaatg   480
ggcagatcga tccttgccgg cttcctggct ggatcggccg aggcgatgct cgcggtcacg   540
ccttccgagg cgatcaagac acggatgatc caggattcgc tgcagcctgc tcacatgcgc   600
aagtacaaag gcgccatcga tgcggttcaa aagattgtgg cgctgagggc ttggctggt   660 ctgtacagag ggttgggtgc cacggtgctg cgacagggag caaactcatc ggtgaggttg   720
acatcctact ccatcttgaa atccgtacaa acgcaagcag gctatgccaa gtccacagca   780
gcgacattcg catcgggagc aggcgctggc ttgatcaccg tctacctcac aatgccgttt   840
```

```
gacgtggtca agacgcgaat gcaacagtca ccctcgacca caggagctac acagagcaag    900
ccgagcatcg tctcgtgcgg tctcgacatt gtcaagaggg aaggagtaaa gagcctctgg    960
aagggtacca ccccacgatt gaccaggttg attttcagcg gtggcatcgc gtttactgct   1020
tacgagacgg ttattggctg gctcaacccg accacagttg cttga                   1065
```

<210> SEQ ID NO 20
<211> LENGTH: 354
<212> TYPE: PRT
<213> ORGANISM: Ustilago maydis

<400> SEQUENCE: 20

```
Met Ser Thr Thr Glu Lys Arg Ile Ser Pro Ser Pro Met His Ser Leu
1               5                   10                  15

Leu Ala Gly Thr Ile Ala Gly Ala Val Glu Gly Phe Leu Thr Tyr Pro
            20                  25                  30

Thr Glu Phe Val Lys Thr Gln Ala Gln Leu Ala Ser Asn Ala Ala Ala
        35                  40                  45

Ser Ala Ser Lys Thr Cys Ser Val Pro Lys Ser Val Pro Gly Ala Val
    50                  55                  60

Arg His Ile Ser Tyr Gly Ala Leu Pro Ala His Lys Leu Asn Ile Ala
65                  70                  75                  80

Ala Ala Ala Ala Ala Thr Ser Ala Pro Ser Thr Thr Val Pro Met Pro
                85                  90                  95

Lys Ala Gly Ala Ser Ala Met Gln Ile Val Arg Asp Thr Trp Lys Thr
            100                 105                 110

Arg Gly Ile Thr Gly Phe Phe Ser Gly Ala Gly Ala Met Val Thr Gly
        115                 120                 125

Asn Ser Ala Lys Ala Gly Val Arg Phe Leu Thr Tyr Asp Thr Ile Gln
    130                 135                 140

Asn Leu Leu Arg Pro Lys Ser Ile Asp Ala Asn Gln Lys Leu Gly Met
145                 150                 155                 160

Gly Arg Ser Ile Leu Ala Gly Phe Leu Ala Gly Ser Ala Glu Ala Met
                165                 170                 175

Leu Ala Val Thr Pro Ser Glu Ala Ile Lys Thr Arg Met Ile Gln Asp
            180                 185                 190

Ser Leu Gln Pro Ala His Met Arg Lys Tyr Lys Gly Ala Ile Asp Ala
        195                 200                 205

Val Gln Lys Ile Val Gly Ala Glu Gly Leu Ala Gly Leu Tyr Arg Gly
    210                 215                 220

Leu Gly Ala Thr Val Leu Arg Gln Gly Ala Asn Ser Ser Val Arg Leu
225                 230                 235                 240

Thr Ser Tyr Ser Ile Leu Lys Ser Val Gln Thr Gln Ala Gly Tyr Ala
                245                 250                 255

Lys Ser Thr Ala Ala Thr Phe Ala Ser Gly Ala Gly Ala Gly Leu Ile
            260                 265                 270

Thr Val Tyr Leu Thr Met Pro Phe Asp Val Val Lys Thr Arg Met Gln
        275                 280                 285

Gln Ser Pro Ser Thr Thr Gly Ala Thr Gln Ser Lys Pro Ser Ile Val
    290                 295                 300

Ser Cys Gly Leu Asp Ile Val Lys Arg Glu Gly Val Lys Ser Leu Trp
305                 310                 315                 320

Lys Gly Thr Thr Pro Arg Leu Thr Arg Leu Ile Phe Ser Gly Gly Ile
                325                 330                 335
```

```
Ala Phe Thr Ala Tyr Glu Thr Val Ile Gly Trp Leu Asn Pro Thr Thr
        340                 345                 350

Val Ala

<210> SEQ ID NO 21
<211> LENGTH: 2868
<212> TYPE: DNA
<213> ORGANISM: Ustilago maydis

<400> SEQUENCE: 21
atgaggtgga aacaagtaca cgctgtacct ggcagtaaca cctcggacac ctcgcgtccg      60
tcgcaaggct catcggcttt ctctaccgct tgcgattttt gccgtcaccg aaagattcgt     120
tgcaatcgag aacagccatg cgacaagtgc agaagcacg gtagggccaa cacgtgtcac      180
tttgaagatg gtcgaaccaa aaagcgccaa cgcccaaaca atgcggcttg tcggcagta     240 catcaagacg aaagccgcgt tggtcagctc ggggacgagc tcgagctcga gctcgagatc     300
gcccgtgttg gtcagctttc gcgacgcca ggtcgacacg gtaatgtacg cttcaaccgc      360
gcttcatcag aggctgctgg tcaagtcagc gtggatgaag caagtcgtgt tgaagcgcac     420
aatacgtcgg gccaggctaa ggacggctca cacgcgtttg ccaatccacg gctcaacgag     480
actgcgttca gacataccgc agagacgcac catgctgctc cagtagccca cggacgtg      540 cgtgcatcgt ctgtatcatg ctcgtcgctg aatgctgcag tgcggcctca cagctcgtca     600
cctctgccga cttcgccaac ttcgtcggcg gtcgctagca tcattgcgga tctgggcgat     660
ccgaggcatt caatcggaca tgctgaacgg acgcgcgcct ctgcgtcacc cagccagcaa     720
gctacacgtg gagtcatgtc aaatctgcgc gtcaacaatc gaggcgaatc gcgataccac     780
ggtccgacga gtgcttcgtt caacgcgcct gaagcattga gcgaggattc tcgagctgga     840
attgcgtctg cgcagggccg tctcagtgtg gatggtggcg gtggcgccaa tccagcaggt     900
ggtagtcaag agcagcgtgt ctcgctggat gcagccgtgc tcaccgacag attgacatcg     960
ctggctgctc gcgaaagaca ggaagaggtg atgaacgttg tcgctggcag actcgacttt    1020
gacggtgtag agcctgagct ggcgatccac ctgctcaact tgcactggaa tcggcagcat    1080
cacgcctacc tggtcacgta ccgaccgctg ttcatgcggg atatggcggc tcctccaggc    1140
aaagcaaagt acttttccaa gctactcttc cacgctatcc tgttcggtgc cgccaagttt    1200
tcagaccgca tcaatcaggt caggtcagac gtcaatgatc cctcgacggc tggccaacag    1260
tttctcgaac gcgtccagca actgttacca gaagcgttga tcaagagccg catcacgacg    1320
gtgcaagcgt tgctgttact cgcatgcacg cactatgccc gtggtagcga gagtgcagct    1380
tggctacatt ccggattggc tttccgcatg gcgatcgatc tggggatgaa cgaagatagt    1440
atcgagctgg ttcatcgggg caacatggca ctcgaggagc tcgagcttcg tcgacgtgta    1500
gtatgggccg cgtttgtgat tgacaagatc cactcgctct accaaggtcg gcaggcttcg    1560
attgaacggc gcaacctgta tgtgcccatc gagttccacg accatttcga agagaccgag    1620
ttctggacgc ctgttgcgtt tcaccgacct ctgagcgagg cagaggcgca aagcaaagct    1680
acagccagag gcaccaacgc cgccactccg agtggctaca cgggaccgat ctacagtgtt    1740
tctacgtttg ccgagctgtg caggctgacg gtgattatga aaaagatcat ccagatcttc    1800
tattcgatcg atagcggtgc gcgatccgaa agagcacaaa cggaacactt gattgaaatg    1860
cgctccgagc tcgccgcttg gcgcacgtcg ttgcctgcac atctgcgtat cgactcgagc    1920
tcgccagcag gtagaagtgg cggccaacgc tctcgcactt gcccgcccaa tctgatctcg    1980
```

```
ttgcacgcac tctatcatgc gttgacgatc ctgctgaatc gaccattcct accacatgga      2040
catcttcgca gcgacgatgc agcttgcggc agatcgtcat ggaaagcatg cgtggatgca      2100
gcgtcgagca tctcgagcct catgaatctg tatcgtcaga cggtgagcat gaagggagcg      2160
ccgcagctca tctcatacat caacttttgt gctgcaggaa ttcacgttcg tgtagcagca      2220
cagctgcaac agtccaacac gtcgagcgaa ggtgctaatc tggcagccgc atccagtcgc      2280
agatacgagc tgaaagcgct ccgacaatgc ctgcaggatt tcgaggagaa tcaagatccc      2340
aacccgggcg tcgctaaagc caagagtgtg atccgcaaca tggccgagag agctggcatt      2400
ctcaacctgc ttcaagacga ctcgggagaa ggtggattgt cgccgatcaa ccaagatgac      2460
agtccaccgc tgatgaatct cgtcggccac agtggtagcc aagcgaatcg aggggtgct       2520 gcaaatcgcg tcgagcttgt tggagcaagc gcacttgcac gccatgcgag cgcgctgtcc      2580
atgacaacac cgtcgtcctc gacttcgatc gccgcagcag gaggagcaac agccgcatca      2640
gcagcgttga atcgagtaga cgcagcgcag aactcaactt ctgcactcac accgccctac      2700
gagatcgact ttgaaagcat tctcgcctcg tttgatcact tgagtccgc agccggtcct       2760 ggtcgagacg gcctattcgc aacaggcaca gcggatccca acaccaactc ggacattctc      2820
tttggctttc ttcgtgacta tgatgcaccc tctgccctct cgctatga                  2868
```

<210> SEQ ID NO 22
<211> LENGTH: 955
<212> TYPE: PRT
<213> ORGANISM: Ustilago maydis

<400> SEQUENCE: 22

```
Met Arg Trp Lys Gln Val His Ala Val Pro Gly Ser Asn Thr Ser Asp
1               5                   10                  15

Thr Ser Arg Pro Ser Gln Gly Ser Ser Ala Phe Ser Thr Ala Cys Asp
            20                  25                  30

Phe Cys Arg His Arg Lys Ile Arg Cys Asn Arg Glu Gln Pro Cys Asp
        35                  40                  45

Lys Cys Gln Lys His Gly Arg Ala Asn Thr Cys His Phe Glu Asp Gly
    50                  55                  60

Arg Thr Lys Lys Arg Gln Arg Pro Asn Asn Ala Ala Cys Ala Ala Val
65                  70                  75                  80

His Gln Asp Glu Ser Arg Val Gly Gln Leu Gly Asp Glu Leu Glu Leu
                85                  90                  95

Glu Leu Glu Ile Ala Arg Val Gly Gln Leu Ser Ala Thr Pro Gly Arg
            100                 105                 110

His Gly Asn Val Arg Phe Asn Arg Ala Ser Glu Ala Ala Gly Gln
        115                 120                 125

Val Ser Val Asp Glu Ala Ser Arg Val Glu Ala Asn Thr Ser Gly
    130                 135                 140

Gln Ala Lys Asp Gly Ser His Ala Phe Ala Asn Pro Arg Leu Asn Glu
145                 150                 155                 160

Thr Ala Phe Arg His Thr Ala Glu Thr His His Ala Ala Pro Val Ala
                165                 170                 175

His Thr Asp Val Arg Ala Ser Ser Val Ser Cys Ser Ser Leu Asn Ala
            180                 185                 190

Ala Val Arg Pro His Ser Ser Pro Leu Pro Thr Ser Pro Thr Ser
        195                 200                 205

Ser Ala Val Ala Ser Ile Ile Ala Asp Leu Gly Asp Pro Arg His Ser
    210                 215                 220
```

```
Ile Gly His Ala Glu Arg Thr Arg Ala Ser Ala Ser Pro Ser Gln Gln
225                 230                 235                 240

Ala Thr Arg Gly Val Met Ser Asn Leu Arg Val Asn Asn Arg Gly Glu
            245                 250                 255

Ser Arg Tyr His Gly Pro Thr Ser Ala Ser Phe Asn Ala Pro Glu Ala
                260                 265                 270

Leu Ser Glu Asp Ser Arg Ala Gly Ile Ala Ser Ala Gln Gly Arg Leu
            275                 280                 285

Ser Val Asp Gly Gly Gly Ala Asn Pro Ala Gly Gly Ser Gln Glu
        290                 295                 300

Gln Arg Val Ser Leu Asp Ala Ala Val Leu Thr Asp Arg Leu Thr Ser
305                 310                 315                 320

Leu Ala Ala Arg Glu Arg Gln Glu Glu Val Met Asn Val Val Ala Gly
                325                 330                 335

Arg Leu Asp Phe Asp Gly Val Glu Pro Glu Leu Ala Ile His Leu Leu
                340                 345                 350

Asn Leu His Trp Asn Arg Gln His Ala Tyr Leu Val Thr Tyr Arg
                355                 360                 365

Pro Leu Phe Met Arg Asp Met Ala Ala Pro Gly Lys Ala Lys Tyr
370                 375                 380

Phe Ser Lys Leu Leu Phe His Ala Ile Leu Phe Gly Ala Ala Lys Phe
385                 390                 395                 400

Ser Asp Arg Ile Asn Gln Val Arg Ser Asp Val Asn Asp Pro Ser Thr
                405                 410                 415

Ala Gly Gln Gln Phe Leu Glu Arg Val Gln Gln Leu Leu Pro Glu Ala
            420                 425                 430

Leu Ile Lys Ser Arg Ile Thr Thr Val Gln Ala Leu Leu Leu Leu Ala
            435                 440                 445

Cys Thr His Tyr Ala Arg Gly Ser Glu Ser Ala Ala Trp Leu His Ser
            450                 455                 460

Gly Leu Ala Phe Arg Met Ala Ile Asp Leu Gly Met Asn Glu Asp Ser
465                 470                 475                 480

Ile Glu Leu Val Ala Ser Gly Asn Met Ala Leu Glu Glu Leu Glu Leu
                485                 490                 495

Arg Arg Arg Val Val Trp Ala Ala Phe Val Ile Asp Lys Ile His Ser
            500                 505                 510

Leu Tyr Gln Gly Arg Gln Ala Ser Ile Glu Arg Arg Asn Leu Tyr Val
            515                 520                 525

Pro Ile Glu Phe His Asp His Phe Glu Thr Glu Phe Trp Thr Pro
530                 535                 540

Val Ala Phe His Arg Pro Leu Ser Glu Ala Glu Ala Gln Ser Lys Ala
545                 550                 555                 560

Thr Ala Arg Gly Thr Asn Ala Ala Thr Pro Ser Gly Tyr Thr Gly Pro
            565                 570                 575

Ile Tyr Ser Val Ser Thr Phe Ala Glu Leu Cys Arg Leu Thr Val Ile
            580                 585                 590

Met Glu Lys Ile Ile Gln Ile Phe Tyr Ser Ile Asp Ser Gly Ala Arg
            595                 600                 605

Ser Glu Arg Ala Gln Thr Glu His Leu Ile Glu Met Arg Ser Glu Leu
            610                 615                 620

Ala Ala Trp Arg Thr Ser Leu Pro Ala His Leu Arg Ile Asp Ser Ser
625                 630                 635                 640
```

```
Ser Pro Ala Gly Arg Ser Gly Gly Gln Arg Ser Arg Thr Cys Pro Pro
                645                 650                 655

Asn Leu Ile Ser Leu His Ala Leu Tyr His Ala Leu Thr Ile Leu Leu
            660                 665                 670

Asn Arg Pro Phe Leu Pro His Gly His Leu Arg Ser Asp Asp Ala Ala
        675                 680                 685

Cys Gly Arg Ser Ser Trp Lys Ala Cys Val Asp Ala Ala Ser Ser Ile
    690                 695                 700

Ser Ser Leu Met Asn Leu Tyr Arg Gln Thr Val Ser Met Lys Gly Ala
705                 710                 715                 720

Pro Gln Leu Ile Ser Tyr Ile Asn Phe Cys Ala Ala Gly Ile His Val
                725                 730                 735

Arg Val Ala Ala Gln Leu Gln Gln Ser Asn Thr Ser Ser Glu Gly Ala
            740                 745                 750

Asn Leu Ala Ala Ala Ser Ser Arg Arg Tyr Glu Leu Lys Ala Leu Arg
        755                 760                 765

Gln Cys Leu Gln Asp Phe Glu Glu Asn Gln Asp Pro Asn Pro Gly Val
    770                 775                 780

Ala Lys Ala Lys Ser Val Ile Arg Asn Met Ala Glu Arg Ala Gly Ile
785                 790                 795                 800

Leu Asn Leu Leu Gln Asp Asp Ser Gly Glu Gly Leu Ser Pro Ile
                805                 810                 815

Asn Gln Asp Asp Ser Pro Pro Leu Met Asn Leu Val Gly His Ser Gly
            820                 825                 830

Ser Gln Ala Asn Arg Gly Gly Ala Ala Asn Arg Val Glu Leu Val Gly
        835                 840                 845

Ala Ser Ala Leu Ala Arg His Ala Ser Ala Leu Ser Met Thr Thr Pro
    850                 855                 860

Ser Ser Ser Thr Ser Ile Ala Ala Gly Gly Ala Thr Ala Ala Ser
865                 870                 875                 880

Ala Ala Leu Asn Arg Val Asp Ala Ala Gln Asn Ser Thr Ser Ala Leu
                885                 890                 895

Thr Pro Pro Tyr Glu Ile Asp Phe Glu Ser Ile Leu Ala Ser Phe Asp
            900                 905                 910

His Phe Glu Ser Ala Ala Gly Pro Gly Arg Asp Gly Leu Phe Ala Thr
        915                 920                 925

Gly Thr Ala Asp Pro Asn Thr Asn Ser Asp Ile Leu Phe Gly Phe Leu
    930                 935                 940

Arg Asp Tyr Asp Ala Pro Ser Ala Leu Ser Leu
945                 950                 955

<210> SEQ ID NO 23
<211> LENGTH: 365
<212> TYPE: PRT
<213> ORGANISM: Pseudogulbenkiania sp. NH8B

<400> SEQUENCE: 23

Met Leu Thr Pro Ile Pro Cys Leu Leu Met Arg Gly Gly Thr Ser Lys
1               5                   10                  15

Gly Pro Phe Phe Leu Ala Asp Asp Leu Pro Ala Asp Pro Glu Thr Arg
            20                  25                  30

Asn Ala Val Leu Leu Ser Val Met Gly Ser Pro Asp Leu Arg Gln Ile
        35                  40                  45

Asp Gly Ile Gly Gly Gly Asp Ser Leu Thr Ser Lys Val Ala Ile Val
    50                  55                  60
```

-continued

```
Ser Arg Ser Gln Arg Pro Gly Ile Asp Val Asp Tyr Leu Phe Ala Gln
 65                  70                  75                  80

Val Ser Val Ser Gln Arg Ala Val Asp Thr Asn Pro Asn Cys Gly Asn
                 85                  90                  95

Met Leu Ser Gly Val Gly Pro Phe Ala Ile Glu Gln Gly Leu Val Pro
            100                 105                 110

Ala Thr Asp Pro Val Thr Pro Val Arg Ile Phe Asn Val Asn Thr Gly
        115                 120                 125

Lys Val Ile Glu Ala Leu Val Pro Thr Pro Ser Gly Glu Val Thr Tyr
    130                 135                 140

Glu Gly Glu Val His Ile Asp Gly Val Pro Gly Ala Ala Ala Gly Ile
145                 150                 155                 160

Val Leu Asn Phe Leu Asp Ala Ala Gly Ala Lys Thr Gly Lys Leu Leu
                165                 170                 175

Pro Thr Gly Gln Ala Leu Asp Ile Val Asp Gly Ile Ala Val Ser Cys
            180                 185                 190

Val Asp Phe Ser Thr Pro Ile Val Leu Val Ala Ala Asp Leu Gly
        195                 200                 205

Ile Ser Gly His Glu Ser Lys Ala Glu Leu Asp Ala Asn Gly Ala Leu
    210                 215                 220

Leu Ala Arg Leu Glu Val Val Arg Gln Ala Ala Arg Arg Met Gly
225                 230                 235                 240

Leu Gly Asp Val Ser Ala Ser Val Leu Pro Lys Ile Ala Val Leu Ala
                245                 250                 255

Ala Pro Ala Lys Asp Gly Ser Ile Ser Ser Arg Tyr Phe Thr Pro Trp
            260                 265                 270

Ala Cys His Ala Ala His Ala Val Thr Gly Ala Leu Cys Val Ala Ala
            275                 280                 285

Ala Cys Leu Ile Pro Gly Ser Val Ala Ser Arg Leu Val Arg Ser Arg
        290                 295                 300

Ala Asp Gln Pro Asp Arg Ile Ala Ile Glu His Pro Ser Gly Gln Leu
305                 310                 315                 320

Glu Thr Gln Val Asp Leu Gln Ala Ala Pro Ala Gly Glu Pro Pro Val
                325                 330                 335

Ile Arg Arg Val Gly Ile Val Arg Thr Ala Arg Pro Leu Phe Ser Gly
            340                 345                 350

Gln Val Leu Ile Pro Gly Thr Val Trp Lys Lys Ala Gly
        355                 360                 365
```

<210> SEQ ID NO 24
<211> LENGTH: 9
<212> TYPE: PRT
<213> ORGANISM: Artificial Sequence
<220> FEATURE:
<223> OTHER INFORMATION: FLAG protein

<400> SEQUENCE: 24

```
Asp Tyr Lys Asp Asp Asp Asp Lys Gly
 1               5
```

<210> SEQ ID NO 25
<211> LENGTH: 10
<212> TYPE: PRT
<213> ORGANISM: T7 phage

<400> SEQUENCE: 25

```
Ala Ser Met Thr Gly Gly Gln Gln Met Gly
1               5                   10

<210> SEQ ID NO 26
<211> LENGTH: 11
<212> TYPE: PRT
<213> ORGANISM: Human herpesvirus 1

<400> SEQUENCE: 26

Gln Pro Glu Leu Ala Pro Glu Asp Pro Glu Asp
1               5                   10

<210> SEQ ID NO 27
<211> LENGTH: 11
<212> TYPE: PRT
<213> ORGANISM: Vesicular Stomatitis Virus

<400> SEQUENCE: 27

Tyr Thr Asp Ile Glu Met Asn Arg Leu Gly Lys
1               5                   10

<210> SEQ ID NO 28
<211> LENGTH: 9
<212> TYPE: PRT
<213> ORGANISM: Influenza A virus

<400> SEQUENCE: 28

Tyr Pro Tyr Asp Val Pro Asp Tyr Ala
1               5

<210> SEQ ID NO 29
<211> LENGTH: 10
<212> TYPE: PRT
<213> ORGANISM: human

<400> SEQUENCE: 29

Glu Gln Lys Leu Ile Ser Glu Glu Asp Leu
1               5                   10

<210> SEQ ID NO 30
<211> LENGTH: 6
<212> TYPE: PRT
<213> ORGANISM: Artificial Sequence
<220> FEATURE:
<223> OTHER INFORMATION: His-Tag

<400> SEQUENCE: 30

His His His His His His
1               5

<210> SEQ ID NO 31
<211> LENGTH: 903
<212> TYPE: DNA
<213> ORGANISM: Ustilago maydis

<400> SEQUENCE: 31
agcttgcatg cctgcaggtc gaaattcgag ctcggtaccc gtaccgagct cgactttcac      60
ttttctctat cactgatagg gagtggtaaa ctcgactttc attttctcta tcactgatag     120
ggagtggtaa actcgacttt cacttttctc tatcactgat agggagtggt aaactcgact     180 ttcactttc tctatcacgg atagggagtg taaactcga ctttcacttt tctctatcac      240 tgataggag tggtaaactc gactttcact tttctctatc actgataggg agtggtaaac     300
tcgactttca cttttctcta tcactgatag ggagtggtaa actcgagtac cgagctcgac     360
```

```
tttcactttt  ctctatcact  gatagggagt  ggtaaactcg  actttcattt  tctctatcac    420
tgatagggag  tggtaaactc  gactttcact  tttctctatc  actgataggg  agtggtaaac    480
tcgactttca  cttttctcta  tcacggatag  ggagtggtaa  actcgacttt  cacttttctc    540
tatcactgat  agggagtggt  aaactcgact  ttcactttc   tctatcactg  atagggagtg    600
gtaaactcga  ctttcacttt  tctctatcac  tgatagggag  tggtaaactc  gaggggatca    660
attcgaccaa  tgaggcgcga  gacgagggga  cgctggaagt  tgaggcgcaa  gaaaattttt    720
ctctggttct  gcgcggcaga  gacgaccaga  ttcgcccgct  ttcttctgcg  ttgggtgcct    780
cttttgggtg  ccagactttg  tgtgtgcgcc  agcgagacgt  tccaataaag  ggcgctgtct    840
cggcactatc  tttctttctt  tcctcataca  tcgtatcata  ccatacacag  acaacatcat    900
cca                                                                      903
```

MEANS AND METHODS FOR ITACONIC ACID PRODUCTION

CROSS-REFERENCE TO RELATED APPLICATIONS

This application is the U.S. national phase application filed under 35 U.S.C. § 371 claiming benefit to International Patent Application No. PCT/EP2015/055976, filed Mar. 20, 2015, which is entitled to priority to LU 92 409, filed Mar. 21, 2014, each of which application is hereby incorporated herein by reference in its entirety.

FIELD OF THE INVENTION

The present invention relates to a method of producing itaconic acid. Further the present invention relates to nucleic acids encoding an aconitate-delta-isomerase (ADI) and a trans-aconitate decarboxylase (TAD) and uses of such nucleic acids. Provided is additionally a recombinant host cell engineered to overexpress nucleic acids of the present invention. Furthermore an expression cassette and a vector are provided which include the respective nucleic acid.

BACKGROUND OF THE INVENTION

Methylenesuccinic acid (CAS number: 97-65-4), known as itaconic acid (ITA) and also called butanedioic acid, methylene—is a promising new platform compound for production of biofuels, chemical compounds, including e.g. detergents, and polymers, including plastics and artificial glass. ITA has been identified by the US Department of Energy as one of the top 12 bio-based chemical building blocks (Werpy, T, and Petersen, G, Top Value Added Chemicals from Biomass Volume I, Results of Screening for Potential Candidates from Sugars and Synthesis Gas. Technical report, U.S. Department of Energy, 2004, available at http://www.osti.gov/bridge/). Over 80000 tons per year are produced, mostly for the production of polymers (Okabe et al., Appl Microbiol Biotechnol (2009) 84, 597-606; Dwiarti, L, et al., Bioresour Technol. (2007) 98, 17, 3329-3337). ITA can for example be used in the manufacture of acrylic latexes, plasticizer, additives, adhesives, emulsifying agents, paint chemicals, textile and paper.

Currently, most ITA is produced by fermentation of *Aspergillus* strains (Okabe 2009, supra; Willke T, and Vorlop K. D., Appl Microbiol Biotechnol. (2001) 56, 3-4, 289-295; U.S. Pat. No. 2,385,283A). The parameters of ITA production using this fungus have been investigated (Willke, 2001, supra; Okabe 2009, supra), and the biochemical production route has been extensively studied (Bonnarme, P, et al., Journal of Bacteriology (1995) 177, 12, 3573-3578; Bentley, R, and Thiessen, C. P., J Biol Chem. (1957) 226, 2, 673-687; Bentley, R, and Thiessen, C. P., J Biol Chem. (1957) 226, 2, 689-701; Bentley, R, Thiessen, C. P., J Biol Chem. (1957) 226, 2, 703-720; Kanamasa, S, et al., Appl Microbiol Biotechnol. (2008) 80, 2, 223-229). In short, in *Aspergillus terreus*, the substrate (i.e. glucose) is converted to the primary metabolite cis-aconitate through glycolysis and the TCA cycle (tricarboxylic acid cycle). Cis-aconitate is subsequently decarboxylated by the enzyme cis-aconitate decarboxylase (CAD), to yield ITA and $CO_2$. The identification of the CAD enzyme and especially its corresponding gene sequence has led to a wide range of metabolic engineering opportunities, which is rapidly expanding (e.g. Dwiarti, L, et al., J Biosci Bioeng. (2002) 94, 1, 29-33; Kanamasa et al., 2008, supra; WO 2009/014437 A1, US 2010/330632 A1, US 2010/285546 A1, US 2011/053232 A1). Alternative hosts for the production of ITA are available, such as strains of *Rhodotorula, Candida* and *Ustilago* (Willke, 2001, supra). Nevertheless, up to date virtually nothing is known about how these alternative hosts produce ITA.

ITA production with *Aspergillus* strains has been well characterized (WO 2009/014437 A1, WO 2009/104958 A1, WO 2009/110796 A1). Further, *Ustilago* strains have been used for ITA production (JP55034017A, JP3035785A, Willke, 2001, supra).

There are several disadvantages related to fermentation of filamentous fungi in general, and with *Aspergillus terreus* specifically (Willke, 2001, supra). Filamentous fungi are particularly problematic in that their morphology can be difficult to be controlled in fermentation systems.

*Ustilago* strains that are presently applied for the production of itaconic acid are uncharacterized and thus are not amenable without undue efforts to modifications and improvements. Moreover, these strains produce itaconic acid under natural conditions, i.e. regulatory elements of genes involved in the biosynthesis of itaconic acid may be subject to feedback inhibition or end product inhibition, thereby limiting the spectrum of such strains for permanent itaconic acid production.

It is therefore an object of the present invention to offer alternative means and methods of obtaining ITA. It would be desirable if such alternative means and methods could provide a way of obtaining ITA in high yield.

This object is solved by providing the claimed subject matter and the embodiments and aspects which follow.

SUMMARY OF THE INVENTION

The present invention is based on the elucidation of the biosynthesis pathway of itaconic acid production in *Ustilago maydis*. Though at first glance, the elucidation of said biosynthetic pathway may appear to be a straightforward matter, since *Ustilago maydis* is known to produce itaconic acid. However, while a knock-out of the key enzyme of itaconic acid, i.e., cis-aconitate decarboxylase (CAD) which converts cis-aconitate into itaconic acid, results in a complete abolishment of itaconic acid in presently applied host cells such as *Aspergillus* sp., a knock-out of the gene encoding a protein with sequence similarity to CAD in *Ustilago maydis* does not abolish itaconic acid production. Thus, it is apparent that *Ustilago maydis* must have a different pathway. This different pathway was elucidated by the present inventors. In particular, rather than using CAD as the key enzyme in itaconic acid production, *Ustilago maydis* uses an aconitate-delta-isomerase (ADI), which converts cis-aconitate into trans-aconitate, which is further converted into itaconic acid by the action of a trans-aconitate decarboxylase (TAD) (see FIG. 14). Thus, in *Ustilago maydis*, two enzymes are required for itaconic acid production. These two enzymes have, to the best of the inventors' knowledge, no known homolog among the usual itaconic acid production hosts. This is an unusual and thus surprising finding and shows that inventive efforts were required to figure out that two enzymes are necessary, since neither, e.g., a standard complementation assay of mutants nor protein identification based on the available genome from *Ustilago maydis* would have led to success.

Moreover, in accordance with data retrieved from knock-out and over-expression strains, the present inventors concluded that in the biosynthesis of itaconic acid, cis-aconitate, or a precursor thereof, is exported from the mitochondria into the cytosol by the mitochondrial transporter CTP1. In the cytosol, cis-aconitate is the substrate of ADI, which catalyzes isomerization to trans-aconitate. TAD uses trans-aconitate as a substrate for decarboxylation to itaconic acid. Finally, itaconic acid is exported by a transporter of the major facilitator superfamily (MFS). Hence, in accordance with this model the itaconic acid biosynthesis route in *Ustilago maydis* deviates fundamentally from that in, e.g., *Aspergillus terreus*—a well-known and used working horse for the production of itaconic acid. In *Aspergillus terreus* cis-aconitate decarboxylase (CAD) is solely responsible for itaconic acid biosynthesis by catalyzing a decarboxylation of cis-aconitate, while *Ustilago maydis* has two key enzymes, i.e., ADI and TAD.

The above being said, the present invention is broadly applicable to host cells and not limited to *Ustilago maydis*, since the present inventors showed that the expression of TAD and ADI in the baker's yeast *Saccharomyces cerevisiae* results in itaconic acid production, while *S. cerevisiae* is otherwise not capable of producing itaconic acid. This result demonstrates that ADI and TAD are functional in a heterologous host cell and are indeed the key players in the synthesis of itaconic acid. Moreover, given the fact that baker's yeast does not at all have homologs to TAD and ADI from *Ustilago maydis*, it is fully reasonable that TAD and ADI, when expressed in an microorganism otherwise incapable of producing itaconic acid, are functional and can thus convey to such an organism the capability to produce itaconic acid.

Accordingly, in a first aspect the present invention relates to a method of producing itaconic acid, comprising
(a) culturing a recombinant host cell which is engineered to overexpress
  (i) a polynucleotide sequence having at least 30%, 40%, or 50% sequence identity with the sequence of SEQ ID NO: 1, said polynucleotide sequence encoding a protein or fragment thereof having aconitate-delta-isomerase (ADI) activity; and/or
  (ii) a polynucleotide sequence having at least 50% sequence identity with the sequence of SEQ ID NO: 6, said polynucleotide sequence encoding a protein or fragment thereof having trans-aconitate decarboxylase (TAD) activity,
  under conditions to allow said host cell to overexpress said polynucleotide sequence (i) and (ii), thereby said host cell is capable of converting cis-aconitate via trans-aconitate to itaconic acid; and
(b) obtaining itaconic acid.
TAD and ADI activity can preferably be determined as described in the appended Examples.

As mentioned before, the present invention is, inter alia, based on the identification of an aconitate-delta-isomerase (ADI) enzyme and a trans-aconitate decarboxylase (TAD) enzyme, which together compose the biochemical pathway for ITA production in *Ustilago maydis*. Although *U. maydis* possesses a gene encoding an enzyme with low similarity to the *A. terreus* CAD (UM06344 on the genome of *U. maydis* 521, 23% similarity to *A. terreus* CAD), disruption of this gene in *U. maydis* does not affect ITA production. Instead, two genes encoded by the loci UM11778 and UM05076 on the genome of *U. maydis* 521 were found to be essential for ITA production. Disruption of either of these genes led to a drastic decrease of ITA production. Without being bound by any particular theory, UM11778 is believed to encode the enzyme aconitate-delta-isomerase (ADI). UM05076 is believed to encode the enzyme trans-aconitate decarboxylase (TAD). The amino acid sequence of neither of these enzymes has any apparent similarity to the CAD enzyme of *A. terreus*. An alternative pathway to produce itaconic acid was therefore discovered by the present inventors. In a first step, cis-aconitate will be converted into trans-aconitate by the ADI. The so-produced trans-aconitate is then converted into itaconate (itaconic acid) by the TAD. This principle can also be seen in the examples. Of course, this principle can also be expanded to other fungi and yeasts, as shown in the examples.

Itaconic acid is a top-value biobased chemical building block used for the production of polymers, pharmaceuticals and fuels. Itaconic acid is currently produced via fermentation of the filamentous ascomycete *Aspergillus terreus*. Biosynthesis of itaconic acid in *A. terreus* occurs by decarboxylation of cis-aconitate, a common intermediate of the citric acid cycle. Itaconic acid production has been observed also in other fungal species but its biosynthetic routes have not been elucidated. The present inventors show that the basidiomycetous yeast *Ustilago maydis* uses an alternative biosynthesis pathway to produce itaconic acid. In this fungus, itaconic acid is generated by decarboxylation of trans-aconitate. This unusual substrate is generated in the cytoplasm by isomerization of cis-aconitate. All genes required for itaconic acid production and secretion are arranged in a single gene cluster in the *U. maydis* genome. The present inventors have characterized in vitro both trans-aconitate decarboxylase (TAD) and aconitate-delta-isomerase (ADI). They were also able to reconstitute itaconic acid production in the yeast *Saccharomyces cerevisiae* by expression of these two enzymes. This shows that at least TAD and ADI, when expressed in a heterologous host cell, are sufficient to produce itaconic acid. Hence, it is plausible and reasonable that a host cell equipped with genes encoding TAD and/or ADI is able to produce itaconic acid. The identification of an alternative route for itaconic acid production will help to improve both yield and application potential of this interesting biobased chemical building block, since the elucidation of the alternative route will allow a targeted manipulation of the enzymes that are correlated in this pathway. For example, any feedback inhibition or the like could be prevented and proteins could be massively overexpressed. In addition, the yeast-like growing fungus *U. maydis* might be a more suitable production strain for e.g. large-scale submerged fermentation.

In some embodiments, in the method of the present invention said host cell further overexpresses a polynucleotide sequence having at least 50% sequence identity with the sequence of SEQ ID NO: 4, said polynucleotide sequence encoding a protein or fragment thereof having the activity of a mitochondrial citrate transporter, preferably of a mitochondrial cis-aconitate transporter.

In further embodiments, in the method of the present invention said host cell further overexpresses a polynucleotide sequence having at least 50% sequence identity with the sequence of SEQ ID NO: 3, said polynucleotide sequence encoding a protein or fragment thereof having the activity of a multidrug transporter of the major facilitator superfamily, preferably of a transporter which exports itaconic acid or itaconate, respectively, out of the host cell.

In some embodiments, in the method of the present invention said host cell further overexpresses a polynucleotide sequence having at least 50% sequence identity with the sequence of SEQ ID NO: 8, said polynucleotide sequence encoding a protein or fragment thereof having the activity of a transcription factor for at least one of polynucleotide sequences of any one of SEQ ID NOs: 1, 3, 4, and/or 6.

In further embodiments, in the method of the present invention at least one of the polynucleotide sequences of any of the SEQ ID NO: 1, 3, 4, 6, and/or 8 is overexpressed in comparison to a host cell prior to engineering.

In other embodiments, in the method of the present invention overexpression is achieved by using a recombinant promoter, which drives expression of said polynucleotide(s) in said host cell. The overexpression can be achieved by expressing 2, 3, 4 or more copies of said polynucleotide(s) in said host cell.

In some embodiments, in the method of the present invention said polynucleotide is integrated in the genome of said host cell. The integration can be ectopically or in the natural locus. The overexpression can be achieved by using an enhancer to express the polynucleotide.

In further embodiments, in the method of the present invention said polynucleotide, when overexpressed in said host cell results in production of itaconic acid of 2 g/L or more after 48 h culture in comparison to a host cell prior to engineering.

In some embodiments, in the method of the present invention said host cell is engineered to underexpress a polynucleotide sequence having at least 50% sequence identity with the sequence of SEQ ID NO: 9, said polynucleotide sequence encoding a protein or fragment thereof having the activity of a cytochrome P450 monooxygenase. In some embodiments, the underexpression in said host cell results in production of itaconic acid of 2 g/L or more after 48 h culture in comparison to a host cell prior to engineering.

In other embodiments, in the method of the present invention said polynucleotide sequence is a heterologous polynucleotide sequence.

In some embodiments, in the method of the present invention said host cell is a cell of a fungus or a yeast, preferably said cell of a fungus is a cell from *Ustilago maydis, Aspergillus terreus* or *Saccharomyces cerevisiae*.

In further embodiments, the method of the present invention further comprises providing the host cell with a suitable carbon source. Preferably, the carbon source comprises at least one of a monosaccharide, a polysaccharide, a lipid and a fatty acid. Preferably, the monosaccharide is one of mannose, glucose, arabinose and xylose. Preferably, the polysaccharide is one of starch, a mannan and cellulose. Preferably, the lipid is triacylglycerol.

In some embodiments, the method of the present invention further comprises isolating itaconic acid from the medium in which the host cell is cultured.

In a further aspect, the present invention relates to a recombinant host cell which is engineered to overexpress
(i) a polynucleotide sequence having at least 30%, 40%, or 50% sequence identity with the sequence of SEQ ID NO: 1, said polynucleotide sequence encoding a protein or fragment thereof having aconitate-delta-isomerase (ADI) activity; and
(ii) a polynucleotide sequence having at least 50% sequence identity with the sequence of SEQ ID NO: 6, said polynucleotide sequence encoding a protein or fragment thereof having trans-aconitate decarboxylase (TAD) activity.

In some embodiments, the recombinant host cell of the present invention comprises a host cell further overexpressing at least one polynucleotide sequence having at least 50% sequence identity with the SEQ ID NO: 4, said polynucleotide sequence encoding a protein or fragment thereof having the activity of a mitochondrial citrate transporter, preferably of a mitochondrial cis-aconitate transporter and/or a polynucleotide sequence having at least 50% sequence identity with the sequence of SEQ ID NO: 3, said polynucleotide sequence encoding a protein or fragment thereof having the activity of a multidrug transporter of the major facilitator superfamily, preferably of a transporter which exports itaconic acid out of the host cell, and/or a polynucleotide sequence having at least 50% sequence identity with the sequence of SEQ ID NO: 8, said polynucleotide sequence encoding a protein or fragment thereof having the activity of a transcription factor for at least one of polynucleotide sequences of any one of SEQ ID NOs: 1, 3, 4, and/or 6.

In some embodiments, the recombinant of the present invention comprises a host cell further underexpressing a polynucleotide sequences having at least 50% sequence identity with the sequence of SEQ ID NO: 9, said polynucleotide sequence encoding a protein or fragment thereof having the activity of a cytochrome P450 monooxygenase.

In another aspect the present invention relates to a nucleic acid molecule comprising a polynucleotide sequence selected from
(a) a polynucleotide sequence having at least 30%, 40%, or 50% sequence identity with the sequence of SEQ ID NO: 1, said polynucleotide sequence encoding a protein or fragment thereof having aconitate-delta-isomerase (ADI) activity;
(b) a polynucleotide sequence having at least 50% sequence identity with the sequence of SEQ ID NO: 3, said polynucleotide sequence encoding a protein or fragment thereof having the activity of a multidrug transporter of the major facilitator superfamily, preferably of a transporter which exports itaconic acid out of the host cell;
(c) a polynucleotide sequence having at least 50% sequence identity with the sequence of SEQ ID NO: 4, said polynucleotide sequence encoding a protein or fragment thereof having the activity of a mitochondrial citrate transporter, preferably of a mitochondrial cis-aconitate transporter,
(d) a polynucleotide sequence having at least 50% sequence identity with the sequence of SEQ ID NO: 6, said polynucleotide sequence encoding a protein or fragment thereof having trans-aconitate decarboxylase (TAD) activity;
(e) a polynucleotide sequence having at least 50% sequence identity with the sequence of SEQ ID NO: 8, said polynucleotide sequence encoding a protein or fragment thereof having the activity of a transcription factor for at least one of polynucleotide sequences of any one of SEQ ID NOs: 1, 3, 4, and/or 6.

In some embodiments the nucleic acid of the present invention is a nucleic acid molecule, wherein
(i) the polynucleotide sequence of (a) as described above is not the polynucleotide sequence having accession number UM11778 in MUMDB
(ii) the polynucleotide sequence of (b) as described above is not the polynucleotide sequence having accession number UM11777 in MUMDB
(iii) the polynucleotide sequence of (c) as described above is not the polynucleotide sequence having accession number UM05079 in MUMDB
(iv) the polynucleotide sequence of (d) as described above is not the polynucleotide sequence having accession number UM05076 in MUMDB; and/or
(v) the polynucleotide sequence of (e) as described above is not the polynucleotide sequence having accession number UM05080 in MUMDB.

In a further aspect, the present invention relates to a polypeptide encoded by the nucleic acid of the present invention.

In another aspect, the present invention relates to an expression cassette comprising one or more nucleic acids of the present invention.

In yet another aspect the present invention relates to a vector comprising the nucleic acid sequence of the present invention or the expression cassette of the present invention.

In a further aspect the present invention relates to a host cell overexpressing at least one of the nucleic acid molecules of the present invention, such as one, two, three, four or five nucleic acid molecules of the present invention.

In another aspect the present invention relates to a host cell underexpressing a polynucleotide having at least 50% sequence identity with the sequence of SEQ ID NO: 9, said polynucleotide sequence encoding a protein or fragment thereof having the activity of a cytochrome P450 monooxygenase.

In another aspect the present invention relates to a host cell overexpressing at least one of nucleic acid molecules of the present invention and underexpressing a polynucleotide having at least 50% sequence identity with the sequence of SEQ ID NO: 9, said polynucleotide sequence encoding a protein or fragment thereof having the activity of a cytochrome P450 monooxygenase.

In another aspect the present invention relates to a method of producing itaconic acid, comprising
(a) culturing a recombinant host cell of the present invention, and
(b) obtaining itaconic acid In yet another aspect the present invention relates to a use of a nucleic acid of the present invention, an expression cassette of the present invention, a vector of the present invention, or a host cell of the present invention for the production of itaconic acid in a host cell.

In another aspect the present invention relates to use of a nucleic acid of the present invention, an expression cassette of the present invention, or a vector of the present invention, for the production of a host cell, which is capable of producing itaconic acid.

In a further aspect the present invention relates to a method for producing a host cell, which is capable of producing itaconic acid, comprising genetically engineering of a host cell to overexpress a nucleic acid of the present invention or transforming said host cell with an expression cassette of the present invention, or with a vector of the present invention.

In some embodiments in the use of the present invention or in the method for producing a host cell of the present invention the host cell is a cell of a fungus or a yeast.

BRIEF DESCRIPTION OF THE DRAWINGS

FIG. 4 depicts nucleotide and derived amino acid sequences as disclosed in the instant document. Intron sequences are indicated by lowercase letters. FIG. 4A: SEQ ID NO: 1, nucleic acid sequence of UM11778(MB215), FIG. 4B: SEQ ID NO: 2, amino acid sequence of UM11778 (MB215), FIG. 4C: SEQ ID NO: 3, nucleic acid sequence of UM11777, FIG. 4D: SEQ ID NO: 4, nucleic acid sequence of UM05079, FIG. 4E: SEQ ID NO: 5, nucleic acid sequence of UM12299, FIG. 4F: SEQ ID NO: 6, nucleic acid sequence of UM05076, FIG. 4G: SEQ ID NO: 7, nucleic acid sequence of UM11778, FIG. 4H: SEQ ID NO: 8, nucleic acid sequence of UM05080, FIG. 4I: SEQ ID NO: 9, nucleic acid sequence of UM05074, FIG. 4J: SEQ ID NO: 10, amino acid sequence of UM11778, FIG. 4K: SEQ ID NO: 11, amino acid sequence of UM05074, FIG. 4L: SEQ ID NO: 12, amino acid sequence of UM12299 FIG. 4M: SEQ ID NO: 13, amino acid sequence of UM05076, FIG. 4N: SEQ ID NO: 14, amino acid sequence of UM11777, FIG. 4O: SEQ ID NO: 15, amino acid sequence of UM05079, FIG. 4P: SEQ ID NO: 16, amino acid sequence of UM05080, FIG. 4Q: SEQ ID NO: 17, nucleic acid sequence of UM02807, FIG. 4R: SEQ ID NO: 18, polypeptide sequence of UM02807, FIG. 4S: SEQ ID NO: 19, nucleic acid sequence of UM02806, FIG. 4T: SEQ ID NO: 20, polypeptide sequence of UM02806, FIG. 4U: SEQ ID NO: 21, nucleic acid sequence UM02808, FIG. 4V: SEQ ID NO: 22, Polypeptide sequence UM02808.

FIG. 13 Characterization of enzyme activities. (A) Aconitate-delta-isomerase (ADI) encoded by UM11778 catalyzes isomerization of cis-aconitate into trans-aconitate in both directions. (B) Trans-aconitate decarboxylase (TAD) encoded by UM05076 catalyzes decarboxylation of trans-aconitate to itaconic acid.

FIG. 14 Incubation of cis-aconitate with aconitate-delta-isomerase (ADI) and trans-aconitate decarboxylase (TAD) leads to formation of itaconic acid.

FIG. 15: Model for intracellular localization of itaconic acid biosynthesis in U. maydis.

FIG. 16: The um02807 cluster and its influence on the itaconate biosynthesis of U. maydis MB215. FIG. 16A: U. maydis genes present in the cluster of um02807 encode a putative CTP1-mitochondrial citrate transporter (ctp1), a putative aconitate-Δ-isomerase protein (PrpF), a putative transcriptional regulator (regulator), and genes present in the itaconate cluster encode a putative Cytochrome P450 monooxygenase (cyp3), a trans-aconitate decarboxylase (tad1), a Major Facilitator Superfamily transporter (itp1), an aconitate-Δ-isomerase (adi1), a putative mitochondrial tricarboxylate transporter (mtt1), and a putative transcriptional regulator (ria1). FIG. 16B: Relative itaconate concentration of different deletion, overexpression, and complementary mutants of U. maydis compared to the wildtype after 96 h in the screening medium specified in the Examples section is shown. Values are the arithmetic mean of two biological determinations. Error bars indicate deviation from the mean.

FIG. 17: Pairwise sequence alignment between the polynucleotide sequences of UM11778 (SEQ ID NO: 1) and UM02807 (SEQ ID NO: 17).

DETAILED DESCRIPTION OF THE INVENTION

Figure 1:
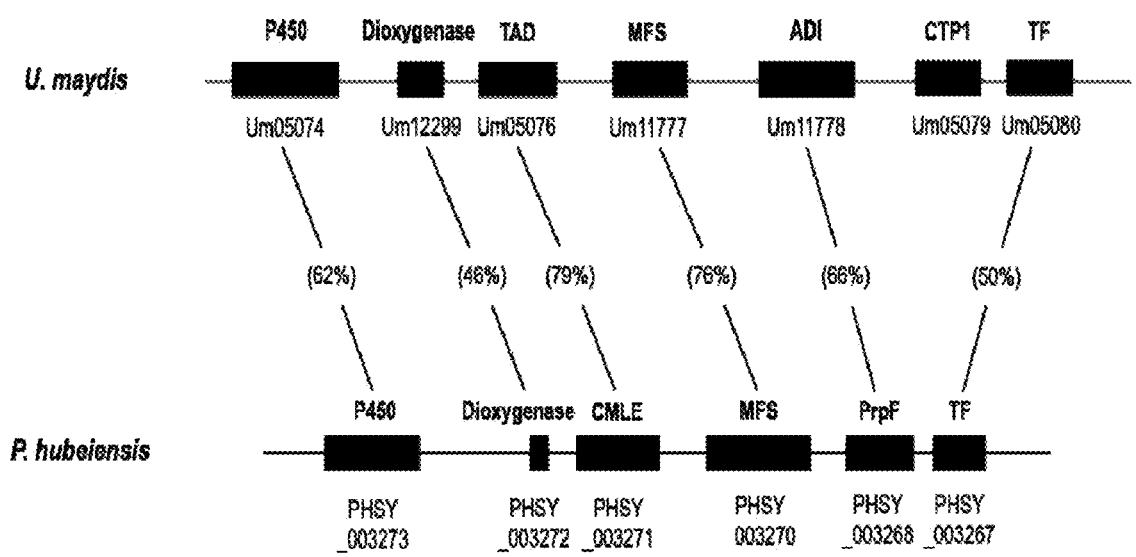
FIG. 1 is a graphical outline of the itaconic acid cluster in *U. maydis* including a comparison to the *Pseudozyma hubeiensis* cluster. Sequence similarities at the protein level of the *Pseudozyma hubeiensis* genes to the corresponding *U. maydis* genes were determined using ClustalW and are indicated in brackets.

As indicated above, the present inventors have identified two genes, UM05076 and UM11778 encoding the key enzymes for itaconic acid via cis- and trans-aconitate. The gene UM05076 encodes a trans-aconitate decarboxylase (TAD) and UM11778 encodes an aconitate-delta-isomerase (ADI). However, even though both genes are not existent in A. terreus or any other itaconic acid producing host known thus far they are found in the genome sequence of P. hubeiensis, which is a close relative to U. maydis (FIG. 1). In A. terreus other genes that are implicated in ITA production surround the cadA gene. ATEG_09970 encodes a putative mitochondrial tricarboxylic acid transporter (WO 2009/104958 A1) and ATEG_09972 encodes an ITA transporting major facilitator superfamily (MFS) transporter (WO 2009/110796 A1). The similarity in the organization of genes surrounding the genes encoding ADI and TAD in U. maydis and the cadA gene in A. terreus makes it likely that the surrounding U. maydis genes are also involved in ITA production. However, there is only little similarity between the amino acid sequences encoded by the genes in A. terreus and U. maydis. In fact, both knock-out and overexpression experiments confirmed that further genes, which surround the genes encoding ADI and TAD, are involved in the biosynthesis pathway for the production of itaconic acid. In particular a transporter of the major facilitator superfamily (MFS) with the accession number UM11777 in MUMDB is involved in the biosynthesis pathway for the production of itaconic acid. In fact, knock-out of UM11777 led to a decrease in ITA production.

Also the mitochondrial transporter CTP1 (CTP1) with the accession number UM05079 in MUMDB is particularly involved in the biosynthesis pathway for the production of itaconic acid. In fact, overexpression led to an increase in ITA production and knock-out led to a decrease in ITA production.

In addition, the functional transcription factor (transcription factor) with the accession number UM05080 in MUMDB is particularly involved in the biosynthesis pathway for the production of itaconic acid. In fact, overexpression led to an increase in ITA production and knock-out led to a decrease in ITA production.

Further, the cytochrome P450 monooxygenase (P450 monooxygenase) with the accession number UM05074 in MUMDB has an influence on the biosynthesis pathway for the production of itaconic acid. In fact, its overexpression led to a decrease in the production of ITA.

Based on the identification of the U. maydis enzymes and their corresponding genetic sequences new opportunities are provided for metabolic engineering of ITA production hosts with improved production characteristics. The identification of an ADI and a TAD enzyme from the phylum of Basidiomycota allows selection of the optimal enzyme in a heterologous host. Furthermore, in particular U. maydis has several characteristics that make it superior to A. terreus in an industrial setting, such as a yeast-like growth pattern and low sensitivity to medium impurities. The identification of the genes involved in ITA production in U. maydis will aid in optimizing this strain but also other strains of species different from U. maydis for biotechnological ITA production.

Definitions

Unless otherwise stated, the following terms used in this document, including the description and claims, have the definitions given below.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

The use of the terms "5'" and "3'" is a convention used to describe features of a nucleotide sequence related to either the position of genetic elements and/or the direction of events (5' to 3'), such as e.g. transcription by RNA polymerase or translation by the ribosome which proceeds in 5' to 3' direction. Synonyms are upstream (5') and downstream (3'). Conventionally, nucleotide sequences, gene maps, vector cards and RNA sequences are drawn with 5' to 3' from left to right or the 5' to 3' direction is indicated with arrows, wherein the arrowhead points in the 3' direction. Accordingly, 5' (upstream) indicates genetic elements positioned towards the left hand side, and 3' (downstream) indicates genetic elements positioned towards the right hand side, when following this convention.

The term "antibody" generally refers to an immunoglobulin, a fragment thereof or a proteinaceous binding molecule with immunoglobulin-like functions. Examples of (recombinant) immunoglobulin fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). An example of a proteinaceous binding molecule with immunoglobulin-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., *Protein Science* (2004) 13, 6, 1435-1448) or the crystalline scaffold (WO 2001/04144), the proteins described by Skerra (*J. Mol. Recognit.* (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). Where desired, a modifying agent may be used that further increases the affinity of the respective moiety for any or a certain form, class etc. of target matter.

The polynucleotide may be integrated in its natural locus. "Natural locus" means the location on a specific chromosome, where the polynucleotide is located. However, in another embodiment, the polynucleotide is present in the genome of the host cell not at their natural locus, but integrated ectopically. The term "ectopic integration" means the insertion of a nucleic acid into the genome of a microorganism at a site other than its usual chromosomal locus, i.e., predetermined or random integration.

By the use of the term "enriched" in reference to a polypeptide, a nucleic acid or a cell is meant that the specific amino acid/nucleotide sequence or cell, including cell population, constitutes a significantly higher fraction (2-5 fold) of the total amino acid sequences or nucleic acid sequence present in the sample of interest than in the natural source from which the sample was obtained. The polypeptide, a nucleic acid or a cell may also constitute a significantly higher fraction than in a normal or diseased organism or than in normal or diseased cells or in the cells from which the sequence was taken. This could be caused by preferential reduction in the amount of other amino acid/nucleotide sequences or cells present, or by a preferential increase in the amount of the specific amino acid/nucleotide sequence or cell of interest, or by a combination of the two. However, it should be noted that enriched does not imply that there are no other amino acid sequences, nucleotide sequences or cells present. The term merely defines that the relative amount of the sequence of interest has been significantly increased. The term significant here is used to indicate that the level of increase is useful to the person achieving such an increase, and generally means an increase relative to other amino acid or nucleic acid sequences of about at least 2-fold, for example at least about 5- to 10-fold or even more. The term is meant to cover only those situations in which man has intervened to increase the proportion of the desired amino acid sequence, nucleotide sequence or cell.

The term "essentially consists of" is understood to allow the presence of additional components in a sample or a composition that do not affect the properties of the sample or a composition. As an illustrative example, a pharmaceutical composition may include excipients if it essentially consists of an active ingredient.

The terms "expressing" and "expression" in reference to a nucleic acid as described herein are intended to be understood in the ordinary meaning as used in the art. A nucleic acid is expressed by a cell via transcription of a nucleic acid into mRNA, followed by translation into a polypeptide, which is folded and possibly further processed.

With regard to the respective biological process itself, the terms "expression", "gene expression" or "expressing" refer to the entirety of regulatory pathways converting the information encoded in the nucleic acid sequence of a gene first into messenger RNA (mRNA) and then to a protein. Accordingly, the expression of a gene includes its transcription into a primary hnRNA, the processing of this hnRNA into a mature RNA and the translation of the mRNA sequence into the corresponding amino acid sequence of the protein. In this context, it is also noted that the term "gene product" refers not only to a protein, including e.g. a final protein (including a splice variant thereof) encoded by that gene and a respective precursor protein where applicable, but also to the respective mRNA, which may be regarded as the "first gene product" during the course of gene expression.

By the term "expression cassette", also referred to as an expression system, is meant a nucleic acid molecule capable of directing expression of a particular nucleotide sequence in an appropriate host cell. An expression cassette includes a promoter operatively linked to the nucleotide sequence of interest, which is operatively linked to one or more termination signals. It may also include sequences required for proper translation of the nucleotide sequence. The coding region can encode a polypeptide of interest and can also encode a functional RNA of interest, including but not limited to, antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, however, the expression cassette is heterologous with respect to the host; i.e., the particular nucleic acid sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant or an animal, the promoter can also be specific to a particular tissue, organ, or stage of development.

By "fragment" in reference to a polypeptide as described herein is meant any amino acid sequence present in a polypeptide as described herein, as long as it is shorter than the full length sequence and as long as it is capable of performing the function of a protein involved in the biosynthesis of itaconic acid as described herein. Preferred fragments have at least 20, 40, 60, 80, 100, 120, 150, 200, 250, 300, 350, 400, 450, 500, 550, 600 amino acids. Such preferred fragments have the function of a protein involved in the biosynthesis of itaconic acid as described herein.

By "gene" is meant a unit of inheritance that occupies a specific locus on a chromosome and that is a segment of nucleic acid associated with a biological function. A gene encompasses transcriptional and/or translational regulatory sequences as well as a coding region. Besides a coding sequence a gene may include a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

A protein has "identity", or is "identical" to a second protein if the nucleic acid sequence that encodes the protein has a similar or identical sequence to the nucleic acid sequence that encodes the second protein. Also, a protein has identity to a second protein if the two proteins have "similar" amino acid sequences. Thus, the term "identical proteins" is defined to mean that the two proteins have similar or identical amino acid sequences. In a preferred embodiment, an identical protein is one that exhibits at least 30%, 40%, 50%, 60%, 70%, 80%, 85%, 90% or more such as 95%, 97%, 98% or 99% sequence identity to the wild type protein. In another preferred embodiment, an identical protein is one that exhibits at least 60% sequence identity to the wild type protein, more preferred is at least 70% sequence identity. Even more preferred are identical proteins that exhibit at least 80%, 85% or 90% sequence identity to the wild type protein. In a yet more preferred embodiment, an identical protein exhibits at least 95%, 97%, 98% or 99% sequence identity. As used herein, identity between two regions of amino acid sequence (especially with respect to predicted structural similarities) is interpreted as implying similarity in function.

Sequence identity for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of identity assigned to various substitutions, deletions and other modifications, including conservative amino acid substitutions. For instance, GCG contains programs such as "Gap" and "Bestfit" which can be used with default parameters to determine sequence identity or sequence identity between closely related polypeptides, such as identical polypeptides from different species of organisms or between a wild type protein and a mutein thereof. See, e. g., GCG Version 6.1. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein.

The term "isolated" indicates that the cell or cells, or the peptide(s) or nucleic acid molecule(s) has/have been removed from its/their normal physiological environment, e.g. a natural source, or that a peptide or nucleic acid is synthesized. Use of the term "isolated" indicates that a naturally occurring sequence has been removed from its normal cellular (i.e., chromosomal) environment. Thus, the sequence may be in a cell-free solution or placed in a different cellular environment. An isolated cell or isolated cells may for instance be included in a different medium such as an aqueous solution than provided originally, or placed in a different physiological environment. Typically isolated cells, peptides or nucleic acid molecule(s) constitute a higher fraction of the total cells, peptides or nucleic acid molecule(s) present in their environment, e.g. solution/suspension as applicable, than in the environment from which they were taken. By "isolated" in reference to a polypeptide or nucleic acid molecule is meant a polymer of amino acids (2 or more amino acids) or nucleotides coupled to each other, including a polypeptide or nucleic acid molecule that is isolated from a natural source or that is synthesized. The term "isolated" does not imply that the sequence is the only amino acid chain or nucleotide chain present, but that it is essentially free, e.g. about 90-95% pure or more, of e.g. non-amino acid material and/or non-nucleic acid material, respectively, naturally associated with it.

Isolation of a desired population of cells may in some embodiments include general cell enrichment techniques such as centrifugation, filtration or cell chromatography. Generally, isolating or enriching a desired population of cells may be carried out according to any desired technique known in the art. In some embodiments isolation of a desired population of cells may include the use of a commercially available cell isolation kit. "Isolating/isolation of itaconic acid" may in some embodiments include isolation of itaconic acid from the medium in which the host cell is cultured. This can be done e.g. after the cells were lysed or without lysation of the cells. Also it is possible, that the host cells are removed from the medium before isolation of itaconic acid takes place. Methods to isolate molecules such as itaconic acid are known to the person skilled in the art. One possibility is to isolate itaconic acid e.g. from the medium in which the host cell is cultured is via high pressure liquid chromatography (HPLC).

The term "MUMDB" as used herein refers to the MIPS *Ustilago maydis* DataBase provided by the Helmholtz Zentrum Muenchen. Access to that page can be obtained via the webpage http://mips.helmholtz-muenchen.de/genre/proj/ustilago.

The term "nucleic acid molecule" as used herein refers to any nucleic acid in any possible configuration, such as single stranded, double stranded or a combination thereof.

Examples of nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA), alkylphosphonate and alkylphosphotriester nucleic acid molecules and tecto-RNA molecules (e.g. Liu, B., et al., J. Am. Chem. Soc. (2004) 126, 4076-4077). LNA has a modified RNA backbone with a methylene bridge between C4' and O2', providing the respective molecule with a higher duplex stability and nuclease resistance. Alkylphosphonate and alkylphosphotriester nucleic acid molecules can be viewed as a DNA or an RNA molecule, in which phosphate groups of the nucleic acid backbone are neutralized by exchanging the P—OH groups of the phosphate groups in the nucleic acid backbone to an alkyl and to an alkoxy group, respectively. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label. A "nucleic acid" as used herein comprises a polynucleotide or, as also referred to herein, a nucleotide sequence. The terms "polynucleotide" and "nucleotide sequence" can thus be interchangeably used.

Many nucleotide analogues are known and can be used in nucleic acids used in the methods of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety may be a natural or a synthetic modification of A, C, G, and T/U, a different purine or pyrimidine base, such as uracil-5-yl, hypoxanthin-9-yl, and 2-aminoadenin-9-yl, as well as a non-purine or a non-pyrimidine nucleotide base. Other nucleotide analogues serve as universal bases. Examples of universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

Those skilled in the art will be familiar with the fact that corresponding sequences need to be compared. The use of a corresponding sequence includes that a position is not only determined by the number of the preceding nucleotides/amino acids. Accordingly, the position of a given amino acid in accordance with the disclosure which may be substituted may vary due to deletion or addition of amino acids elsewhere in a (mutant or wild-type) protein such as NS1. Thus, by a "corresponding position" in accordance with the disclosure it is to be understood that amino acids may differ in the indicated number—for instance when comparing data base entries—but may still have similar neighbouring amino acids.

The terms "overexpress," "overexpressing," "overexpressed" and "overexpression" in the present invention refer an expression of a gene or gene product or a polypeptide at a level greater than the expression of the same gene or gene product or polypeptide prior to a genetic alteration of the host cell or in a comparable host, which has not been genetically altered. If a host cell does not comprise a given gene or gene product, it is possible to introduce the gene or gene product into the host cell for expression; in this case, any detectable expression is encompassed by the term "overexpression." In one embodiment, overexpression is achieved by expressing 2, 3, 4 or more copies of said polynucleotide(s) in said host cell.

Overexpression can be achieved in a number of ways. In general, it can be achieved by increasing transcription/translation of the gene, e.g. by increasing the copy number of the gene or altering or modifying regulatory sequences or sites associated with expression of a gene. For example, the gene can be operably linked to a strong constitutive promoters and/or strong ubiquitous promoters in order to reach high expression levels. Alternatively, it is possible to remove regulatory sequences such that expression becomes constitutive. One can substitute a promoter with a heterologous promoter which increases expression of the gene or leads to constitutive expression of the gene. Using inducible promoters additionally make it possible to increase the expression in the course of the translation of the gene by fermentation. Furthermore, overexpression can also be achieved by, for example, modifying the chromosomal location of a particular gene, altering nucleic acid sequences adjacent to a particular gene such as a ribosome binding site or transcription terminator, modifying proteins (e.g., regulatory proteins, suppressors, enhancers, transcriptional activators and the like) involved in transcription of the gene and/or translation of the gene product, or any other conventional means of deregulating expression of a particular gene routine in the art (including but not limited to use of antisense nucleic acid molecules, for example, to block expression of repressor proteins or deleting or mutating the gene for a transcriptional factor which normally represses expression of the gene desired to be overexpressed. Prolonging the life of the mRNA may also improve the level of expression. If multiple copies of genes are included, the genes can either be located in plasmids of variable copy number or integrated and amplified in the chromosome.

Those skilled in the art will find relevant instructions in Martin et al. (Bio/Technology 5, 137-146 (1987)), Guerrero et al. (Gene 138, 35-41 (1994)), Tsuchiya and Morinaga (Bio/Technology 6, 428-430 (1988)), Eikmanns et al. (Gene 102, 93-98 (1991)), EP 0 472 869, U.S. Pat. No. 4,601,893, Schwarzer and Pühler (Bio/Technology 9, 84-87 (1991)), Reinscheid et al. (Applied and Environmental Microbiology 60, 126-132 (1994)), LaBarre et al. (Journal of Bacteriology 175, 1001-1007 (1993)), WO 96/15246, Malumbres et al. (Gene 134, 15-24 (1993)), JP-A-10-229891, Jensen and Hammer (Biotechnology and Bioengineering 58, 191-195 (1998)) and Makrides (Microbiological Reviews 60, 512-538 (1996)), inter alia, and in well-known textbooks on genetics and molecular biology.

The terms "underexpress," "underexpressing," "underexpressed" and "underexpression" in the present invention refer an expression of a gene or gene product or a polypeptide at a level lower than the expression of the same gene or gene product or polypeptide prior to a genetic alteration of the host cell or in a comparable host which has not been genetically altered. If a host cell does not comprise a given gene or gene product, it is possible to decrease or delete the gene or gene product from the host cell. In one embodiment, underexpression is achieved by deletion of said polynucleotide(s) in said host cell.

Underexpression can be achieved in a number of ways. In general, it can be achieved by decreasing transcription/translation of the gene, e.g. by altering or modifying regulatory sequences or sites associated with expression of a gene. Other methods that can be used to achieve underexpression are e.g. siRNA methods or gene knock-out strategies.

The terms "polypeptide" and "protein" refer to a polymer of amino acid residues and are not limited to a certain minimum length of the product. Where both terms are used concurrently, this twofold naming accounts for the use of both terms side by side in the art.

The term "promoter" as used throughout this document, refers to a nucleic acid sequence needed for gene sequence expression. Promoter regions vary from organism to organism, but are well known to those skilled in the art for different organisms. For example, in prokaryotes, the promoter region contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like. Both constitutive and inducible promoters can be used in the present invention, in accordance with the needs of a particular embodiment. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of a selected nucleic acid sequence. The promoter can also be a recombinant promoter.

In case of the host cell being *Ustilago maydis*, a suitable promoter is the constitutive tef, otef promoter (Spellig et al. (1996), Mol Gen Genet 252, 503-509), hsp70 promoter (Holden et al., EMBO J. 8, 1927-1934). A preferred inducible promoter is the nar1 promoter (Brachmann et al., (2001), Mol Microbiol. 42, 1047-63) or the crg1 promoter (Bottin et al. (1996), Mol Gen Genet 253, 342-352).

The term "purified" is understood to be a relative indication in comparison to the original environment of the cell, thereby representing an indication that the cell is relatively purer than in the natural environment. It therefore includes, but does not only refer to, an absolute value in the sense of absolute purity from other cells (such as a homogeneous cell population). Compared to the natural level, the level after purifying the cell will generally be at least 2-5 fold greater (e.g., in terms of cells/ml). Purification of at least one order of magnitude, such as about two or three orders, including for example about four or five orders of magnitude is expressly contemplated. It may be desired to obtain the cell at least essentially free of contamination, in particular free of other cells, at a functionally significant level, for example about 90%, about 95%, or 99% pure. With regard to a nucleic acid, a peptide, a protein or a peptidomimetic, the above applies mutatis mutandis. In this case purifying the nucleic acid, peptide or protein will for instance generally be at least 2-5 fold greater (e.g., in terms of mg/ml).

The word "recombinant" is used in this document to describe a nucleic acid molecule that, by virtue of its origin, manipulation, or both is not associated with all or a portion of the nucleic acid molecule with which it is associated in nature. Generally a recombinant nucleic acid molecule includes a sequence which does not naturally occur in the respective wildtype organism or cell. Typically a recombinant nucleic acid molecule is obtained by genetic engineering, usually constructed outside of a cell. Generally a recombinant nucleic acid molecule is at least substantially identical and/or substantial complementary to at least a portion of the corresponding nucleic acid molecule occurring in nature. A recombinant nucleic acid molecule may be of any origin, such as genomic, cDNA, mammalian, bacterial, viral, semisynthetic or synthetic origin. The term "recombinant" as used with respect to a protein/polypeptide means a polypeptide produced by expression of a recombinant polynucleotide. A recombinant cell, polypeptide, or nucleic acid can be typically described with reference to how it differs from a naturally occurring counterpart (the "wild-type"). A "recombinant cell" or "recombinant host cell" refers to a cell or host cell that has been genetically altered to comprise a nucleic acid sequence which was not native to said cell.

The recombinant host cell within the present invention does not necessarily contain the nucleic acid sequences encoding a protein of interest. It is appreciated by a skilled person in the art that the host cells can be provided for inserting desired nucleotide sequences into the host cell, for example, in a kit.

As used herein, "engineered" host cells are host cells which have been manipulated using genetic engineering, i.e. by human intervention. When a host cell is "engineered to overexpress" a given protein, the host cell is manipulated such that the expression of the given protein is increased compared to the host cell under the same condition prior to manipulation (or "prior to engineering"). The degree of overexpression may be 10, 20, 30, 40, 50, 60, 70, 80, 90, 100, 200, 300, 400, 500% or more compared to the host cell under the same condition prior to manipulation (or "prior to engineering") When a host cell is "engineered to underexpress" a given protein, the host cell is manipulated such that the expression of the given protein is decreased compared to the host cell under the same condition prior to manipulation (or "prior to engineering"). The degree of underexpression may be 10, 20, 30, 40, 50, 60, 70, 80, 90, or 100% compared to the host cell under the same condition prior to manipulation (or "prior to engineering").

The term "vector", sometimes also referred to as gene delivery system or gene transfer vehicle, relates to a macromolecule or complex of molecules that include(s) a polynucleotide to be delivered to a host cell, whether in vitro, ex vivo or in vivo. Typically a vector is a single or double-stranded circular nucleic acid molecule that allows or facilitates the transfer of a nucleic acid sequence into a cell. A vector can generally be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a peptide, such as a sequence that includes a sequence of the present invention can be inserted into a vector by cutting the vector with restriction enzymes and ligating the two pieces together. A vector may for instance be a viral vector, such as a retroviral vector, a Lentiviral vector, a herpes virus based vector or an adenoviral vector. A vector may also be a plasmid vector, which is also a typical example of a prokaryotic vector. A respective plasmid may in some embodiments be a plasmid capable of replication in *E. coli*, such as, for example, pBR322, ColE1, pSC101, pACYC 184 or πVX. *Bacillus* plasmids include pC194, pC221 or pT127. Suitable *Streptomyces* plasmids include p1J101, and *Streptomyces* bacteriophages such as ϕC31. A vector may also be a liposome-based extrachromosomal vector, also called episomal vector. Two illustrative examples of an episomal vector are an oriP-based vector and a vector encoding a derivative of EBNA-1. Lymphotrophic herpes virus is a herpes virus which replicates in a lymphoblast and becomes a plasmid for a part of its natural life-cycle. A vector may also be based on an organically modified silicate. In some embodiments a vector may be a transposon-based system, i.e. a transposon/transposase system, such as the so called Sleeping Beauty, the Frog Prince transposon—transposase system or the TTAA-specific transposon piggyBac system. Transposons are mobile genetic elements in that they are sequences of DNA that can move around to different positions within the genome of a single cell, a process called transposition. In the process, a transposon can cause mutations and change the amount of DNA in the genome.

The terms "comprising", "including," containing", "having" etc. shall be read expansively or open-ended and without limitation. Singular forms such as "a", "an" or "the" include plural references unless the context clearly indicates otherwise. Thus, for example, reference to a "vector" includes a single vector as well as a plurality of vectors, either the same—e.g. the same operon—or different. Likewise reference to "cell" includes a single cell as well as a plurality of cells. Unless otherwise indicated, the term "at least" preceding a series of elements is to be understood to refer to every element in the series. The terms "at least one" and "at least one of" include for example, one, two, three, four, or five or more elements. It is furthermore understood that slight variations above and below a stated range can be used to achieve substantially the same results as a value within the range. Also, unless indicated otherwise, the disclosure of ranges is intended as a continuous range including every value between the minimum and maximum values.

The scope and meaning of any use of a term will be apparent from the specific context in which the term is used. Certain further definitions for selected terms used throughout this document are given in the appropriate context of the detailed description, as applicable. Unless otherwise defined, all other scientific and technical terms used in the description, figures and claims have their ordinary meaning as commonly understood by one of ordinary skill in the art.

ADI/TAD and Further Genes and Proteins

The nucleic acids and proteins of the present invention as well as their abbreviation are disclosed below.

| Abbreviation | UM Number in MUMDB | Protein SEQ ID | Nucleic acid SEQ ID |
| --- | --- | --- | --- |
| ADI | UM11778 | SEQ ID NO: 2 or SEQ ID NO: 10 | SEQ ID NO: 1 or SEQ ID NO: 7 |
| TAD | UM05076 | SEQ ID NO: 13 | SEQ ID NO: 6 |
| MFS | UM11777 | SEQ ID NO: 14 | SEQ ID NO: 3 |
| CTP1 | UM05079 | SEQ ID NO: 15 | SEQ ID NO: 4 |
| Transcription factor | UM05080 | SEQ ID NO: 16 | SEQ ID NO: 8 |
| P450-Monooxygenase | UM05074 | SEQ ID NO: 11 | SEQ ID NO: 9 |
| ADI2 | UM02807 | SEQ ID NO: 18 | SEQ ID NO: 17 |
| CFP1 | UM02806 | SEQ ID NO: 20 | SEQ ID NO: 19 |
| regulator | UM02808 | SEQ ID NO: 22 | SEQ ID NO: 21 |

A suitable polynucleotide sequence of an aconitate-delta-isomerase (ADI) and/or a trans-aconitate decarboxylase (TAD) according to the invention, or a complement of such a polynucleotides sequence, may be included in any nucleic acid molecule. In some embodiments such a polynucleotide sequence is operably linked to a sequence that is capable of regulating gene expression. The polynucleotide sequence may for instance be operably linked to a promoter. As a further example, the polynucleotide sequence may be operably linked to an enhancer, including a silencer. In some embodiments the sequence capable of regulating gene expression is located on the same nucleic acid molecule as the polynucleotide sequence according to the invention. In some embodiments the sequence capable of regulating gene expression is located on a nucleic acid molecule that is different from the nucleic acid molecule on which the polynucleotide sequence according to the invention is located.

A polynucleotide sequence of an ADI (UM11778) included in a nucleic acid molecule according to the invention in some embodiments is at least essentially identical to the sequence of SEQ ID NO: 1. The polynucleotide sequence of an ADI according to the invention may have at least 30%, 40%, or 50% sequence identity with the sequence of SEQ ID NO: 1.

In some embodiments a nucleic acid molecule according to the invention includes a sequence that encodes a functional fragment of an ADI. Such a polynucleotide sequence may for example include a sequence of about 1000 contiguous bases of SEQ ID NO: 1. In some embodiments a respective polynucleotide sequence may include a sequence of about 850 contiguous bases of SEQ ID NO: 1.

In some embodiments the polynucleotide sequence of an ADI (UM11778) is at least essentially identical to the sequence of SEQ ID NO: 7. The polynucleotide sequence of an ADI according to the invention may have at least 30%, 40%, or 50% sequence identity with the sequence of SEQ ID NO: 7.

Another polynucleotide sequence of an aconitate-delta-isomerase is a polynucleotide sequence on an ADI2 (UM02807). The polynucleotide sequence of an ADI2 (UM02807) is at least essentially identical to the sequence of SEQ ID NO: 17. The polynucleotide sequence of an ADI2 according to the invention may have at least 30% sequence identity with the sequence of SEQ ID NO: 17. It is envisioned by the invention that an ADI2 can substitute an ADI. Hence, embodiments comprising ADI also envision embodiments in which ADI is substituted by ADI2 as well as embodiments, where ADI and ADI2 are present. The terms "ADI" and "ADI2" as used in this paragraph refer to the polynucleotide sequence encoding for aconitate-delta-isomerase as well as to a polypeptide encoded by said polynucleotide sequences.

In some embodiments a nucleic acid molecule according to the invention includes a functional fragment of the sequence of SEQ ID NO: 7. The functional fragment may be a polynucleotide sequence that includes a sequence of about 1000 contiguous bases of SEQ ID NO: 7. In some embodiments such a polynucleotide sequence may include a sequence of about 850 contiguous bases of SEQ ID NO: 7.

A polynucleotide sequence of a TAD (UM05076) included in a nucleic acid molecule according to the invention in some embodiments is at least essentially identical to the sequence of SEQ ID NO: 6. The polynucleotide sequence of a TAD according to the invention may have at least 50% sequence identity with the sequence of SEQ ID NO: 6.

In some embodiments a nucleic acid molecule according to the invention includes a sequence that encodes a functional fragment of a TAD. Such a polynucleotide sequence may for example include a sequence of about 1000 contiguous bases of SEQ ID NO: 6 or an identical sequence of the sequence of this length. In some embodiments a respective polynucleotide sequence may include a sequence of about 850 contiguous bases of SEQ ID NO: 6 or an identical sequence of the sequence of this length.

A polynucleotide sequences of an ADI and a TAD included in a nucleic acid molecule according to the invention in some embodiments is at least essentially identical to the sequence of SEQ ID NO: 1 and/or SEQ ID NO: 7 and SEQ ID NO: 6. The polynucleotide sequence of an ADI and a TAD according to the invention may have at least 30%, 40%, or 50% sequence identity with the sequence of SEQ ID NO: 1 and/or SEQ ID NO: 7 and SEQ ID NO: 6.

In some embodiments a nucleic acid molecule according to the invention includes a sequence that encodes a functional fragment of an ADI and a TAD. Such a polynucleotide sequence may for example include a sequence of about 1000 contiguous bases of SEQ ID NO: 1 and/or SEQ ID NO: 7 and SEQ ID NO: 6 or an identical sequence of the sequence of this length. In some embodiments a respective polynucleotide sequence may include a sequence of about 850 contiguous bases of SEQ ID NO: 1 and/or SEQ ID NO: 7 and SEQ ID NO: 6 or an identical sequence of the sequence of this length.

Similarly, an isolated nucleic acid molecule of the invention can comprise polynucleotide sequences wherein the polynucleotide having at least 30%, 40%, or 50% sequence identity with the sequence of SEQ ID NO: 1 and/or SEQ ID NO: 7 and SEQ ID NO: 6 encoding a polypeptide having activity of an aconitate-delta-isomerase (ADI) or encoding a polypeptide having activity of a trans-aconitate decarboxylase (TAD).

A polynucleotide sequence of a CTP1 (UM05079) included in a nucleic acid molecule according to the invention in some embodiments is at least essentially identical to the sequence of SEQ ID NO: 4. The polynucleotide sequence of a CTP1 according to the invention may have at least 50% sequence identity with the sequence of SEQ ID NO: 4.

In some embodiments a nucleic acid molecule according to the invention includes a sequence that encodes a functional fragment of a CTP1. Such a polynucleotide sequence may for example include a sequence of about 1000 contiguous bases of SEQ ID NO: 4 or an identical sequence of the sequence of this length. In some embodiments a respective polynucleotide sequence may include a sequence of about 850 contiguous bases of SEQ ID NO: 4 or an identical sequence of the sequence of this length.

A polynucleotide sequence of a MFS (UM11777) included in a nucleic acid molecule according to the invention in some embodiments is at least essentially identical to the sequence of SEQ ID NO: 3. The polynucleotide sequence of a MFS according to the invention may have at least 50% sequence identity with the sequence of SEQ ID NO: 3.

In some embodiments a nucleic acid molecule according to the invention includes a sequence that encodes a functional fragment of a MFS. Such a polynucleotide sequence may for example include a sequence of about 1500 contiguous bases of SEQ ID NO: 3 or an identical sequence of the sequence of this length. In some embodiments a respective polynucleotide sequence may include a sequence of about 950 contiguous bases of SEQ ID NO: 3 or an identical sequence of the sequence of this length.

A polynucleotide sequence of a transcription factor (UM05080) included in a nucleic acid molecule according to the invention in some embodiments is at least essentially identical to the sequence of SEQ ID NO: 8. The polynucleotide sequence of a transcription factor according to the invention may have at least 50% sequence identity with the sequence of SEQ ID NO: 8.

In some embodiments a nucleic acid molecule according to the invention includes a sequence that encodes a functional fragment of the transcription factor. Such a polynucleotide sequence may for example include a sequence of about 1000 contiguous bases of SEQ ID NO: 8 or an identical sequence of the sequence of this length. In some embodiments a respective polynucleotide sequence may include a sequence of about 850 contiguous bases of SEQ ID NO: 8 or an identical sequence of the sequence of this length.

A polynucleotide sequence of a cytochrome P450-Monooxygenase (UM05074) included in a nucleic acid molecule according to the invention in some embodiments is at least essentially identical to the sequence of SEQ ID NO: 9. The polynucleotide sequence of a cytochrome P450-Monooxygenase according to the invention may have at least 50% sequence identity with the sequence of SEQ ID NO: 9.

In some embodiments a nucleic acid molecule according to the invention includes a sequence that encodes a functional fragment of the cytochrome P450 monooxygenase. Such a polynucleotide sequence may for example include a sequence of about 1500 contiguous bases of SEQ ID NO: 9 or an identical sequence of the sequence of this length. In some embodiments a respective polynucleotide sequence may include a sequence of about 950 contiguous bases of SEQ ID NO: 9 or an identical sequence of the sequence of this length.

In addition, the polynucleotide sequence may include a nucleotide sequence, which results from the addition, deletion or substitution of at least one nucleotide to the 5'-end and/or the 3'-end of the nucleic acid formula shown in a given sequence. Any nucleotide or polynucleotide may be used in this regard, provided that its addition, deletion or substitution does not alter the amino acid sequence, which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, a nucleic acid molecule according to the present invention may, as necessary, have restriction endonuclease recognition sites added to its 5'-end and/or its 3'-end. Such functional alterations of a given nucleic acid sequence afford an opportunity to promote secretion and/or processing of heterologous proteins encoded by foreign nucleic acid sequences fused thereto.

Hence, in some embodiments a nucleic acid of the inventions has a polynucleotide sequence that lacks a portion of a SEQ ID NO defined in this document. Typically an encoded amino acid stretch is lacking so that the remaining amino acids are in the form of a shortened polypeptide, i.e., the respective amino acid stretch is deleted "in frame" and accordingly the encoding polynucleotide sequence lacks a base triplet or a plurality of consecutive base triplets.

Further, it is possible to delete codons or to substitute one or more codons with codons other than degenerate codons to produce a structurally modified polypeptide, but one which has substantially the same utility or activity as the polypeptide produced by the unmodified nucleic acid molecule. As recognized in the art, the two polypeptides are functionally equivalent, as are the two nucleic acid molecules that give rise to their production, even though the differences between the nucleic acid molecules are not related to the degeneracy of the genetic code.

A polypeptide/protein/peptidomimetic according to the invention may be a polypeptide molecule that has, including consists of and essentially consists of, a sequence of a functional ADI. The polypeptide in some embodiments includes, including consist of and at least essentially consists of, a sequence that is at least essentially identical to the sequence of SEQ ID NO: 2. In some embodiments the polypeptide sequence of an ADI according to the invention has at least 30%, 40%, or 50% sequence identity with the sequence of SEQ ID NO: 2.

In some embodiments a polypeptide or peptidomimetic according to the invention includes a functional fragment of the sequence of SEQ ID NO: 2. The functional fragment may be a polynucleotide sequence that includes a sequence of about 400 contiguous amino acids of SEQ ID NO: 2. In some embodiments such an amino acid sequence may include a sequence of about 350 contiguous bases of SEQ ID NO: 2.

As indicated above, instead of or in addition to a peptide, a peptidomimetic may likewise be used in the context of the present invention. The term "peptidomimetic" as used herein refers to a compound that has the same general structure as a corresponding polypeptide, but which includes modifications that increase its stability or biological function. In some embodiments a peptidomimetic may include one or more D-amino acids, essentially consist of D-amino acids or consist of D-amino acids. D-amino acids are the optical isomer of a naturally occurring L-amino acid. A D-amino acid can be taken to be a mirror image of a L-amino acid. Stretches of D-amino acids are less prone to be degraded in a host organism via proteolysis. In some embodiments a peptidomimetic may be an inverso analog, which is an analog of the same sequence that consists only of D-amino acids. In some embodiments a peptidomimetic may be a "reverse" analogue of a given peptide, which means that the peptidomimetic includes the reverse sequence of the peptide. In some embodiments a peptidomimetic may be a "D-retro-enantiomer peptide", which is an analog that consists of D-amino acids, with the sequence arranged in the reversed order. A peptidomimetic may also include, essentially consist of or consist of a peptoid. A peptoid differs from peptides in that the side chain is connected to the amide nitrogen rather than the carbon atom. A peptoid can thus be taken to be an oligo(N-alkyl) glycine, which nevertheless has the same or substantially the same amino acid sequence as the corresponding polypeptide. Peptoids are typically resistant to proteases and other modifying enzymes and can have a much higher cell permeability than peptides (see e.g. Kwon, Y.-U., and Kodadek, T., J. Am. Chem. Soc. (2007) 129, 1508-1509).

The peptide or peptidomimetic may be prepared by any method, such as by synthesizing the peptide or peptidomimetic, or by expressing a nucleic acid encoding an appropriate amino acid sequence in a cell and harvesting the peptide from the cell. A combination of such methods may likewise be used. Methods of de novo synthesizing peptides and peptidomimetics, and methods of recombinantly producing peptides and peptidomimetics are well known in the art.

As mentioned above, in some embodiments a sequence of the invention corresponds to one of the SEQ ID NOs of this document, such as a sequence corresponding to SEQ ID NO: 1 or SEQ ID NO: 7, and contains a conservative substitution. Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu-→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr-→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

1) Alanine (Ala), Glycine (Gly);
2) Aspartic acid (Asp), Glutamic acid (Glu);
3) Asparagine (Asn), Glutamine (Gln);
4) Arginine (Arg), Lysine (Lys);
5) Isoleucine (Ile), Leucine (Leu), Methionine (Met), Valine (Val);
6) Phenylalanine (Phe), Tyrosine (Tyr), Tryptophan (Trp);
7) Serine (Ser), Threonine (Thr); and
8) Cysteine (Cys), Methionine (Met)

A polypeptide/protein/peptidomimetic according to the invention may be a polypeptide molecule that has, including consists of and essentially consists of, a sequence of a functional ADI. The polypeptide in some embodiments includes, including consist of and at least essentially consists of, a sequence that is at least essentially identical to the sequence of SEQ ID NO: 10. In some embodiments the polypeptide sequence of a ADI according to the invention has at least 30%, 40%, or 50% sequence identity with the sequence of SEQ ID NO: 10.

polypeptide/protein/peptidomimetic according to the invention may be a polypeptide molecule that has, including consists of and essentially consists of, a sequence of a functional ADI2. The polypeptide in some embodiments includes, including consist of and at least essentially consists of, a sequence that is at least essentially identical to the sequence of SEQ ID NO: 18. In some embodiments the polypeptide sequence of an ADI according to the invention has at least 30% sequence identity with the sequence of SEQ ID NO: 18.

In some embodiments a polypeptide or peptidomimetic according to the invention includes a functional fragment of the sequence of SEQ ID NO: 10. The functional fragment may be a polynucleotide sequence that includes a sequence of about 400 contiguous amino acids of SEQ ID NO: 10. In some embodiments such an amino acid sequence may include a sequence of about 350 contiguous bases of SEQ ID NO: 10.

A polypeptide/protein/peptidomimetic according to the invention may be a polypeptide molecule that has, including consists of and essentially consists of, a sequence of a functional TAD (trans-aconitate decarboxylase). The polypeptide in some embodiments includes, including consist of and at least essentially consists of, a sequence that is at least essentially identical to the sequence of SEQ ID NO: 13. In some embodiments the polypeptide sequence of a TAD according to the invention has at least 50% sequence identity with the sequence of SEQ ID NO: 13.

In some embodiments a polypeptide or peptidomimetic according to the invention includes a functional fragment of the sequence of SEQ ID NO: 13. The functional fragment may be a polynucleotide sequence that includes a sequence of about 400 contiguous amino acids of SEQ ID NO: 13. In some embodiments such an amino acid sequence may include a sequence of about 450 contiguous bases of SEQ ID NO: 13.

A polypeptide/protein/peptidomimetic according to the invention may be a polypeptide molecule that has, including consists of and essentially consists of, a sequence of a functional CTP1 (mitochondrial transporter CTP1). The polypeptide in some embodiments includes, including consist of and at least essentially consists of, a sequence that is at least essentially identical to the sequence of SEQ ID NO: 15. In some embodiments the polypeptide sequence of a CTP1 according to the invention has at least 50% sequence identity with the sequence of SEQ ID NO: 15.

In some embodiments a polypeptide or peptidomimetic according to the invention includes a functional fragment of the sequence of SEQ ID NO: 15. The functional fragment may be a polynucleotide sequence that includes a sequence of about 200 contiguous amino acids of SEQ ID NO: 15. In some embodiments such an amino acid sequence may include a sequence of about 250 contiguous bases of SEQ ID NO: 15.

A polypeptide/protein/peptidomimetic according to the invention may be a polypeptide molecule that has, including consists of and essentially consists of, a sequence of a functional MFS (transporter of the major facilitator superfamily). The polypeptide in some embodiments includes, including consist of and at least essentially consists of, a sequence that is at least essentially identical to the sequence of SEQ ID NO: 14. In some embodiments the polypeptide sequence of a MFS according to the invention has at least 50% sequence identity with the sequence of SEQ ID NO: 14.

In some embodiments a polypeptide or peptidomimetic according to the invention includes a functional fragment of the sequence of SEQ ID NO: 14. The functional fragment may be a polynucleotide sequence that includes a sequence of about 400 contiguous amino acids of SEQ ID NO: 14. In some embodiments such an amino acid sequence may include a sequence of about 450 contiguous bases of SEQ ID NO: 14.

A polypeptide/protein/peptidomimetic according to the invention may be a polypeptide molecule that has, including consists of and essentially consists of, a sequence of a functional transcription factor (UM05080). The polypeptide in some embodiments includes, including consist of and at least essentially consists of, a sequence that is at least essentially identical to the sequence of SEQ ID NO: 16. In some embodiments the polypeptide sequence of a transcription factor according to the invention has at least 50% sequence identity with the sequence of SEQ ID NO: 16.

In some embodiments a polypeptide or peptidomimetic according to the invention includes a functional fragment of the sequence of SEQ ID NO: 16. The functional fragment may be a polynucleotide sequence that includes a sequence of about 300 contiguous amino acids of SEQ ID NO: 16. In some embodiments such an amino acid sequence may include a sequence of about 350 contiguous bases of SEQ ID NO: 16.

A polypeptide/protein/peptidomimetic according to the invention may be a polypeptide molecule that has, including consists of and essentially consists of, a sequence of a functional ADI and a sequence of a functional TAD. The polypeptide in some embodiments includes, including consist of and at least essentially consists of, a sequence that is at least essentially identical to the sequence of SEQ ID NO: 10 and SEQ ID NO: 13. In some embodiments the polypeptide sequence of an ADI and a TAD according to the invention has at least 30%, 40%, or 50% sequence identity with the sequence of SEQ ID NO: 10 and at least 50% sequence identity with the sequence of SEQ ID NO: 13.

In some embodiments a polypeptide or peptidomimetic according to the invention includes a functional fragment of the sequence of SEQ ID NO: 10 and SEQ ID NO: 13. The functional fragment may be a polynucleotide sequence that includes a sequence of about 400 contiguous amino acids of SEQ ID NO: 10 and SEQ ID NO: 13. In some embodiments such an amino acid sequence may include a sequence of about 350 contiguous bases of SEQ ID NO: 10 and about 450 contiguous bases of SEQ ID NO: 13.

A polypeptide/protein/peptidomimetic according to the invention may be a polypeptide molecule that has, including consists of and essentially consists of, a sequence of a functional ADI and a sequence of a functional TAD. The polypeptide in some embodiments includes, including consist of and at least essentially consists of, a sequence that is at least essentially identical to the sequence of SEQ ID NO: 2 and SEQ ID NO: 13. In some embodiments the polypeptide sequence of an ADI and a TAD according to the invention has at least 30%, 40%, or 50% sequence identity with the sequence of SEQ ID NO: 2 and at least 50% sequence identity with the sequence of SEQ ID NO: 13.

In some embodiments a polypeptide or peptidomimetic according to the invention includes a functional fragment of the sequence of SEQ ID NO: 2 and SEQ ID NO: 13. The functional fragment may be a polynucleotide sequence that includes a sequence of about 400 contiguous amino acids of SEQ ID NO: 2 and SEQ ID NO: 13. In some embodiments such an amino acid sequence may include a sequence of about 350 contiguous bases of SEQ ID NO: 2 and about 450 contiguous bases of SEQ ID NO: 13.

A polypeptide/protein/peptidomimetic according to the invention may be a polypeptide molecule that has, including consists of and essentially consists of, a sequence of a functional ADI. The polypeptide in some embodiments includes, including consist of and at least essentially consists of, a sequence that is at least essentially identical to the sequence of SEQ ID NO: 2. In some embodiments the polypeptide sequence of an ADI according to the invention has at least 30%, 40%, or 50% sequence identity with the sequence of SEQ ID NO: 2.

In some embodiments a polypeptide or peptidomimetic according to the invention includes a functional fragment of the sequence of SEQ ID NO: 2. The functional fragment may be a polynucleotide sequence that includes a sequence of about 400 contiguous amino acids of SEQ ID NO: 2. In some embodiments such an amino acid sequence may include a sequence of about 350 contiguous bases of SEQ ID NO: 2.

Similarly, the present invention relates to an isolated polypeptide molecule comprising an amino acid sequences having at least 30%, 40%, or 50% sequence identity with the sequence of SEQ ID NO: 2 and/or SEQ ID NO: 10 and having at least 50% sequence identity with the sequence of SEQ ID NO: 13 and having ADI activity or TAD activity.

The polypeptide in some embodiments includes, including consist of and at least essentially consists of, a sequence that is at least essentially identical to the sequence of SEQ ID NO: 2 and/or SEQ ID NO: 10 and/or SEQ ID NO: 13 and SEQ ID NO: 14. In some embodiments the polypeptide sequence according to the invention has at least 30%, 40%, or 50% sequence identity with the sequence of SEQ ID NO: 2 and/or SEQ ID NO: 10 and/or at least 50% sequence identity with the sequence of SEQ ID NO: 13 and SEQ ID NO: 14.

The polypeptide in some embodiments includes, including consist of and at least essentially consists of, a sequence that is at least essentially identical to the sequence of SEQ ID NO: 2 and/or SEQ ID NO: 10 and/or SEQ ID NO: 13 and SEQ ID NO: 15. In some embodiments the polypeptide sequence according to the invention has at least 30%, 40%, or 50% sequence identity with the sequence of SEQ ID NO: 2 and/or SEQ ID NO: 10 and/or at least 50% sequence identity with the sequence of SEQ ID NO: 13 and SEQ ID NO: 15.

The polypeptide in some embodiments includes, including consist of and at least essentially consists of, a sequence that is at least essentially identical to the sequence of SEQ ID NO: 2 and/or SEQ ID NO: 10 and/or SEQ ID NO: 13 and SEQ ID NO: 16. In some embodiments the polypeptide sequence according to the invention has at least 30%, 40%, or 50% sequence identity with the sequence of SEQ ID NO: 2 and/or SEQ ID NO: 10 and/or at least 50% sequence identity with the sequence of SEQ ID NO: 13 and SEQ ID NO: 16.

In the absence of any identifiable protein with a sequence of 70% or more amino acid identity, a protein of *Pseudogulbenkiania* sp. NH8B with GenBank GENE ID: 11156442 NH8B_2749 (SEQ ID NO: 23), having 53% amino acid identity to the protein of SEQ ID NO: 10 may serve as an illustrative example. This protein has at amino acid positions 12 to 17 the sequence GGTSKG, whereas the protein of SEQ ID NO: 10 has at amino acid positions 12 to 17 the sequence AGTSRG. The exchange of R to K at position 16 and the exchange of A to G at position 12 can both be taken to define a conservative substitution. Further, the protein of *Pseudogulbenkiania* sp. NH8B has at amino acid positions 19 to 29 the sequence FFLAD DLPADP, while at amino acid positions 19 to 29 the protein of SEQ ID NO: 10 has the sequence YFLASDLPAEP. The exchange of Y to F at position 19 and the exchange of E to D at position 28 can both be taken to define a conservative substitution. In contrast thereto, the exchange of S to D at position 23 can be taken to define a non-conservative substitution.

As already implied above, more substantial changes, such as the following, do not represent conservative substitutions: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

A polynucleotide sequence according to the invention may also be a sequence that is capable of hybridizing to a sequence encoding a ADI, TAD, CTP1, MFS, transcription factor having activity for one of nucleic acids of SEQ ID NO: 1, 7, 3, 4, 6, 8 and/or 9, (e.g. UM05080; SEQ ID NO: 8) or a cytochrome P450 monooxygenase (e.g. UM05074; SEQ ID NO: 9). The nucleic acid molecule may for instance be capable of hybridizing to a polynucleotide sequence having at least 30%, 40%, or 50% sequence identity with the sequence of SEQ ID NO: 1, said polynucleotide sequence encoding a protein or fragment thereof having aconitate-delta-isomerase (ADI) activity.

The nucleic acid molecule may for instance be capable of hybridizing to a polynucleotide sequence having at least 30%, 40%, or 50% sequence identity with the sequence of SEQ ID NO: 7, said polynucleotide sequence encoding a protein or fragment thereof having aconitate-delta-isomerase (ADI) activity.

The nucleic acid molecule may for instance be capable of hybridizing to a polynucleotide sequence having at least 50% sequence identity with the sequence of SEQ ID NO: 6, said polynucleotide sequence encoding a protein or fragment thereof having trans-aconitate decarboxylase (TAD) activity.

The nucleic acid molecule may for instance be capable of hybridizing to a polynucleotide sequence having at least 50% sequence identity with the sequence of SEQ ID NO: 4, said polynucleotide sequence encoding a protein or fragment thereof having the activity of a mitochondrial citrate transporter, preferably of a mitochondrial cis-aconitate transporter.

The nucleic acid molecule may for instance be capable of hybridizing to a polynucleotide sequence having at least 50% sequence identity with the sequence of SEQ ID NO: 3, said polynucleotide sequence encoding a protein or fragment thereof having the activity of a multidrug transporter of the major facilitator superfamily, preferably of a transporter which exports itaconic acid out of the host cell.

The nucleic acid molecule may for instance be capable of hybridizing to a polynucleotide sequence having at least 50% sequence identity with the sequence of SEQ ID NO: 8, said polynucleotide sequence encoding a protein or fragment thereof having the activity of a transcription factor for at least one of polynucleotide sequences of any one of SEQ ID NOs: 1, 3, 4, and/or 6.

In some embodiments a nucleic acid molecule of the invention is a sequence that is complementary to the sequence of an ADI (SEQ ID NO: 1 and/or 7), an ADI2 (SEQ ID NO: 17), a TAD (SEQ ID NO: 6), a CTP1 (SEQ ID NO: 4), a MFS (SEQ ID NO: 3), a transcription factor having activity for one of nucleic acids of SEQ ID NO: 1, 7, 3, 4, 6, 8 and/or 9, (e.g. UM05080; SEQ ID NO: 8) or a cytochrome P450-monooxygenase (e.g. UM05074; SEQ ID NO: 9). A nucleotide sequence is complementary to or the complement of another nucleotide sequence if all of the nucleotides of the first sequence are complementary to all of the nucleotides of the second sequence. Accordingly, the respective nucleotide sequence will specifically hybridise to, or undergo duplex formation with, the respective portion of the target nucleic acid molecule under suitable hybridisation assay conditions, in particular of ionic strength and temperature.

As an illustrative example, the respective nucleic acid sequence may be included in a single-stranded nucleic acid molecule. Such a single-stranded nucleic acid molecule may have a nucleic acid sequence that is at least partially complementary to at least a portion of a strand of the sequence of an ADI (SEQ ID NO: 1 and/or 7), an ADI2 (SEQ ID NO: 17), a TAD (SEQ ID NO: 6), a CTP1 (SEQ ID NO: 4), a MFS (SEQ ID NO:3), a transcription factor having activity for one of nucleic acids of SEQ ID NO: 1, 7, 3, 4, 6, 8 and/or 9 (e.g. UM05080; SEQ ID NO: 8) or a cytochrome P450 monooxygenase (e.g. UM05074; SEQ ID NO: 9). The respective nucleotide sequence may for example be 50, 60, 70, for example 80 or 85, including 100% identical to another nucleic acid sequence. The higher the percentage to which the two sequences are complementary to each other (i.e. the lower the number of mismatches), the easier will they form a complex by hybridization. In typical embodiments the respective nucleotide sequence is substantially complementary to at least a portion of the sequence of an ADI (SEQ ID NO: 1 and/or 7), an ADI2 (SEQ ID NO: 17), a TAD (SEQ ID NO: 6), a CTP1 (SEQ ID NO: 4), a MFS (SEQ ID NO: 3), transcription factor having activity for one of nucleic acids of SEQ ID NO: 1, 7, 3, 4, 6, 8 and/or 9 (e.g. UM05080; SEQ ID NO: 8) or a cytochrome P450-monooxygenase (e.g. UM05074; SEQ ID NO: 9). "Substantially complementary" as used in this document refers to the fact that a given nucleic acid sequence is at least 90% identical to another nucleic acid sequence. A substantially complementary nucleic acid sequence is in some embodiments about 95% or more identical to another nucleic acid sequence. The term "complementary" or "complement" refers to two nucleotides that can form multiple favourable interactions with one another. Such favourable interactions are specific association between opposing or adjacent pairs of nucleic acid (including nucleic acid analogue) strands via matched bases, and include Watson-Crick base pairing. As an illustrative example, in two given nucleic acid molecules (e.g. DNA molecules) the base adenosine is complementary to thymine or uracil, while the base cytosine is complementary to guanine.

Interactions between two or more nucleic acid molecules are generally sequence driven interactions referred to as hybridization. Sequence driven interaction is an interaction that occurs between two nucleotides or nucleotide analogs or nucleotide derivatives in a nucleotide specific manner (supra). Typically sequence driven interactions occur on the Watson-Crick face or Hoogsteen face of the respective nucleotide. The hybridization of two nucleic acid molecules is affected by a number of conditions and parameters known to those skilled in the art. For example, the concentrations of salts, pH, and temperature of the reaction all affect whether two nucleic acid molecules will hybridize. In some embodiments selective hybridization conditions can be defined as stringent hybridization conditions. For example, stringency of hybridization is controlled by both temperature and salt concentration of either or both of the hybridization and washing steps. For example, conditions of hybridization that achieve selective interactions between complementary sequences may involve hybridization in high ionic strength solution (6×SSC or 6×SSPE) at a temperature that is in the range from about 12 to about 25° C. below the $T_m$, the melting temperature at which half of the molecules of a sequence dissociate from hybridization partners that are a perfectly matched probe, followed by washing at a combination of temperature and salt concentration chosen so that the washing temperature is in the range from about 5° C. to about 20° C. below the $T_m$. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations than for DNA-DNA hybridizations.

A polynucleotide sequence of the invention may for instance be complementary to the sequence of SEQ ID NO: 7 or to the sequence of SEQ ID NO: 1. A polynucleotide sequence of the invention may be fully complementary to one of these sequences, i.e. have a sequence of nucleotides, where in the form of this sequence each of the nucleotides can undergo specific association such as Watson-Crick base pairing with a nucleotide in the sequence of SEQ ID NO: 7 or of SEQ ID NO: 1.

A nucleic acid molecule according to the present invention may also include a sequence that is capable of modulating transcription, also called transcriptional control elements suitable such as a promoter or an enhancer (supra). A nucleic acid molecule according to the present invention may also include a polyadenylation signal, a transcription pausing signal or a transcription termination signal. A sequence capable of modulating transcription, including a transcription termination site, may be operably linked to a polynucleotide sequence as described above. For proper expression of a respective polypeptide, a suitable translational control element may be operably linked to the encoding polynucleotide sequence, such as e.g. a suitable leader sequence, a non-translated region of an mRNA that is important for translation by the cell. The leader sequence is operably linked to the 5'-terminus of the nucleic acid sequence encoding the ADI. Any leader sequence, which is functional in the selected host cell, may be used in the context of the present invention. A further illustrative example of a suitable translational control element is a 5' untranslated region leading to a 5' cap structure suitable for recruiting ribosomes, and a stop codon to terminate the translation process. In some embodiments a nucleic acid molecule of the invention includes an expression cassette (cf. above). Such an expression cassette may for example have a sequence capable of modulating transcription, such as a promoter and/or a transcription termination site, operably linked to the sequence as described above. A nucleic acid molecule according to the present invention may be an isolated molecule, for example isolated from one or more cells or from tissue. A nucleic acid molecule of the invention may be a recombinant molecule. In some embodiments a nucleic acid molecule of the invention is included in a vector (supra).

The sequence of an ADI according to the invention encodes a biologically active polypeptide/protein in that such a polypeptide has activity of an aconitate-delta-isomerase. This cytoplasmic enzyme (EC 5.3.3.7) is involved in ITA formation by converting the TCA cycle intermediate cis-aconitic acid into trans-aconitic acid. The sequence of a TAD according to the invention encodes a biologically active polypeptide/protein in that such polypeptide has activity of a trans-aconitate decarboxylase (TAD). This cytoplasmic enzyme (no EC number attributed yet) catalyzes the second step of ITA formation by converting trans-aconitic acid into itaconic acid:

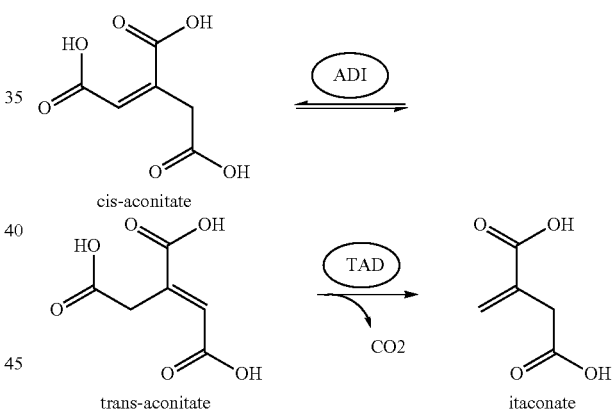

The conversion of cis-aconitate to ITA is in *A. terreus* the last step of a biosynthesis that includes the Embden-Meyerhof pathway followed by the TCA cycle. In *A. terreus* the enzyme CAD has the sequence of SwissProt/Uniprot accession No B3IUN8 (version 11 of 3 Oct. 2012), encoded by the gene of GenBank accession No DM010748 (version DM010748.1, GI: 224430794). Since ITA is not essential for the viability of *U. maydis*, it is regarded a secondary metabolite. Secondary metabolism genes are often arranged in clusters and are coregulated (cf. FIG. 1). Although the general enzyme activities implicated in ITA production are similar in *A. terreus* and *U. maydis*, the sequences of the genes or enzymes show little to no relation to each other. The present inventors found in cultivation experiments with the *U. maydis* strain deleted for the UM11778 gene that the enzyme encoded by this gene plays a crucial role in the ITA synthesis pathway. Its deletion almost completely disrupted the ITA production. In addition, deletion of UM05076 resulted in a total loss of ITA production, which indicates that both genes are essential in the ITA synthesis pathway of *U. maydis*. The deletion of the two other genes, UM06058 and UM02807, encoding proteins, which have a high sequence similarity to UM11778, did not result in any detectable decrease in ITA production.

The enzyme methylitaconate-Delta-isomerase (Mii), which shows 33% similarity to the *U. maydis* ADI, has previously been identified in *Eubacterium barkeri* (Velarde 2009). Although this Mii enzyme can catalyze the conversion of citraconate to itaconate, this activity is likely a side-activity of the main reaction, which is an isomerisation of methylitaconate into dimethylmaleate. To our knowledge, the Mii enzyme cannot convert cis-aconitate to ITA, and *Eubacterium* strains have not been implicated in ITA production.

With regard to nucleic acid sequences, the degeneracy of the genetic code permits substitution of certain codons by other codons that specify the same amino acid and hence would give rise to the same protein. The nucleic acid sequence can vary substantially since, with the exception of methionine and tryptophan, the known amino acids can be coded for by more than one codon. Thus, portions or all of the nucleic acid sequences described herein could be synthesized to give a nucleic acid sequence significantly different from that shown in their indicated sequence. The encoded amino acid sequence thereof would, however, be preserved.

A nucleic acid molecule according to the present invention may also include a polynucleotide sequence that is at least essentially identical to the sequence of SEQ ID NO: 3. The respective polynucleotide sequence may have at least 50% sequence identity with the sequence of SEQ ID NO: 3. The sequence of SEQ ID NO: 3 is believed to encode a protein that is involved in the export of methylenesuccinic acid from the cytosol of a cell expressing the protein (MFS transporter or MFS). In some embodiments the nucleic acid molecule of the invention is a recombinant nucleic acid molecule that includes the sequence of SEQ ID NO: 7 and the sequence of SEQ ID NO: 3. In some embodiments the nucleic acid molecule of the invention is a recombinant nucleic acid molecule that includes the sequence of SEQ ID NO: 1 and the sequence of SEQ ID NO: 3. In some embodiments the nucleic acid molecule of the invention is a recombinant nucleic acid molecule that includes the sequence of SEQ ID NO: 1 and/or SEQ ID NO: 7 and/or SEQ ID NO: 6 and the sequence of SEQ ID NO: 3.

In some embodiments a nucleic acid molecule according to the present invention includes a sequence that is at least essentially identical to the sequence of SEQ ID NO: 4. Such a polynucleotide sequence may have at least 50% sequence identity with the sequence of SEQ ID NO: 4. The sequence of SEQ ID NO: 4 is believed to encode a protein that is involved in the export of citrate or cis-aconitate from the mitochondria to the cytosol of a cell expressing the protein (CTP1). In some embodiments the nucleic acid molecule of the invention is a recombinant nucleic acid molecule that includes the sequence of SEQ ID NO: 1 and the sequence of SEQ ID NO: 4. In some embodiments the nucleic acid molecule of the invention is a recombinant nucleic acid molecule that includes the sequence of SEQ ID NO: 7 and the sequence of SEQ ID NO: 4. In some embodiments the nucleic acid molecule of the invention is a recombinant nucleic acid molecule that includes the sequence of SEQ ID NO: 1 and/or SEQ ID NO: 7 and/or SEQ ID NO: 6 and the sequence of SEQ ID NO: 4.

In some embodiments a nucleic acid molecule according to the invention includes a functional fragment of the sequence of SEQ ID NO: 3 or of the sequence of SEQ ID NO: 4. The functional fragment may be a polynucleotide sequence that includes a sequence of about 1000 contiguous bases of SEQ ID NO: 3 and of SEQ ID NO: 4, respectively. In some embodiments such a polynucleotide sequence may include a sequence of about 850 contiguous bases of SEQ ID NO: 3 and of SEQ ID NO: 4, respectively.

A nucleic acid molecule according to the present invention may also include a sequence that is at least essentially identical to the sequence of SEQ ID NO: 5. Such a polynucleotide sequence may have at least 50% sequence identity with the sequence of SEQ ID NO: 5. In some embodiments the nucleic acid molecule of the invention is a recombinant nucleic acid molecule that includes the sequence of SEQ ID NO: 1 and the sequence of SEQ ID NO: 5. In some embodiments the nucleic acid molecule of the invention is a recombinant nucleic acid molecule that includes the sequence of SEQ ID NO: 7 and the sequence of SEQ ID NO: 5. In some embodiments the nucleic acid molecule of the invention is a recombinant nucleic acid molecule that includes the sequence of SEQ ID NO: 1 and/or SEQ ID NO: 7 and/or SEQ ID NO: 6 and the sequence of SEQ ID NO: 5.

A nucleic acid molecule according to the present invention may also include a sequence that is at least essentially identical to the sequence of SEQ ID NO: 6. Such a polynucleotide sequence may have at least 50% sequence identity with the sequence of SEQ ID NO: 6. In some embodiments the nucleic acid molecule of the invention is a recombinant nucleic acid molecule that includes the sequence of SEQ ID NO: 1 and the sequence of SEQ ID NO: 6. In some embodiments the nucleic acid molecule of the invention is a recombinant nucleic acid molecule that includes the sequence of SEQ ID NO: 7 and the sequence of SEQ ID NO: 6. In some embodiments the nucleic acid molecule of the invention is a recombinant nucleic acid molecule that includes the sequence of SEQ ID NO: 1 and/or SEQ ID NO: 7 and/or SEQ ID NO: 6.

A nucleic acid molecule according to the present invention may also include a sequence that is at least essentially identical to the sequence of SEQ ID NO: 9. Such a polynucleotide sequence may have at least 50% sequence identity with the sequence of SEQ ID NO: 9.

A nucleic acid molecule according to the present invention may also include a sequence that is at least essentially identical to the sequence of SEQ ID NO: 8. Such a polynucleotide sequence may have at least 50% sequence identity with the sequence of SEQ ID NO: 8. In some embodiments the nucleic acid molecule of the invention is a recombinant nucleic acid molecule that includes the sequence of SEQ ID NO: 1 and the sequence of SEQ ID NO: 8. In some embodiments the nucleic acid molecule of the invention is a recombinant nucleic acid molecule that includes the sequence of SEQ ID NO: 7 and the sequence of SEQ ID NO: 8. In some embodiments the nucleic acid molecule of the invention is a recombinant nucleic acid molecule that includes the sequence of SEQ ID NO: 1 and/or SEQ ID NO: 7 and/or SEQ ID NO: 8. In some embodiments the nucleic acid molecule of the invention is a recombinant nucleic acid molecule that includes the sequence of SEQ ID NO: 6 and SEQ ID NO: 8. In some embodiments the nucleic acid molecule of the invention is a recombinant nucleic acid molecule that includes the sequence of SEQ ID NO: 6 and/or SEQ ID NO: 1 and/or SEQ ID NO: 7 and/or SEQ ID NO: 8.

A nucleic acid molecule according to the present invention may also include a sequence that is at least essentially identical to the sequence of SEQ ID NO: 1. Such a polynucleotide sequence may have at least 30%, 40%, or 50% sequence identity with the sequence of SEQ ID NO: 1.

A nucleic acid molecule according to the present invention may also include a sequence that is at least essentially identical to the sequence of SEQ ID NO: 7. Such a polynucleotide sequence may have at least 30%, 40%, or 50% sequence identity with the sequence of SEQ ID NO: 7.

Similarly, the present invention relates to a recombinant nucleic acid molecule comprising an expression cassette, the expression cassette comprising (i) a transcription regulating nucleotide sequence and (ii) a polynucleotide sequence
- having at least 30%, 40%, or 50% sequence identity with the sequence of SEQ ID NO: 1 or SEQ ID NO: 7 and encoding a polypeptide having ADI activity or
- capable of hybridizing under stringent conditions to the sequence of SEQ ID NO: 1 SEQ ID NO: 7 and (iii) a polynucleotide sequence
- having at least 50% sequence identity with the sequence of SEQ ID NO: 6 and encoding a polypeptide having TAD activity or
- capable of hybridizing under stringent conditions to the sequence of SEQ ID NO: 6.

The present invention also relates to a recombinant nucleic acid molecule comprising an expression cassette, the expression cassette comprising (i) a transcription regulating nucleotide sequence and (ii) a polynucleotide sequence having at least 30%, 40% or 50% sequence identity with any of the sequences of SEQ ID NO: 1, 3, 4, 6-9 and encoding a protein having ADI, MFS, CTP1, TAD, transcription factor having activity for one of nucleic acids of SEQ ID NO: 1, 7, 3, 4, 6, 8 and/or 9 (e.g. UM05080) or cytochrome P450-Monoxygenase activity, respectively or capable of hybridizing under stringent conditions to the sequence any of SEQ ID NO: 1, 3, 4, 6-9, respectively.

In some embodiments the polynucleotide sequence of a nucleic acid molecule of the invention is included in a nucleic acid molecule that further contains a polynucleotide sequence that is at least essentially identical to the sequence of SEQ ID NO: 6. The respective polynucleotide sequence may have at least 50% sequence identity with the sequence of SEQ ID NO: 6. In some embodiments the nucleic acid molecule of the invention is a recombinant nucleic acid molecule that includes the sequence of SEQ ID NO: 6 and the sequence of SEQ ID NO: 7. In some embodiments the nucleic acid molecule of the invention is a recombinant nucleic acid molecule that includes the sequence of SEQ ID NO: 6 and the sequence of SEQ ID NO: 1. In some embodiments the nucleic acid molecule of the invention is a recombinant nucleic acid molecule that includes the sequence of SEQ ID NO: 1 and/or SEQ ID NO: 7 and/or SEQ ID NO: 6 and the sequence of SEQ ID NO: 4.

In some embodiments a nucleic acid molecule according to the invention includes a functional fragment of the sequence of SEQ ID NO: 5 or of the sequence of SEQ ID NO: 6. The functional fragment may be a polynucleotide sequence that includes a sequence of about 1000 contiguous bases of SEQ ID NO: 5 and of SEQ ID NO: 6, respectively. In some embodiments such a polynucleotide sequence may include a sequence of about 850 contiguous bases of SEQ ID NO: 5 and of SEQ ID NO: 6, respectively.

In some embodiments a nucleic acid molecule according to the present invention includes a sequence that is at least essentially identical to the sequence of SEQ ID NO: 8 and/or a sequence that is at least essentially identical to the sequence of SEQ ID NO: 9. Such a polynucleotide sequence may have at least 50% sequence identity with the sequence of SEQ ID NO: 8, and with the sequence of SEQ ID NO: 9, respectively. In some embodiments the nucleic acid molecule of the invention is a recombinant nucleic acid molecule that includes the sequence of SEQ ID NO: 1 and the sequence of SEQ ID NO: 8. In some embodiments the nucleic acid molecule of the invention is a recombinant nucleic acid molecule that includes the sequence of SEQ ID NO: 7 and the sequence of SEQ ID NO: 8. In some embodiments the nucleic acid molecule of the invention is a recombinant nucleic acid molecule that includes the sequence of SEQ ID NO: 7 and the sequence of SEQ ID NO: 9. In some embodiments the nucleic acid molecule of the invention is a recombinant nucleic acid molecule that includes the sequence of SEQ ID NO: 7, the sequence of SEQ ID NO: 8 and the sequence of SEQ ID NO: 9. In some embodiments the nucleic acid molecule of the invention is a recombinant nucleic acid molecule that includes the sequence of SEQ ID NO: 1 and the sequence of SEQ ID NO: 9. In some embodiments a respective nucleic acid molecule is a recombinant nucleic acid molecule that includes the sequence of SEQ ID NO: 1, the sequence of SEQ ID NO: 8 and the sequence of SEQ ID NO: 9. In some embodiments the nucleic acid molecule of the invention is a recombinant nucleic acid molecule that includes the sequence of SEQ ID NO: 1 and/or SEQ ID NO: 7 and/or SEQ ID NO: 6 and SEQ ID NO: 8.

In some embodiments a nucleic acid molecule according to the invention includes a functional fragment of the sequence of SEQ ID NO: 8 or of the sequence of SEQ ID NO: 9. The functional fragment may be a polynucleotide sequence that includes a sequence of about 1000 contiguous bases of SEQ ID NO: 8 and of SEQ ID NO: 9, respectively. In some embodiments such a polynucleotide sequence may include a sequence of about 850 contiguous bases of SEQ ID NO: 8 and of SEQ ID NO: 9, respectively.

A polynucleotide sequence of the invention may in some embodiments be complementary, including at least essentially complementary, to the sequence of SEQ ID NO: 7 or to the sequence of SEQ ID NO: 1. A polynucleotide sequence of the invention may be fully complementary to one of these sequences, i.e. have a sequence of nucleotides, where in the form of this sequence each of the nucleotides can undergo specific association such as Watson-Crick base pairing with a nucleotide in the sequence of SEQ ID NO: 7 or of SEQ ID NO: 1.

A nucleic acid molecule of the invention may include a polynucleotide sequence that is complementary, including at least essentially complementary, to the sequence of SEQ ID NO: 3. In some embodiments a polynucleotide sequence of the invention is fully complementary to the sequence of SEQ ID NO: 3. In some embodiments a polynucleotide nucleic acid molecule of the invention includes a polynucleotide sequence that is complementary, including at least essentially complementary or fully complementary, to the sequence of SEQ ID NO: 4.

A polynucleotide sequence of the invention may in some embodiments be complementary, including at least essentially complementary or fully complementary, to the sequence of SEQ ID NO: 5. In some embodiments a polynucleotide nucleic acid molecule of the invention includes a polynucleotide sequence that is complementary, including at least essentially complementary or fully complementary, to the sequence of SEQ ID NO: 6. A nucleic acid molecule of the invention may also include a sequence that is complementary, including at least essentially complementary or fully complementary, to the sequence of SEQ ID NO: 5.

A polynucleotide sequence of the invention may in some embodiments be complementary, including at least essentially complementary or fully complementary, to the sequence of SEQ ID NO: 8. In some embodiments a polynucleotide nucleic acid molecule of the invention includes a polynucleotide sequence that is complementary, including at least essentially complementary or fully complementary, to the sequence of SEQ ID NO: 9.

A tag may be included into a polynucleotide sequence to allow identification and/or purification of the encoded protein. Examples of affinity tags that may be used in accordance with the invention include, but are not limited to, a streptavidin binding tag such as the STREP-TAGS® described in US patent application US 2003/0083474, U.S. Pat. No. 5,506,121 or 6,103,493, an immunoglobulin domain, maltose-binding protein, glutathione-S-transferase (GST), calmodulin binding peptide (CBP), FLAG-peptide (e.g. of the sequence Asp-Tyr-Lys-Asp-Asp-Asp-Asp-Lys-Gly, SEQ ID NO: 24), the T7 epitope (Ala-Ser-Met-Thr-Gly-Gly-Gln-Gln-Met-Gly, SEQ ID NO:25), maltose binding protein (MBP), the HSV epitope of the sequence Gln-Pro-Glu-Leu-Ala-Pro-Glu-Asp-Pro-Glu-Asp (SEQ ID NO: 26) of herpes simplex virus glycoprotein D, the Vesicular Stomatitis Virus Glycoprotein (VSV-G) epitope of the sequence Tyr-Thr-Asp-Ile-Glu-Met-Asn-Arg-Leu-Gly-Lys (SEQ ID NO: 27), the hemagglutinin (HA) epitope of the sequence Tyr-Pro-Tyr-Asp-Val-Pro-Asp-Tyr-Ala (SEQ ID NO: 28) and the "myc" epitope of the transcription factor c-myc of the sequence Glu-Gln-Lys-Leu-Ile-Ser-Glu-Glu-Asp-Leu (SEQ ID NO: 29). Further examples of a suitable tag include, but are not limited to, a HAT tag, c-myc, His (e.g., 6×His, SEQ ID NO: 30) tags, a TAP-tag, chitin binding domain, immunoglobulin A (IgA), intein and streptavidine binding protein (SBP) tag.

A nucleic acid molecule of the invention may further include a nucleotide sequence that encodes a marker protein. Such a marker protein may for instance confer resistance against an antibiotic or anti-metabolite.

A marker protein, in accordance with the invention, means a protein, which provides the transformed cells with a selection advantage (e.g. growth advantage, resistance against an antibiotic) by expressing the corresponding gene product. Marker genes code, for example, for enzymes causing a resistance to particular antibiotics. As used herein, the term "marker gene" refers to a gene the product of which confers a characteristic to the cell expressing the marker gene that allows it to be distinguished from cells that do not express the marker gene. In some embodiments, the marker gene allows screening and/or selection of cells. In some such embodiments, the marker gene is a "screenable marker" or a "selectable marker". Screening and/or selection may be accomplished based on the presence or absence of the marker. In some embodiments, the screenable or selectable marker confers resistance to an agent such as an antibiotic. In some embodiments, the screenable or selectable marker confers an ability that provides an advantage in a particular set of growth conditions over cells that do not express the screenable or selectable marker.

As described above, the selectable marker can be the expression product of a gene encoding a protein restoring prototrophy for an organic compound, also referred to as a prototrophy restoring gene. In this case, the selectable marker introduced enables the cell to synthesize the compound by itself so that it is no longer or less dependent on the external supply of said compound with the medium. Accordingly, a prototrophy restoring gene is a gene encoding an expression product, i.e. the selectable marker, which reduces or preferably abolishes the dependency of the host cell on external supply of an organic compound by facilitating its synthesis in the cell.

Selection for cells expressing said prototrophy restoring gene is carried out by culturing the cells on/in medium not containing the compound. Only cells expressing the prototrophy restoring gene will grow. The expression product of the gene may be a constituent of a synthesis pathway and the product produced by the constituent may have to be further processed in order to obtain the organic compound otherwise externally supplied. Prototrophy restoring genes commonly applied to plant or fungal cells are e.g. those expressing proteins conferring arginine prototrophy, tryptophan prototrophy, uridine prototrophy or genes enabling for nitrate or sulphate utilization. If the selectable marker is the expression product of a prototrophy restoring gene, the selecting agent is the medium in which the cell is cultivated and which does not contain the respective organic compound. Responsiveness in that case is expressed e.g. in growth rates of the cell. Thus, the higher the expression of the selectable marker, the higher the growth rate of the cell in the absence of the respective compound.

For some prototrophy restoring genes, the amount of expression product sufficient to result in prototrophy is very low. Accordingly, it is more laborious to distinguish cells expressing said prototrophy restoring selectable marker at a low level from those that express it at a high level. In order to facilitate said distinction, such a prototrophy restoring gene can be co-introduced together with a nucleic acid encoding a reporter gene the detectability of which is proportional to its expression level. Accordingly, in this embodiment, the selectable marker according to the invention is composed of the auxotrophy gene and the reporter gene.

Expression, Methods and Uses

A host cell used in the context of the present invention is typically capable of expressing a protein encoded by e.g. SEQ ID NO: 1 or any of SEQ ID NO: 3-9 such as a polypeptide molecule of SEQ ID NO: 2 or any of SEQ ID NO: 10-16, in that it includes a respective nucleic acid sequence, for example in the form of a functional gene of an ADI, TAD, MFS, CTP1 or a transcription factor (whether homologous or heterologous). In some embodiments, the host cell is capable of expressing a protein encoded by any combination of nucleic acids of the present invention. In other embodiments the host cell is able to express the proteins or protein combinations of the present invention. In some embodiments e.g. a nucleic acid molecule encoding a biologically active ADI has a nucleic acid sequence that has at least 70% sequence identity with the sequence of SEQ ID NO: 1 or the sequence of SEQ ID NO: 7. In some embodiments a respective, for instance identical, gene encoding a protein of e.g. SEQ ID NO: 1 or SEQ ID NO: 7 is functionally active and expressing a protein of e.g. SEQ ID NO: 2. In some embodiments an expression cassette, for instance heterologous, encoding an ADI protein is functionally active and expressing the respective protein. In some embodiments an endogenous nucleic acid sequence encoding a protein of e.g. SEQ ID NO: 2 is functionally inactive. In some of these embodiments a respective protein is nevertheless expressed—generally from a heterologous expression cassette. A heterologous gene or expression cassette encoding a corresponding protein may be introduced by means of recombinant technology, for instance by means of a vector carrying a gene encoding a protein of e.g.

SEQ ID NO: 2 (cf. also above). It may in this regard be advantageous to further use a vector that contains a promoter effective to initiate transcription in the respective host cell (whether of endogenous or exogenous origin).

In case the host cell is a fungal host cell that is an *Ustilago maydis* cell, suitable marker genes encode a resistance gene against hygromycin, G418, phleomycin, nourseothricin and carboxin.

A nucleic acid molecule of the invention may be included in a vector such as an expression vector. When included in a vector, typically a polynucleotide sequence of the invention is included in an expression cassette. An expression cassette as used in the context of the invention is typically driven by an expression control sequence, i.e. its expression is controlled by an expression control sequence which may be a constitutively active or inducible expression control sequence (such as a promoter) that is operatively linked with the expression cassette. A respective expression cassette is further designed such that it allows the expression of the incorporated nucleic acid sequence in selected host cells. For this purpose a respective expression cassette usually has the necessary regulatory sequences, such as a promoter and/or a transcription termination sequence such as a poly A site. A suitable host cell may for instance be a fungal host cell, such as a fungal host cell that is capable of filamentous growth in liquid culture or a cell of basidiomycetales, i.e. basidiomycetes. Typically the host cell does not secrete proteases, which take action on a protein of interest as described herein. In this regard the host cell may be a cell that has been manipulated so that any such proteases are inactivated, e.g., by knockout or pull-down by, e.g. iRNA or siRNA. As an illustrative example, where a fungal host cell or a yeast host cell is used, the cell may have an inactivated Kex2 protease, i.e. a Kex2-negative fungal or yeast host cell may be used. In some embodiments the fungi host cell is a cell of the class Saccharomycetes. Preferred are e.g. *Saccharomyces cerevisiae*, and *Pichia pastoris*. In other embodiments the host cell is a cell of the class Ustilaginomycetes or Eurotiomycetes, e.g. *Ustilago maydis* or *Aspergillus terreus*. In some embodiments where the host cell is *Ustilago maydis*, the protease that may be inactivated is Kex 2, encoded by the gene um02843 of SwissProt/Uniprot accession No Q4PAM0 (version 55 as of 3 Oct. 2012). The skilled person is aware of means and methods for inactivating any such protease. In case of *Ustilago maydis*, Kex2 can, for example, be knocked-out, either fully or partially, e.g., by homologous recombination. Other proteases that may be inactivated, either additionally or alternatively to Kex2, in *Ustilago maydis* are a secreted aspartic protease Um04926, designated Pep4; a lysosomal serine protease Um04400, designated Prb1 and/or a lysosomal tripeptidyl peptidase Um06118 of SwissProt/Uniprot accession No Q4P195 (version 36 as of 5 Sep. 2012).

Any desired restriction endonuclease site may be incorporated into an expression cassette and/or vector according to the invention. Typically the expression cassette includes at least one restriction enzyme recognition site at about the 3'-end and at least one restriction enzyme recognition site at about the 5'-end. As an example, a sequence cassette may be created enzymatically (e.g., by using a type I or type II restriction endonuclease or exonuclease), by mechanical means such as shearing, by chemical synthesis, or by a recombinant method such as PCR. An expression cassette usually includes the following elements (presented in the 5'-3' direction of transcription): a transcriptional and translational initiation region, a coding sequence for a gene of interest, and a transcriptional and translational termination region functional in the organism where it is desired to express the gene of interest.

Any desired protein expression system may be employed to generate a polypeptide according to the invention. In some embodiments a bacterial, a fungal or a mammalian cell expression system may be used. In one embodiment the cell is a cell of a fungus of the order Ustilaginales. As explained above, a host cell may in some embodiments be a fungus or a yeast that includes a nucleic acid molecule as described above, including an expression cassette or a vector described herein. A large number of suitable methods exist in the art to produce polypeptides (or fusion proteins) in host cells. Conveniently, the produced protein is harvested from the culture medium (medium), lysates of the cultured host cell or from isolated (biological) membranes by established techniques. For example, the expression cassettes as described herein comprising, inter alia, the nucleotide sequence encoding the protein of interest can be synthesized by PCR and inserted into an expression vector. Subsequently a cell produced with the method of the present invention may be transformed with the expression vector. Thereafter, the cell is cultured to produce/express the desired protein(s), which is/are isolated and purified. For example, the product may be recovered from the host cell and/or culture medium by conventional procedures including, but not limited to, cell lysis, breaking up host cells, centrifugation, filtration, ultra-filtration, extraction or precipitation. Purification may be performed by a variety of procedures known in the art including, but not limited to, chromatography (e.g. ion exchange, affinity, hydrophobic, chromatofocussing, and size exclusion), electrophoretic procedures (e.g., preparative isoelectric focusing), differential solubility (e.g. ammonium sulphate precipitation) or extraction.

In embodiments where a nucleic acid sequence of the invention is included in a eukaryotic expression cassette the expression cassette usually includes a polyadenylation site. Most eukaryotic nascent mRNAs possess a polyA-tail at their 3' end which is added during a complex process that involves cleavage of the primary transcript and a coupled polyadenylation reaction. The polyA-tail is advantageous for mRNA stability and transferability.

When a polypeptide of interest or of the present invention is expressed in a selected host cell, it may be necessary to modify the nucleotide sequence encoding the polypeptide by adapting the codon usage of the nucleotide sequence to meet the frequency of the preferred codon usage of the respective host cell. In this regard, "frequency of preferred codon usage" refers to the preference exhibited by the host cell of the invention in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A=n=1ZX_n-Y_nX_n$ times 100 Z where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage, A, for all amino acids should preferably be less than about 25%, such as less than about 10%.

Allowing a host cell to express a protein encoded by a sequence as defined above or a protein of the present invention may include fermenting a medium that includes a carbon source such as a carbohydrate-based carbon source, e.g. starch, a molasse such as sugar cane molasse, a hydrolysate of e.g. corn syrup or wood, (cf. also above) with a transformed cell as defined above. The cell may be allowed to ferment the carbon source to itaconic acid. An example of a suitable fermentation process is an aerobic fermentation process. An aerobic fermentation process according to an embodiment of the invention may be run under aerobic oxygen-limited conditions. As an example, in an aerobic process under oxygen-limited conditions, the rate of oxygen consumption is at least 5.5, including at least 6 or at least 7 mmol/L/h. The fermentation process may be a submerged or a solid state fermentation process. Itaconic acid may be produced via submerged fermentation starting from a carbohydrate raw material such as for instance cassava and/or corn, which may be milled and mixed with water. A seed fermentation may be prepared in a separate fermenter. The liquefaction of the starch may be performed in the presence of an amylolytic enzyme such as for instance an amylase, a cellulase, a lactase or a maltase and one or more additives and nutrients such as antifoam may be added before or during fermentation.

Culturing a cell that includes a nucleic acid molecule having a polynucleotide sequence that is at least essentially identical to a polynucleotide sequence as described above, e.g. the sequence of SEQ ID NO: 1 or SEQ ID NO: 7 and/or SEQ ID NO: 6, may be carried out in any suitable device such as a conventional stirred tank reactor, a bubble column, a tubular reactor, or an air-lift reactor.

Once expressed by a host cell, the itaconic acid may be recovered. It may be isolated by lysis or any other measure applied to break the cell membrane and/or cell wall of a host cell and subsequently be purified. However, a convenient way to harvest a protein of interest is its isolation from the culture medium. In that case, the protein of interest must be secreted by the host. Secretion of a protein is usually achieved by the use of signal sequences. Specifically, proteins equipped with a signal sequence are secreted through the conventional endoplasmic reticulum (ER)-Golgi secretory pathway, i.e., the conventional secretion pathway. However, some proteins, for example, cytoplasmic, nuclear and signal-peptide-containing proteins have been shown to reach the cell surface by non-conventional transport pathways. The mechanisms and molecular components of unconventional protein secretion are beginning to emerge. Unconventional protein secretion may have some advantages vis-à-vis conventional protein secretion, since proteins subject to unconventional secretion are not processed by ER or Golgi-dependent post-translational modifications.

In a method or use of the invention a nucleic acid may be introduced into a host cell by any suitable technique of nucleic acid delivery for transformation of a cell available in the art. Examples of suitable techniques include, but are not limited to, direct delivery of DNA, e.g. via transfection, injection, including microinjection, electroporation, calcium phosphate precipitation, by using DEAE-dextran followed by polyethylene glycol, direct sonic loading, liposome mediated transfection, receptor-mediated transfection, microprojectile bombardment, agitation with silicon carbide fibers, *Agrobacterium*-mediated transformation, desiccation/inhibition-mediated DNA uptake or any combination thereof. As indicated above, any desired host cell may be selected, for example a cell of a fungus of the order Ustilaginales.

A polypeptide of the invention may consist of the twenty conventional amino acids. In some embodiments a polypeptide of the invention may include stereoisomers (e.g., D-amino acids) of the twenty conventional amino acids, unnatural amino acids such as $\alpha,\alpha$-disubstituted amino acids, N-alkyl amino acids, and other unconventional amino acids may also be suitable components for a polypeptide according to the present invention. Examples of unconventional amino acids include: 4-hydroxyproline, Y-carboxyglutamate, N,N,N-trimethyllysine, E-N-acetyllysine, O-phosphoserine, N-acetylserine, N-formylmethionine, 3-methylhistidine, 5-hydroxylysine, s-N-methylarginine, and other similar amino acids and imino acids such as 4-hydroxyproline. In the polypeptide notation used in this document, the left-hand direction is the amino terminal direction and the right hand direction is the carboxy-terminal direction, in accordance with standard usage and convention.

The present invention provides a method of producing itaconic acid, the method comprising culturing a cell that comprises polynucleotide sequences having at least 50% sequence identity with the sequence of SEQ ID NO: 1 and/or SEQ ID NO: 7 and SEQ ID NO: 6 allowing the host cell to express or overexpress the polynucleotide sequences, forming a polypeptides that have activity of an ADI and a TAD, thereby producing itaconic acid. In some embodiments, the method further comprises a cell further comprising a polynucleotide sequence of SEQ ID NO: 4. In some embodiments, the method further comprises a cell further comprising a polynucleotide sequence of SEQ ID NO: 3. In some embodiments, the method further comprises a cell further comprising a polynucleotide sequence of SEQ ID NO: 8. In some embodiments, the method includes a cell overexpressing polynucleotides of any of the SEQ ID NO: 1, 3-9 in comparison to a wildtype cell. In some embodiments, the method includes a cell with a decreased expression or deletion of the polynucleotide sequence of SEQ ID NO: 9 in comparison to a wildtype cell.

The recombinant host cell of the present invention is engineered to overexpress
(i) a polynucleotide sequence having at least 30%, 40%, or 50% sequence identity with the sequence of SEQ ID NO: 1 or SEQ ID NO: 17, said polynucleotide sequence encoding a protein or fragment thereof having aconitate-delta-isomerase (ADI) activity; and
(ii) a polynucleotide sequence having at least 50% sequence identity with the sequence of SEQ ID NO: 6, said polynucleotide sequence encoding a protein or fragment thereof having trans-aconitate decarboxylase (TAD) activity.

The recombinant host cell of the present invention can also be engineered to overexpress
(i) a polynucleotide sequence having at least 30%, 40%, or 50% sequence identity with the sequence of SEQ ID NO: 7 or SEQ ID NO: 17, said polynucleotide sequence encoding a protein or fragment thereof having aconitate-delta-isomerase (ADI) activity; and
(ii) a polynucleotide sequence having at least 50% sequence identity with the sequence of SEQ ID NO: 6, said polynucleotide sequence encoding a protein or fragment thereof having trans-aconitate decarboxylase (TAD) activity.

The recombinant host cell of the present invention also includes a recombinant host cell that is engineered to overexpress a polynucleotide sequence having at least 30%, 40%, or 50% sequence identity with the sequence of SEQ ID NO: 1 or SEQ ID NO: 17, said polynucleotide sequence encoding a protein or fragment thereof having aconitate-delta-isomerase (ADI) activity.

The recombinant host cell of the present invention also includes a recombinant host cell that is engineered to overexpress a polynucleotide sequence having at least 50% sequence identity with the sequence of SEQ ID NO: 6, said polynucleotide sequence encoding a protein or fragment thereof having trans-aconitate decarboxylase (TAD) activity.

The recombinant host cell of the present invention also includes a recombinant host cell that is engineered to overexpress polynucleotide sequences having at least 30%, 40%, or 50% sequence identity with the sequence of SEQ ID NO: 71 or SEQ ID NO: 17, said polynucleotide sequence encoding a protein or fragment thereof having aconitate-delta-isomerase (ADI) activity.

The recombinant host cell of the present invention also includes a recombinant host cell that is engineered to overexpress polynucleotide sequences having at least 50% sequence identity with the sequence of SEQ ID NO: 3, said polynucleotide sequence encoding a protein or fragment thereof having MFS activity.

The recombinant host cell of the present invention also includes a recombinant host cell that is engineered to overexpress polynucleotide sequences having at least 50% sequence identity with the sequence of SEQ ID NO: 4, said polynucleotide sequence encoding a protein or fragment thereof having CTP1 activity.

The recombinant host cell of the present invention also includes a recombinant host cell that is engineered to overexpress polynucleotide sequences having at least 50% sequence identity with the sequence of SEQ ID NO: 8, said polynucleotide sequence encoding a protein or fragment thereof having transcription factor activity. Preferably, the transcription factor has activity for one of nucleic acids of SEQ ID NO: 1, 7, 3, 4, 6, 8 and/or 9, as for example, UM05080.

The recombinant host cell of the present invention also includes a recombinant host cell that is engineered to under-express polynucleotide sequences having at least 50% sequence identity with the sequence of SEQ ID NO: 9 said polynucleotide sequence encoding a protein or fragment thereof having P450-Monoxygenase (UM05074) activity.

The recombinant host cell of the present invention can be engineered to overexpress
(i) a polypeptide sequence having at least 30%, 40%, or 50% sequence identity with the sequence of SEQ ID NO: 2 and/or SEQ ID NO: 10 and/or SEQ ID NO: 18, wherein the polypeptide has ADI activity; and
(ii) a polypeptide sequence having at least 50% sequence identity with the sequence of SEQ ID NO: 13, wherein the polypeptide has TAD activity.

The recombinant host cell of the present invention can be engineered to overexpress a polypeptide sequence having at least 30%, 40%, or 50% sequence identity with the sequence of SEQ ID NO: 2 or SEQ ID NO: 18, wherein the polypeptide has ADI activity.

The recombinant host cell of the present invention can be engineered to overexpress a polypeptide sequence having at least 30%, 40%, or 50% sequence identity with the sequence of SEQ ID NO: 10 or SEQ ID NO: 18, wherein the polypeptide has ADI activity.

The recombinant host cell of the present invention can be engineered to overexpress a polypeptide sequence having at least 50% sequence identity with the sequence of SEQ ID NO: 13, wherein the polypeptide has TAD activity.

The recombinant host cell of the present invention can be engineered to underexpress a polypeptide sequence having at least 50% sequence identity with the sequence of SEQ ID NO: 11, wherein the polypeptide has P450-Monoxygenase (UM05074) activity.

The recombinant host cell of the present invention can be engineered to overexpress a polypeptide sequence having at least 50% sequence identity with the sequence of SEQ ID NO: 14, wherein the polypeptide has MFS activity.

The recombinant host cell of the present invention can be engineered to overexpress a polypeptide sequence having at least 50% sequence identity with the sequence of SEQ ID NO: 15, wherein the polypeptide has CTP1 activity.

The recombinant host cell of the present invention can be engineered to overexpress a polypeptide sequence having at least 50% sequence identity with the sequence of SEQ ID NO: 11, wherein the polypeptide has transcription factor (UM05080) activity.

In a method or use of generating itaconic acid (methylenesuccinic acid) according to the invention a recombinant nucleic acid molecule as defined above is employed, for example including an expression cassette. As an example and as explained above, in some embodiments the recombinant nucleic acid molecule includes a polynucleotide sequence, e.g. a heterologous polynucleotide sequence, that has at least 30%, 40%, or 50% identity with the sequence of SEQ ID NO: 1 or SEQ ID NO: 17 or at least 50% identity with the sequence of any of SEQ ID NO: 3-9. In some embodiments the recombinant nucleic acid molecule includes a polynucleotide sequence that differs from the sequence of SEQ ID NO: 1 or SEQ ID NO: 17 and/or from any of the sequence of SEQ ID NO: 3-9 in at least one nucleotide position. In some embodiments the recombinant nucleic acid molecule includes a polynucleotide sequence that has at least 70% identity with any of the sequence of SEQ ID NO: 1, 3-9, 17. The recombinant nucleic acid molecule may also include a polynucleotide sequence that has at least 80% identity with the sequence of SEQ ID NO: 1 or SEQ ID NO: 17 or any of sequence of SEQ ID NO: 3-9. The recombinant nucleic acid molecule may also include a polynucleotide sequence that has at least 85% identity with the sequence of SEQ ID NO: 1 or SEQ ID NO: 17 or any of sequence of SEQ ID NO: 3-9. The recombinant nucleic acid molecule may also include a polynucleotide sequence that has at least 90% identity with the sequence of SEQ ID NO: 1 or SEQ ID NO: 17 or any of sequence of SEQ ID NO: 3-9. The recombinant nucleic acid molecule may also include a polynucleotide sequence that has at least 95% identity with the sequence of SEQ ID NO: 1 or SEQ ID NO: 17 or any of sequence of SEQ ID NO: 3-9. The recombinant nucleic acid molecule may also include a polynucleotide sequence that has at least 99% identity with the sequence of SEQ ID NO: 1 or SEQ ID NO: 17 or any of sequence of SEQ ID NO: 3-9.

The recombinant nucleic acid molecule may include a further polynucleotide sequence as described above. In some embodiments a plurality such as two, three or more recombinant nucleic acid molecules as defined above are used. Each recombinant nucleic acid molecule of such a plurality may include one or more polynucleotide sequences as described above. For example, a sequence included in a nucleic acid molecule used may have at least 70% identity with the sequence of SEQ ID NO: 3 or with the sequence of SEQ ID NO: 4. In one embodiment a recombinant nucleic acid molecule is used that includes a sequence that is at least essentially identical to the sequence of SEQ ID NO: 5 or to the sequence of SEQ ID NO: 6. As a further example a sequence included in a recombinant nucleic acid molecule used may have at least 70% identity with the sequence of SEQ ID NO: 8 or with the sequence of SEQ ID NO: 9. In some embodiments the recombinant nucleic acid molecule includes a polynucleotide sequence that differs from the sequence of SEQ ID NO: 3, the sequence of SEQ ID NO: 4, the sequence of SEQ ID NO: 5, the sequence of SEQ ID NO: 6 and/or from the sequence of SEQ ID NO: 7 in at least one nucleotide position. In some embodiments the recombinant nucleic acid molecule includes a polynucleotide sequence that differs from the sequence of SEQ ID NO: 8 and/or from the sequence of SEQ ID NO: 9 in at least one nucleotide position.

The nucleic acid molecule may be included in a host cell as described above. Where a host cell contains the nucleic acid molecule, the host cell is cultured. The respective conditions for culturing the host cell depend on the selected type of cell and are within the knowledge of the skilled person. The host cell is allowed to express the polynucleotide sequence, so that a polypeptide is forming that is encoded by the sequence included in the recombinant nucleic acid molecule. The polypeptide may for instance have activity of a CAD. Typically the methylenesuccinic acid formed is isolated from the medium in which the cell is cultured (supra).

A method or use of producing itaconic acid may be a method of producing nitrilon. A method or use of producing itaconic acid may also be a method of manufacturing paper. In some embodiments a method or use of producing itaconic acid is a method of biofuel production or a method of wastewater treatment. In a method or use of producing itaconic acid typically the recombinant nucleic acid molecule is typically included in a host cell (supra). In typical embodiments the cell is provided with a suitable carbon source such as a monosaccharide, a polysaccharide, a polyol such as sorbitol, xylitol or mannitol, a lipid such as triacylglycerol or a fatty acid. Examples of a suitable monosaccharide include, but are not limited to, mannose, glucose, arabinose and xylose. Examples of a suitable polysaccharide include, but are not limited to, starch, a mannan and cellulose. Illustrative examples of a suitable fatty acid are omega-3 and/or omega-6 polyunsaturated fatty acids including decosahexaenoic acid or eicosapentaenoic acid, as well as palmitoleic acid, oleic acid or citric acid.

Kit

Reagents needed or useful in the context of the present invention may be provided in the form of a kit. Such a kit may in particular include means for expression of one or more genes as described in the present document. Means for expressing a biomarker are known in the art, and may include, for example, the use of suitable host cell and a nucleic acid molecule, for example included in an expression vector, carrying a sequence of a gene described above. In some embodiments a respective nucleic acid molecule according to the invention has a nucleic acid sequence that has at least 90% sequence identity with the sequence of SEQ ID NO: 3. A nucleic acid molecule according to the invention may also have a nucleic acid sequence that has at least 90% sequence identity with the sequence of SEQ ID NO: 4 or the sequence of SEQ ID NO: 5. The kit may include a first container that has a host cell such as a fungal host cell as described above. The kit may include a second container that has a nucleic acid molecule, such as a nucleic acid molecule described above. A nucleic acid molecule according to the invention may also have a nucleic acid sequence that has at least 90% sequence identity with the sequence of SEQ ID NO: 6 or the sequence of SEQ ID NO: 7. Typically the second container includes a nucleic acid molecule with a sequence that is at least essentially identical to the sequence of SEQ ID NO: 1 or the sequence of SEQ ID NO: 7 or the sequence of SEQ ID NO: 17. One or more further containers may be included in the kit that contain(s) a nucleic acid molecule with a sequence that is at least essentially identical to the sequence of SEQ ID NO: 3, SEQ ID NO: 4, SEQ ID NO: 5, SEQ ID NO: 6, of SEQ ID NO: 7, SEQ ID NO: 8, SEQ ID NO: 17 or the sequence of SEQ ID NO: 9. In some embodiments a nucleic acid molecule according to the invention has a nucleic acid sequence that has at least 90% sequence identity with the sequence of SEQ ID NO: 8 or with the sequence of SEQ ID NO: 9.

In some embodiments the kit may also include a reagent that allows the detection of a detectable label, which may be expressed in the form of a tag, attached to/fused to a protein encoded by a nucleic acid molecule of the invention. As an illustrative example, the detectable label may be an enzyme and the reagent may be a substrate of the enzyme. The substrate may for instance be converted by such enzyme into a product that emits a signal such as a fluorescent or a colour signal. In some embodiments the kit may include a binding partner directed to a protein encoded by a sequence as defined above. A respective binding partner may be an antibody, such as an immunoglobulin, a fragment of an immunoglobulin or a proteinaceous binding molecule with immunoglobulin-like functions. In one embodiment the kit includes components for setting up a method of detecting the expression of a nucleic acid sequence as defined above.

The kit may further include instructions and/or imprint indicating on how to express a nucleic acid molecule contained in the kit, as well as—where applicable—how to detect the expressed product. The kit may also include positive and/or negative controls, which allow a comparison to the control.

The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the appending claims. In addition, where features or aspects of the invention are described in terms of Markush groups, those skilled in the art will recognize that the invention is also thereby described in terms of any individual member or subgroup of members of the Markush group.

The invention is further illustrated by the following non-limiting examples. As one of ordinary skill in the art will readily appreciate from the disclosure of the present invention, other compositions of matter, means, uses, methods, or steps, presently existing or later to be developed that perform substantially the same function or achieve substantially the same result as the corresponding exemplary embodiments described herein may likewise be utilized according to the present invention.

EXAMPLES

Generation of UM05076 and UM11778 Deletion Mutants in *Ustilago maydis*

Figure 5A:
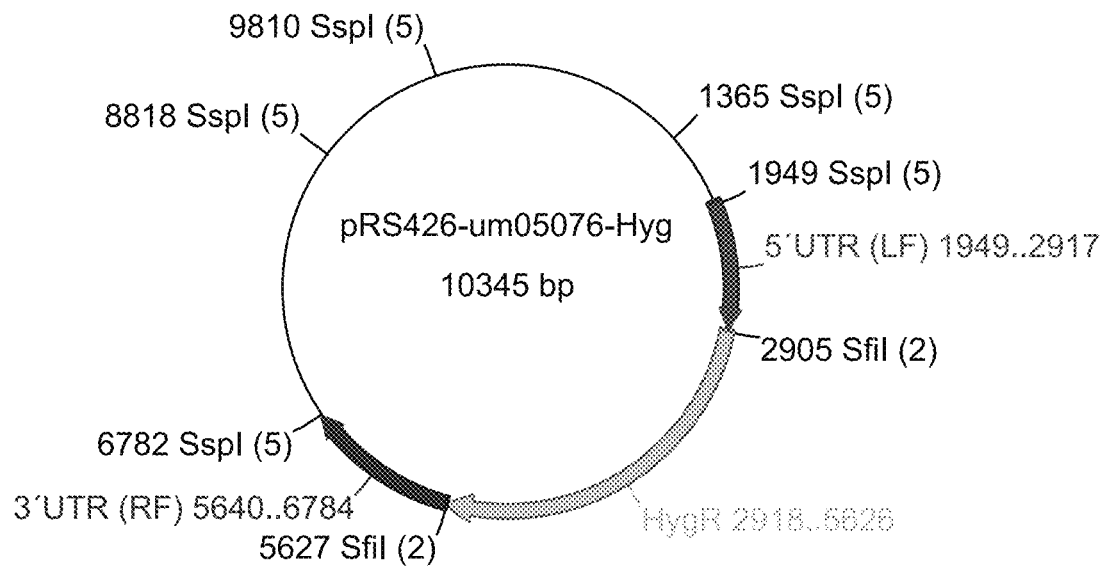
FIG. 5 Generation of UM05076 deletion mutant (A) Plasmid map of pRS426-um05076-hyg. (B) Outline of the region around the UM05076 gene in the *U. maydis* genome and the deletion construct integrated into the *U. maydis* genome by homologous recombination.
Figure 5B:
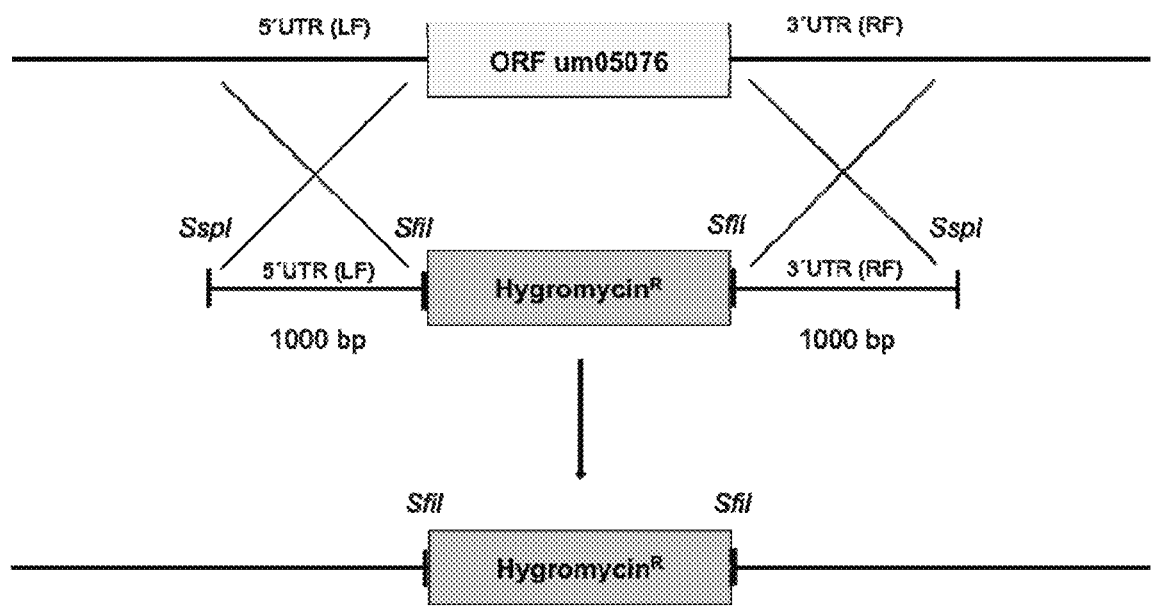
Figure 6A:
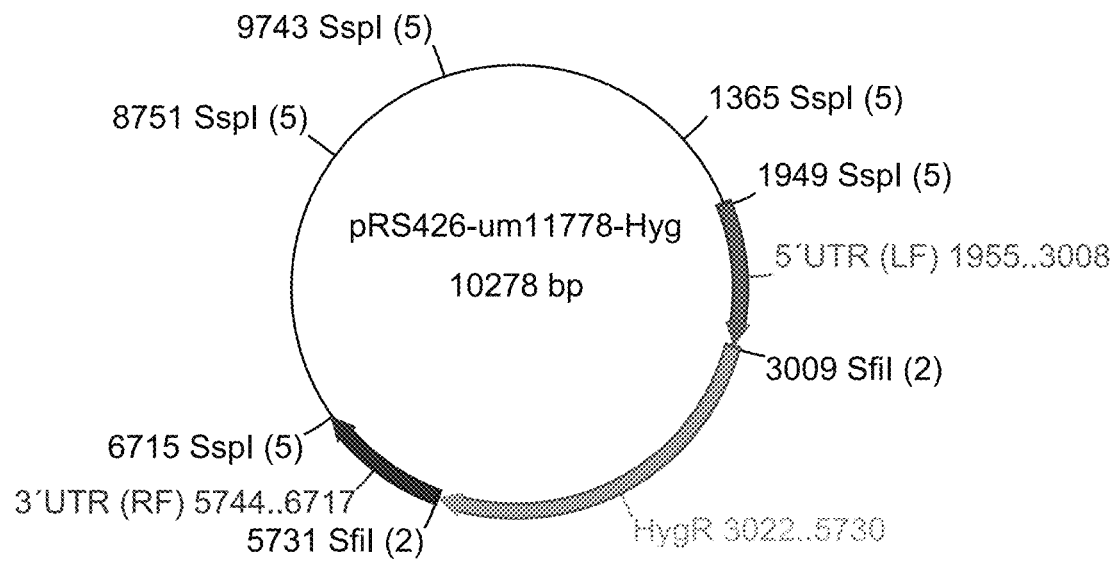
FIG. 6 Generation of UM11778 deletion mutant (A) Plasmid map of pRS426-um11778-hyg. (B) Outline of the region around the UM11778 gene in the *U. maydis* genome and the deletion construct integrated into the *U. maydis* genome by homologous recombination.
Figure 6B:
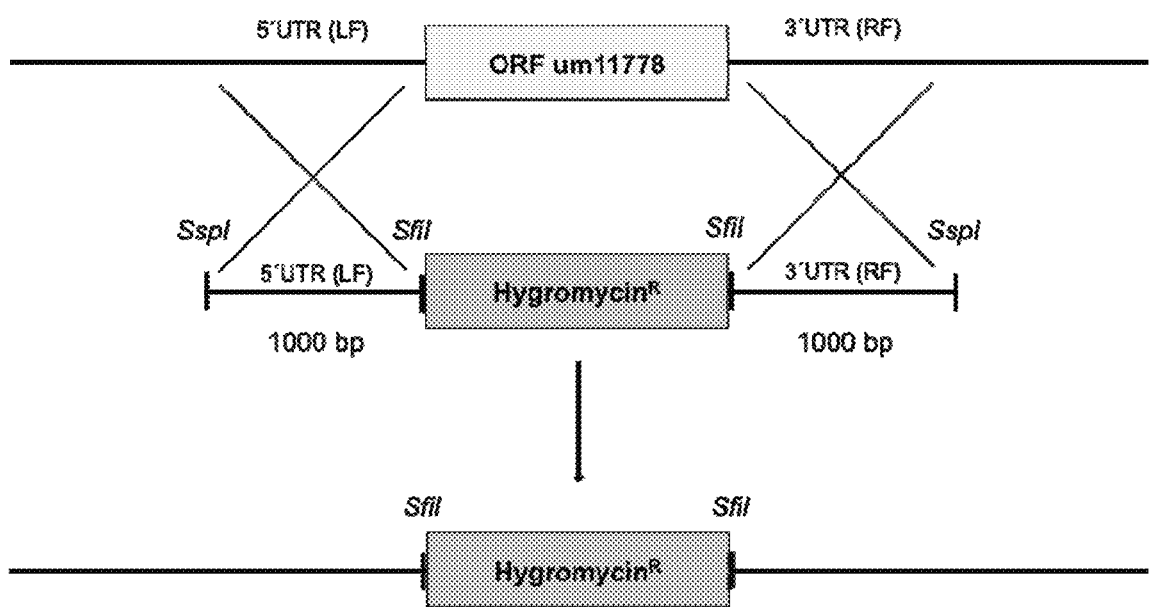
Figure 7:
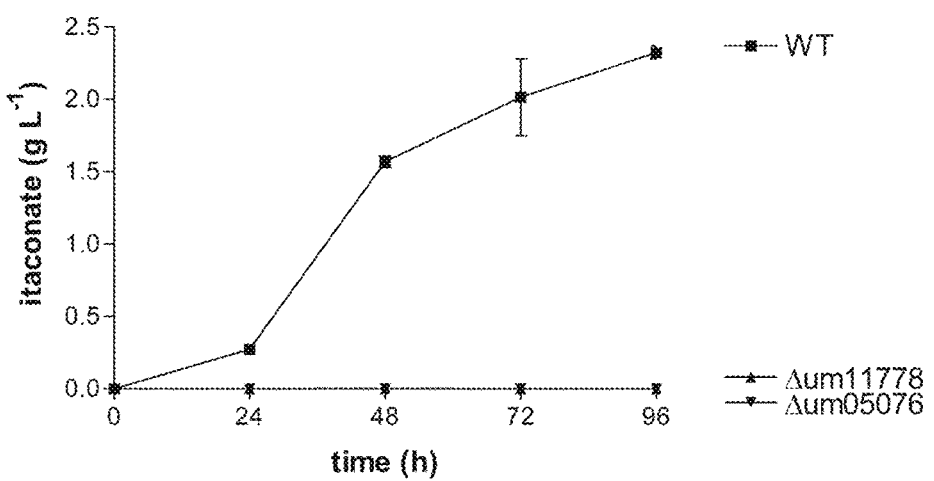
FIG. 7 shows the production kinetics of ITA from *U. maydis* MB215 wildtype and deletion mutants ΔUM11778 and ΔUM05076 in 50 ml MTM containing 50 gl$^{-1}$ glucose, 0.8 gl$^{-1}$NH$_4$Cl and 19.5 g L$^{-1}$ 2-(N-morpholino)ethanesulfonic acid (MES) (n=2; the values are mean of two analytical determinations)

The deletion constructs were constructed by using the yeast drag and drop method [Jansen et al. (2005) Gene 344:43-51]. For the deletion of UM05076, the shuttle vector pRS426 was combined with the left flank (5'UTR) and the right flank (3'UTR) of UM05076, respectively, as well as a hygromycin cassette derived from pMF1-h [Brachmann, A, et al. (2004) Mol Gen Genomics 272: 216-226]. For the deletion of UM11778, the shuttle vector pRS426 was combined with the left flank (5'UTR) and the right flank (3'UTR) of UM11778, respectively, as well as a hygromycin cassette derived from pMF1-h. Plasmid maps are shown in FIG. 5 and FIG. 6.

Vector pRS426-UM05076-Hyg was restricted with SspI to obtain the deletion-construct. Afterwards *U. maydis* strain MB215 was transformed with this construct, leading to genomic integration via homologous recombination. Disruption of UM05076 was checked by Southern blot analysis using HindIII as restriction enzyme for the genomic DNA and the right flank of UM05076 as a probe for radioactive labeling.

The resulting mutants were assessed for itaconate production in System Duetz® 24 well plates (Duetz et al. Applied and Environmental Microbiology, 2000, 66(6): 2641-2646) with a filling volume of 1.5 mL (d=50 mm, n=300 rpm, T=30° C. and Φ=80%) or in 500 ml Erlenmeyer flasks with a filling volume of 50 ml (d=25 mm, n=250 rpm, T=30° C. and Φ=80%). The screening medium contained 50 g L$^{-1}$ glucose, 0.8 g L$^{-1}$ NH$_4$Cl, 0.2 g L$^{-1}$ MgSO$_4$.7H$_2$O, 0.01 g L$^{-1}$ FeSO$_4$.7H$_2$O, 0.5 g L$^{-1}$ KH$_2$PO$_4$, 1 mL L$^{-1}$ vitamin solution, 10 mL L$^{-1}$ trace element solution and as buffer 19.5 g L$^{-1}$ 2-(N-morpholino)ethanesulfonic acid (MES). The pH of the MES stock solution was adjusted to 6.5 with NaOH. The vitamin solution contained (per liter) 0.05 g D-biotin, 1 g D-calcium panthotenate, 1 g nicotinic acid, 25 g myo-inositol, 1 g thiamine hydrochloride, 1 g pyridoxol hydrochloride and 0.2 g para-aminobenzoic acid. The trace element solution contained (per liter) 1.5 g EDTA, 0.45 g ZnSO$_4$.7H$_2$O, 0.10 g MnCl$_2$.4H$_2$O, 0.03 g CoCl$_2$.6H$_2$O, 0.03 g CuSO$_4$.5H$_2$O, 0.04 g Na$_2$MoO$_4$.2H$_2$O, 0.45 g CaCl$_2$.2H$_2$O, 0.3 g FeSO$_4$.7H$_2$O, 0.10 g H$_3$BO$_3$ and 0.01 g KI. Itaconate in the supernatant was analyzed in a Beckman Coulter System Gold High Performance Liquid Chromatography (Beckman Coulter GmbH, Germany) with an Organic Acid Resin 300×8 mm column (CS-Chromatography, Germany) and a differential refractometer LCD 201 (MELZ, Germany). As solvent, 5 mM H$_2$SO$_4$, with a flow rate of 0.6 mL min$^{-1}$ and a temperature of 30° C., was used. All samples were filtered with Rotilabo® syringe filters (CA, 0.20 μm, Ø15 mm) and afterwards 1:5 diluted with 5 mM H$_2$SO$_4$.

Figure 2:
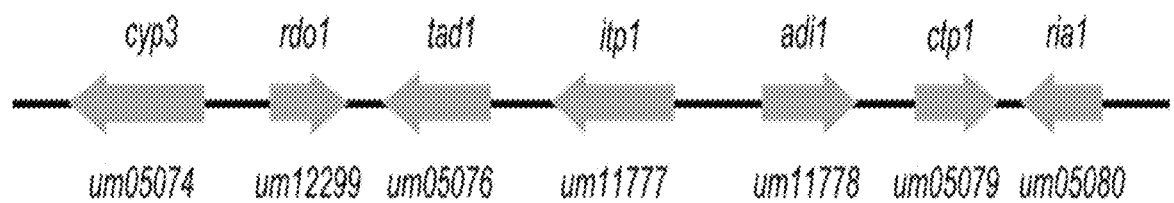
FIG. 2 lists the genes of the itaconic acid cluster in *U. maydis* and the effects of their deletion/overexpression. -- strongly decreased production; − decreased production; 0 no effect; + increased production; ++ strongly increased production.
Figure 3A:
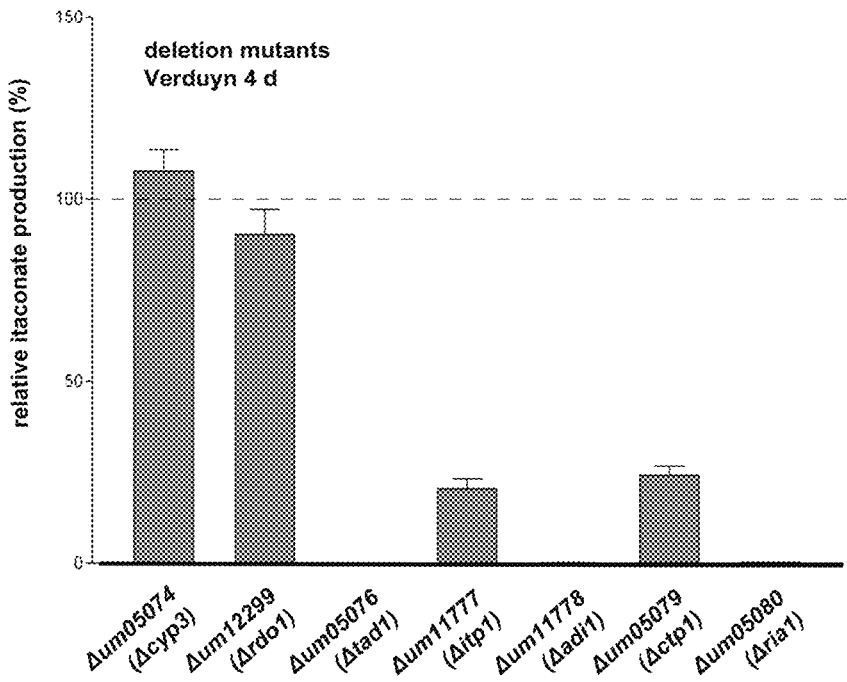
FIG. 3 illustrates relative itaconic acid production by *Ustilago maydis* MB215 strains carrying either mutations or overexpression constructs of itaconic acid biosynthesis genes. Itaconic acid production of wild type cells was set to 100%. (A) MB215 carrying deletions for indicated genes. (B) MB215 carrying overexpression constructs for indicated genes.
Figure 3B:
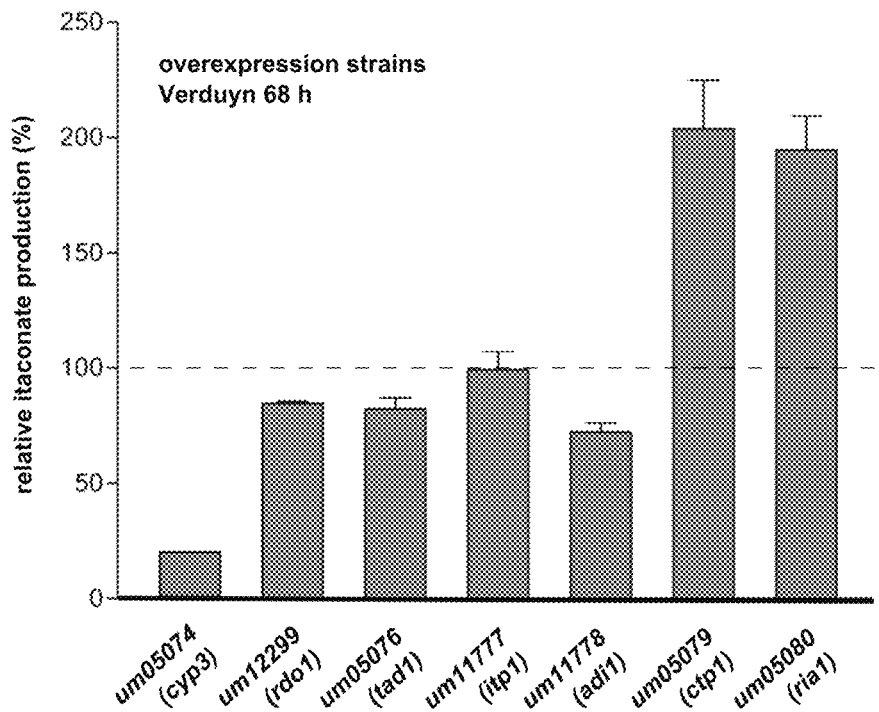

A comparison of ITA production between *U. maydis* wildtype and the deletion mutants ΔUM05076, ΔUM11778, ΔUM05074, ΔUM12299, ΔUM11777, ΔUM05079 or ΔUM05080 is shown in FIG. 2 and FIG. 3 A. A strong decrease of the itaconic acid titer was observed in ΔUM05076, ΔUM11778, ΔUM11777, ΔUM05079 and ΔUM05080 mutant strains if compared to the wild type strain. These data indicate that these genes encode enzymes important for itaconic acid production in *U. maydis*.

Overexpression of Itaconic Acid Biosynthesis Genes in *Ustilago maydis*

Figure 8:
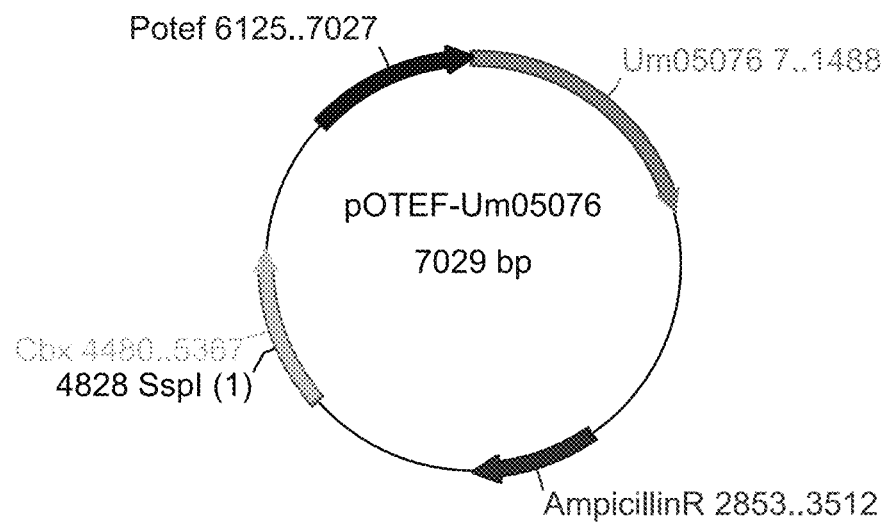
FIG. 8 Plasmid map of pOTEF-UM05076 overexpression plasmid used in the Examples. Indicated are the Potef promoter, the cbx resistance gene and the open reading frame of UM05076.
Figure 9:
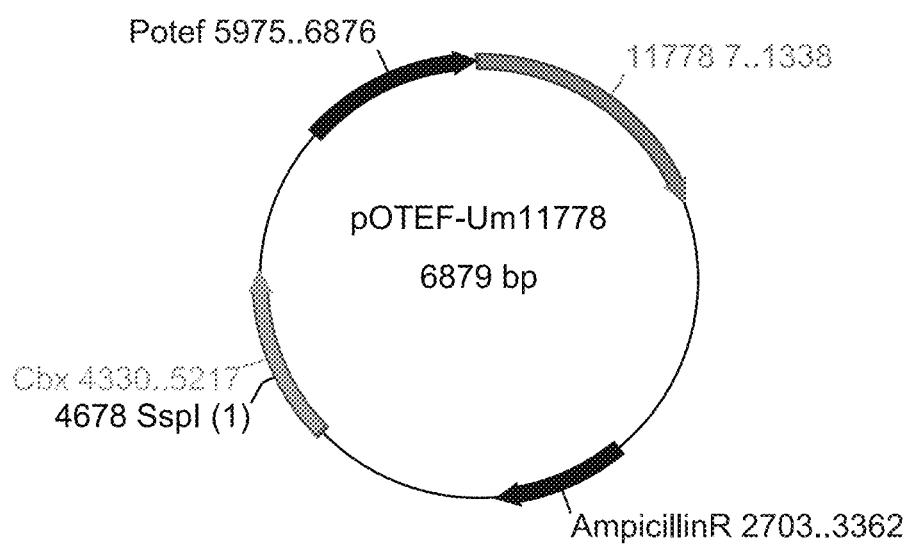
FIG. 9 Plasmid map of pOTEF-UM11778 overexpression plasmid used in the Examples. Indicated are the Potef promoter, the cbx resistance gene and the open reading frame of UM11778.

The ORFs for genes UM05076, UM11778, UM05074, UM12299, UM11777, UM05079 and UM05080 were amplified via PCR, restricted with suitable enzymes and ligated into vector Potef-GFP (Spellig et al., 1996). The final vectors contain an ampicillin resistance marker, a carboxin resistance marker, the Potef promoter and the corresponding ORFs. The corresponding plasmid map for UM05076 is shown in FIG. 8. The corresponding plasmid map for UM11778 is shown in FIG. 9. Constructs were tested by restriction analysis and confirmed by DNA sequencing.

Prior to transformation, the vector was linearized using SspI. Approximately 1 μg DNA were used for transformation of *U. maydis* MB215 strains, following integration of the construct into the ip-locus (Cbx) via homologous recombination. Transformants were checked by PCR analysis. *U. maydis* MB215 was transformed with overexpression constructs for either UM05076, UM11778, UM05074, UM12299, UM11777, UM05079 or UM05080.

The resulting overexpression mutants were assessed for itaconic acid production as described above. A comparison of itaconic acid production between *U. maydis* wildtype and the overexpression mutants is shown in FIG. 3 B. A strong increase of the itaconic acid titre was observed in strains containing UM05079 and UM05080 overexpression constructs if compared to the wild type strain. These data indicate that these genes encode enzymes that are important for itaconic acid production in *U. maydis*.

In Vivo Reconstitution of Itaconic Acid Production in Yeast

Figure 11:
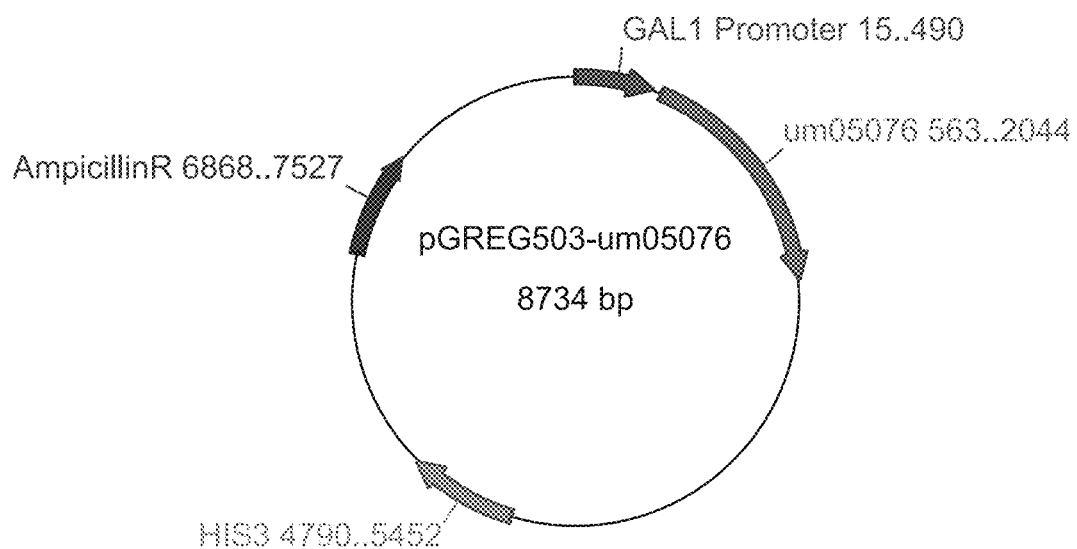
FIG. 11 Plasmid map of pGREG503-UM05076 overexpression plasmid used in the Examples. Indicated are the GAL1 promoter, the HIS3 marker and the open reading frame of UM05076.
Figure 12:
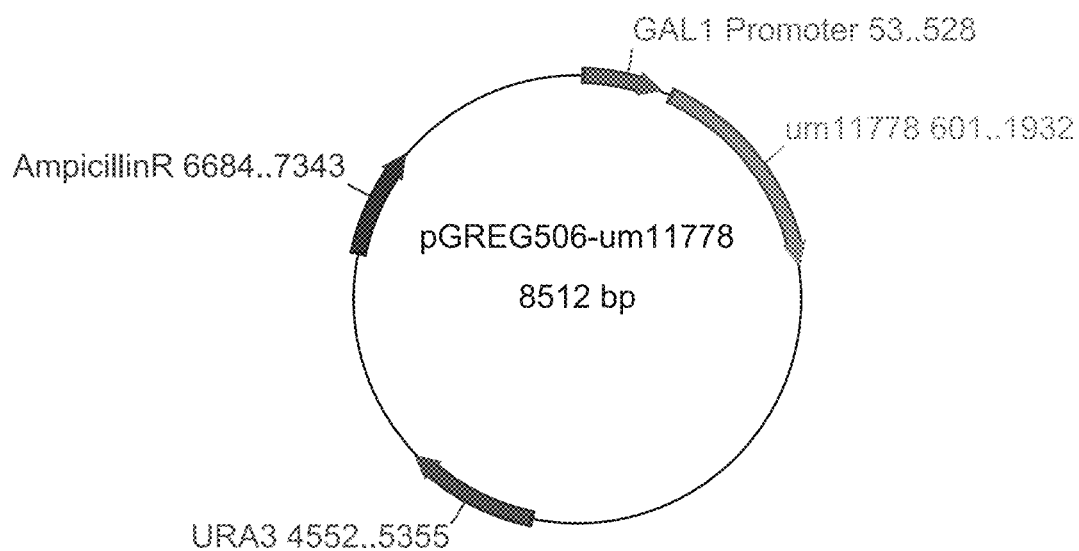
FIG. 12 Plasmid map of pGREG506-UM11778 overexpression plasmid used in the Examples. Indicated are the GAL1 promoter, the URA3 marker and the open reading frame of UM11778.

We were able to reconstitute itaconate biosynthesis in the yeast *Saccharomyces cerevisiae* by expression of um11778 and um05076. um11778 and um05076 were expressed in yeast either singly or in combination. Plasmid maps of yeast expression constructs are shown in FIG. 11 and FIG. 12. The *S. cerevisiae* strains were cultivated in 50 mL YNB+gal media (1.7 g L$^{-1}$ yeast nitrogen base without amino acids (Sigma-Aldrich, Germany), 5.0 g L$^{-1}$NH$_4$Cl, 40 g L$^{-1}$ galactose, 1.4 g L$^{-1}$ yeast synthetic drop out medium supplements without histidine, leucine, tryptophan and uracil (Sigma-Aldrich, Germany), 0.075 g L$^{-1}$ tryptophanand 0.5 g L$^{-1}$ leucine) in 500 mL Erlenmeyer flasks. According to the yeast selection markers 0.15 g L$^{-1}$ uracil and/or 0.5 g L$^{-1}$ histidine were added. Cells were grown at 30° C. and 250 rpm. The supernatant of the culture was analyzed for itaconic acid production via HPLC as described above.

Figure 10:
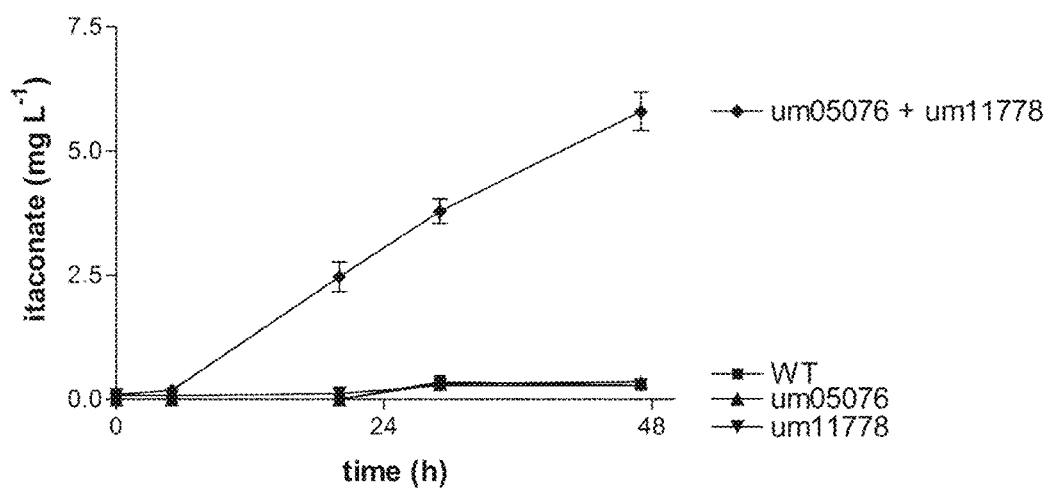
FIG. 10 In vivo reconstitution of itaconic acid production in *S. cerevisiae*. *S. cerevisiae* ESM356 (■), *S. cerevisiae* ESM356+pGREG503-um05076 (▲), *S. cerevisiae* ESM356+pGREG506-UM11778 (▼) and *S. cerevisiae* ESM356+pGREG503-UM05076+pGREG506-UM11778 (♦). Error bars indicate deviation from the mean (n=2). Coexpression of um05076 and um11778 resulted in itaconic acid formation (♦).

Single expression of either gene did not result in detectable itaconic acid production (FIG. 10). However, when both genes were coexpressed, we detected significant levels of itaconic acid production (FIG. 10). This indicates that both enzymes are sufficient to produce itaconic acid in a heterologous host system.

Characterization of Enzyme Activities of Um05076 and Um11778

We performed in vitro enzyme assays for both UM05076 and UM11778. Protein expression of UM05076 and UM11778 was performed in strain Rosetta 2(DE3) (Novagen, Madison, Wis.) using plasmids derived from pGEX4T-1 (GE Healthcare, Waukesha, Wis.). Cells were grown overnight in inducing dYT medium at 22° C. Cells were harvested by centrifugation, resuspended in lysis buffer (50 mM Tris-HCl, pH 7.5, 100 mM NaCl, 10 mM $MgCl_2$, 1 mM DTT, 1 mM PMSF) and lysed by French cell pressure. After ultra-centrifugation, the supernatant was loaded on GSH Sepharose beads (GE Healthcare) and incubated at 4° C. for 1 h. Beads were washed five times with lysis buffer and then eluted in elution buffer (100 mM Tris-HCl, pH 9.0, 100 mM NaCl, 10 mM $MgCl_2$, 1 mM DTT and 50 mM reduced glutathione). Protein concentration was determined either by Bradford or by Nanodrop.

As potential substrates we used cis-aconitate, trans-aconitate, citrate and isocitrate. 10 μg of the corresponding protein was mixed with assay-buffer (50 mM Tris-HCl pH 7.5, 100 mM NaCl, 10 mM $MgCl_2$, 1 mM DTT and 5 mM substrate) to a final volume of 100 μl in a 96-well microtiterplate (Greiner Bio-One). The samples were incubated shaking for 15 min at RT. Reaction products were analyzed in an Agilent Technologies 1260 Series system with an organic acid resin (250×8 mm; CS Chromatographie). For detection at 210 nm a variable wavelength detector (1260 VWD; Agilent Technologies) was used. The solvent was 0.25 mM sulfuric acid with a flow rate of 1.0 mL $min^{-1}$ at RT.

HPLC analysis clearly demonstrated that UM11778 is able to catalyze cis-trans-isomerization of aconitate (FIG. 13A). Therefore, we called this enzyme aconitate-delta-isomerase (ADI). UM05076 was able to convert trans-aconitate nearly completely into itaconic acid (FIG. 13B). We called this second enzyme trans-aconitate decarboxylase (TAD). To our knowledge, such enzyme activity has never been described before. In a further experiment we incubated both ADI and TAD with cis-aconitate as substrate to mimic the putative biosynthesis pathway for itaconic acid. HPLC analysis demonstrated that cis-aconitate was completely converted to itaconic acid by the sequential activity of the two enzymes (FIG. 14).

These data allowed us to propose a potential biosynthesis pathway of itaconic acid production in U. maydis (FIG. 15). We assume that cis-aconitate is exported from the mitochondria into the cytosol by the mitochondrial transporter CTP1. In the cytosol cis-aconitate is the substrate of ADI, which catalyzes isomerization to trans-aconitate. TAD uses trans-aconitate as a substrate for decarboxylation to itaconic acid. Finally, itaconic acid is exported by a transporter of the major facilitator superfamily (MFS). According to this model the itaconic acid biosynthesis route in U. maydis deviates from that in A. terreus. In A. terreus cis-aconitate decarboxylase (CAD) is solely responsible for itaconic acid biosynthesis by catalyzing a decarboxylation of cis-aconitate. In U. maydis, two enzymes are required for itaconic acid production, starting also with cis-aconitate as a substrate and ending with itaconic acid as a product.

Characterization of the ADI2 Protein Encoded by Um02807

U. maydis possesses besides um11778 (adi1) another gene encoding a putative aconitate-Δ-isomerase (ADI) protein, um02807. Deletion of this gene did not influence itaconate biosynthesis (FIG. 16B). However, um02807 is located in a small cluster, surrounded by a probable CTP1-mitochondrial citrate transporter, member of the mitochondrial carrier family (MCF), encoded by um02806 and a putative transcriptional regulator related to the nitrogen assimilation transcription factor nit-4 encoded by um02808 (FIG. 16B). These three genes showed functional similarities to the genes in the itaconate cluster of U. maydis and are arranged in the same way. BLAST analysis on protein level 200 indicated 37% sequence identity for um02806 and um05079 (mtt1) and 32% for um02807 and um11778 (adi1) (FIG. 16A and FIG. 17). However, the putative transcriptional regulator um02808 did not show any significant sequence similarity to um05080 (ria1).

The deletion of the gene um11778 (adi1) encoding the aconitate-Δ-isomerase completely abolished itaconate biosynthesis of U. maydis. Since both proteins (UM11778 and UM02807) are aconitate-Δ-isomerase proteins, UM02807 could possibly substitute the function of UM11778. To prove this assumption, the deletion mutant for um11778 (ADI) was complemented with the gene um02807 under the strong constitutive promoter $P_{etef}$ (SEQ ID NO: 31). Interestingly, the itaconate concentration of this complementation mutant U. maydis MB215 Δum11778+$P_{etef}$um02807 after 96 h was approximately threefold higher ($p=4.9\times10^{-4}$) compared to wildtype indicating that UM02807 has a similar activity to UM11778 (ADI) (FIG. 16B). Also the single overexpression of um02807 with the help of the strong constitutive promoter $P_{ad}$ could increase the itaconate concentration after 96 h to approximately 150% ($p=1.6\times10^{-3}$) compared to the wildtype. The same was done for the gene um02808 encoding a putative transcriptional regulator. However, the gene could neither complement the function of the transcriptional regulator of the known itaconate cluster UM05080 (RiaA) nor influenced its overexpression the itaconate biosynthesis positively ($p=0.111$) (FIG. 16B).

These results show that the protein encoded by UM02807, also annotated as putative methylitaconate Δ-isomerase, is probably an additional aconitate-Δ-isomerase and can take over the function of the aconitate-Δ-isomerase UM11778 (ADI). However, it was shown, that in the um11778 (adi1) deletion mutant no itaconate is formed, indicating that um02807 is not expressed under the itaconate producing conditions used in this study. Thus, um02807 is not able to compensate the deletion of um11778 (adi1) under control of its native regulator, supporting the theory of independently regulated clusters. Furthermore, this led to the assumptions that also other, redundant genes might also be involved in itaconate biosynthesis of U. maydis in other conditions, as for instance in planta.

The listing or discussion of a previously published document in this specification should not be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including,"

containing", etc. shall be read expansively and without limitation. Thus, the word "comprise" or variations such as "comprises" or "comprising" will be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A host cell genetically engineered to overexpress at least one polynucleotide sequence selected from one of (a) and (b):
   (a) a polynucleotide sequence selected from the group consisting of a polynucleotide sequence having at least 85% sequence identity with SEQ ID NO: 1, a polynucleotide sequence having at least 85% sequence identity with SEQ ID NO:7, a polynucleotide sequence encoding a protein having at least 85% sequence identity with SEQ ID NO:2, and a polynucleotide sequence encoding a protein having at least 85% sequence identity with SEQ ID NO:10, said polynucleotide sequence encoding a protein having aconitate-delta-isomerase (ADI) activity; and
   (b) a polynucleotide sequence selected from the group consisting of a polynucleotide sequence having at least 85% sequence identity with SEQ ID NO: 6, and a polynucleotide sequence encoding a protein having at least 85% sequence identity with SEQ ID NO: 13, said polynucleotide sequence encoding a protein having trans-aconitate decarboxylase (TAD) activity;
   in comparison to a comparable host cell which has not been genetically altered, wherein the host cell is a cell of a fungus or yeast.

2. The host cell of claim 1 wherein the host cell is genetically engineered to underexpress a polynucleotide sequence having at least 85% sequence identity with the sequence of SEQ ID NO: 9 in comparison to a comparable host cell which has not been genetically altered, said polynucleotide sequence encoding a protein or fragment thereof having the activity of a cytochrome P450-Monooxygenase.

3. The host cell of claim 1, wherein the host cell is genetically engineered to overexpress at least one polynucleotide sequence selected from one of (a) and (b):
   (a) a polynucleotide sequence selected from the group consisting of a polynucleotide sequence having at least 90% sequence identity with SEQ ID NO: 1, a polynucleotide sequence having at least 90% sequence identity with SEQ ID NO:7, a polynucleotide sequence encoding a protein having at least 90% sequence identity with SEQ ID NO:2, and a polynucleotide sequence encoding a protein having at least 90% sequence identity with SEQ ID NO:10, said polynucleotide sequence encoding a protein having aconitate-delta-isomerase (ADI) activity; and
   (b) a polynucleotide sequence selected from the group consisting of a polynucleotide sequence having at least 90% sequence identity with SEQ ID NO: 6, and a polynucleotide sequence encoding a protein having at least 90% sequence identity with SEQ ID NO: 13, said polynucleotide sequence encoding a protein having trans-aconitate decarboxylase (TAD) activity;
   in comparison to a comparable host cell which has not been genetically altered, wherein the host cell is a cell of a fungus or yeast.

4. The host cell of claim 1, wherein the host cell is genetically engineered to overexpress at least one polynucleotide sequence selected from one of (a) and (b):
   (a) a polynucleotide sequence selected from the group consisting of a polynucleotide sequence having at least 95% sequence identity with SEQ ID NO: 1, a polynucleotide sequence having at least 95% sequence identity with SEQ ID NO:7, a polynucleotide sequence encoding a protein having at least 95% sequence identity with SEQ ID NO:2, and a polynucleotide sequence encoding a protein having at least 95% sequence identity with SEQ ID NO:10, said polynucleotide sequence encoding a protein having aconitate-delta-isomerase (ADI) activity; and
   (b) a polynucleotide sequence selected from the group consisting of a polynucleotide sequence having at least 95% sequence identity with SEQ ID NO: 6, and a polynucleotide sequence encoding a protein having at least 95% sequence identity with SEQ ID NO: 13, said polynucleotide sequence encoding a protein having trans-aconitate decarboxylase (TAD) activity;
   in comparison to a comparable host cell which has not been genetically altered, wherein the host cell is a cell of a fungus or yeast.

5. The host cell of claim 1, wherein the host cell is genetically engineered to overexpress at least one polynucleotide sequence selected from one of (a) and (b):
   (a) a polynucleotide sequence selected from the group consisting of a polynucleotide sequence having at least 98% sequence identity with SEQ ID NO: 1, a polynucleotide sequence having at least 98% sequence identity with SEQ ID NO:7, a polynucleotide sequence encoding a protein having at least 98% sequence identity with SEQ ID NO:2, and a polynucleotide sequence encoding a protein having at least 98% sequence identity with SEQ ID NO:10, said polynucleotide sequence encoding a protein having aconitate-delta-isomerase (ADI) activity; and
(b) a polynucleotide sequence selected from the group consisting of a polynucleotide sequence having at least 98% sequence identity with SEQ ID NO: 6, and a polynucleotide sequence encoding a protein having at least 98% sequence identity with SEQ ID NO: 13, said polynucleotide sequence encoding a protein having trans-aconitate decarboxylase (TAD) activity;
in comparison to a comparable host cell which has not been genetically altered, wherein the host cell is a cell of a fungus or yeast.

6. The host cell of claim 1, wherein the host cell is genetically engineered to overexpress at least one polynucleotide sequence selected from one of (a) and (b):
(a) a polynucleotide sequence selected from the group consisting of a polynucleotide sequence comprising SEQ ID NO: 1, a polynucleotide sequence comprising and SEQ ID NO: 7, a polynucleotide sequence encoding a protein comprising SEQ ID NO: 2, and a polynucleotide sequence encoding a protein comprising SEQ ID NO:10, said polynucleotide sequence encoding a protein having aconitate-delta-isomerase (ADI) activity; and
(b) a polynucleotide sequence selected from the group consisting of a polynucleotide sequence comprising SEQ ID NO: 6, and a polynucleotide sequence encoding a protein comprising SEQ ID NO: 13, said polynucleotide sequence encoding a protein having trans-aconitate decarboxylase (TAD) activity;
in comparison to a comparable host cell which has not been genetically altered, wherein the host cell is a cell of a fungus or yeast.

7. The host cell of claim 1, wherein said host cell further overexpresses a polynucleotide sequence selected from:
a polynucleotide sequence having at least 85% sequence identity with the sequence of SEQ ID NO: 4, said polynucleotide sequence encoding a protein or fragment thereof having activity of a mitochondrial citrate transporter, or activity of a mitochondrial cis-aconitate transporter;
a polynucleotide sequence having at least 85% sequence identity with the sequence of SEQ ID NO: 6, said polynucleotide sequence encoding a protein or fragment thereof having trans-aconitate decarboxylase (TAD) activity; and
a polynucleotide sequence having at least 85% sequence identity with the sequence of SEQ ID NO: 8, said polynucleotide sequence encoding a protein or fragment thereof having the activity of a transcription factor for at least one polynucleotide sequence selected from SEQ ID NOs: 1, 3, 4, and 6.

8. A method of producing itaconic acid, comprising
(a) culturing a recombinant host cell which is genetically engineered to overexpress at least one polynucleotide sequence selected from one of (i) and (ii):
(i) a polynucleotide sequence selected from the group consisting of a polynucleotide sequence having at least 85% sequence identity with SEQ ID NO: 1, a polynucleotide sequence having at least 85% sequence identity with SEQ ID NO:7, a polynucleotide sequence encoding a protein having at least 85% sequence identity with SEQ ID NO:2, and a polynucleotide sequence encoding a protein having at least 85% sequence identity with SEQ ID NO:10, said polynucleotide sequence encoding a protein or fragment thereof having aconitate-delta-isomerase (ADI) activity; and
(ii) a polynucleotide sequence selected from the group consisting of a polynucleotide sequence having at least 85% sequence identity with SEQ ID NO: 6, and a polynucleotide sequence encoding a protein having at least 85% sequence identity with SEQ ID NO: 13, said polynucleotide sequence encoding a protein or fragment thereof having trans-aconitate decarboxylase (TAD) activity,
in comparison to a comparable host cell which has not been genetically altered under conditions to allow said host cell to overexpress said polynucleotide sequence (i) or (ii), thereby said host cell is capable of converting cis-aconitate via trans-aconitate to itaconic acid; and
(b) obtaining itaconic acid, wherein
the host cell is a cell of a fungus or yeast.

9. The method of claim 8, wherein said host cell further overexpresses a polynucleotide sequence selected from:
a polynucleotide sequence having at least 85% sequence identity with the sequence of SEQ ID NO: 4, said polynucleotide sequence encoding a protein or fragment thereof having activity of a mitochondrial citrate transporter, or activity of a mitochondrial cis-aconitate transporter;
a polynucleotide sequence having at least 85% sequence identity with the sequence of SEQ ID NO: 6, said polynucleotide sequence encoding a protein or fragment thereof having trans-aconitate decarboxylase (TAD) activity; and
a polynucleotide sequence having at least 85% sequence identity with the sequence of SEQ ID NO: 8, said polynucleotide sequence encoding a protein or fragment thereof having the activity of a transcription factor for at least one polynucleotide sequence selected from the group consisting of SEQ ID NOs: 1, 3, 4, and 6.

10. The method of claim 9, wherein at least one of the polynucleotide sequences selected from the group consisting of SEQ ID NOs: 1, 3, 4, and 6 is overexpressed in comparison to a host cell prior to genetically engineering.

11. The method of claim 8, wherein overexpression is achieved by at least one selected from the group consisting of
using a recombinant promoter, which drives expression of at least one of said polynucleotides in said host cell;
expressing 2, 3, 4 or more copies of at least one of said polynucleotide in said host cell; and
using an enhancer to express at least one of the polynucleotides.

12. The method of claim 8, wherein at least one of said polynucleotides is integrated in the genome of said host cell.

13. The method of claim 8, wherein the method results in production of itaconic acid of 2 g/L or more after 48 h culture.

14. The method of claim 8, wherein said host cell is genetically engineered to underexpress a polynucleotide sequence having at least 85% sequence identity with the sequence of SEQ ID NO: 9 in comparison to a comparable host cell which has not been genetically altered, said polynucleotide sequence encoding a protein or fragment thereof having the activity of a cytochrome P450-Monooxygenase.

15. The method of claim 8, wherein said polynucleotide sequence is a heterologous polynucleotide sequence.

16. The method of claim 8, wherein said cell of a fungus is a cell from a fungus selected from the group consisting of *Ustilago maydis, Aspergillus terreus* and *Saccharomyces cerevisiae.*

17. The method of claim 8, further comprising providing the host cell with a suitable carbon source.

18. The method of claim 8, further comprising isolating itaconic acid from a medium in which the host cell is cultured.

19. The method of claim 17, wherein the carbon source comprises at least one selected from the group consisting of a monosaccharide, a polysaccharide, a lipid and a fatty acid.

20. The method of claim 19, wherein the monosaccharide is selected from the group consisting of mannose, glucose, arabinose and xylose.

21. The method of claim 19, wherein the polysaccharide is selected from the group consisting of starch, a mannan and cellulose.

22. The method of claim 19, wherein the lipid is triacylglycerol.

23. The method of claim 8, wherein the recombinant host cell is genetically engineered to overexpress at least one polynucleotide sequence selected from one of (i) and (ii):
   (i) a polynucleotide sequence selected from the group consisting of a polynucleotide sequence having at least 90% sequence identity with SEQ ID NO: 1, a polynucleotide sequence having at least 90% sequence identity with SEQ ID NO:7, a polynucleotide sequence encoding a protein having at least 90% sequence identity with SEQ ID NO:2, and a polynucleotide sequence encoding a protein having at least 90% sequence identity with SEQ ID NO:10, said polynucleotide sequence encoding a protein or fragment thereof having aconitate-delta-isomerase (ADI) activity; and
   (ii) a polynucleotide sequence selected from the group consisting of a polynucleotide sequence having at least 90% sequence identity with SEQ ID NO: 6, and a polynucleotide sequence encoding a protein having at least 90% sequence identity with SEQ ID NO: 13, said polynucleotide sequence encoding a protein or fragment thereof having trans-aconitate decarboxylase (TAD) activity.

24. The method of claim 8, wherein the recombinant host cell is genetically engineered to overexpress at least one polynucleotide sequence selected from one of (i) and (ii):
   (i) a polynucleotide sequence selected from the group consisting of a polynucleotide sequence having at least 95% sequence identity with SEQ ID NO: 1, a polynucleotide sequence having at least 95% sequence identity with SEQ ID NO:7, a polynucleotide sequence encoding a protein having at least 95% sequence identity with SEQ ID NO:2, and a polynucleotide sequence encoding a protein having at least 95% sequence identity with SEQ ID NO:10, said polynucleotide sequence encoding a protein or fragment thereof having aconitate-delta-isomerase (ADI) activity; and
   (ii) a polynucleotide sequence selected from the group consisting of a polynucleotide sequence having at least 95% sequence identity with SEQ ID NO: 6, and a polynucleotide sequence encoding a protein having at least 95% sequence identity with SEQ ID NO: 13, said polynucleotide sequence encoding a protein or fragment thereof having trans-aconitate decarboxylase (TAD) activity.

25. The method of claim 8, wherein the recombinant host cell is genetically engineered to overexpress at least one polynucleotide sequence selected from one of (i) and (ii):
   (i) a polynucleotide sequence selected from the group consisting of a polynucleotide sequence having at least 98% sequence identity with SEQ ID NO: 1, a polynucleotide sequence having at least 98% sequence identity with SEQ ID NO:7, a polynucleotide sequence encoding a protein having at least 98% sequence identity with SEQ ID NO:2, and a polynucleotide sequence encoding a protein having at least 98% sequence identity with SEQ ID NO:10, said polynucleotide sequence encoding a protein or fragment thereof having aconitate-delta-isomerase (ADI) activity; and
   (ii) a polynucleotide sequence selected from the group consisting of a polynucleotide sequence having at least 98% sequence identity with SEQ ID NO: 6, and a polynucleotide sequence encoding a protein having at least 98% sequence identity with SEQ ID NO: 13, said polynucleotide sequence encoding a protein or fragment thereof having trans-aconitate decarboxylase (TAD) activity.

26. The method of claim 8, wherein the recombinant host cell is genetically engineered to overexpress at least one polynucleotide sequence selected from one of (i) and (ii):
   (i) a polynucleotide sequence selected from the group consisting of a polynucleotide sequence comprising SEQ ID NO: 1, a polynucleotide sequence comprising SEQ ID NO:7, a polynucleotide sequence encoding a protein comprising SEQ ID NO:2, and a polynucleotide sequence encoding a protein comprising SEQ ID NO:10, said polynucleotide sequence encoding a protein or fragment thereof having aconitate-delta-isomerase (ADI) activity; and
   (ii) a polynucleotide sequence selected from the group consisting of a polynucleotide sequence comprising SEQ ID NO: 6, and a polynucleotide sequence encoding a protein comprising SEQ ID NO: 13, said polynucleotide sequence encoding a protein or fragment thereof having trans-aconitate decarboxylase (TAD) activity.

\* \* \* \* \*